(12) United States Patent  
Carter et al.

(10) Patent No.: US 8,283,339 B2
(45) Date of Patent: Oct. 9, 2012

(54) VINYL PHOSPHONATE LYSOPHOSPHATIDIC ACID RECEPTOR ANTAGONISTS

(75) Inventors: Karen M. Carter, Louisa, VA (US); Kevin R. Lynch, Charlottesville, VA (US); Timothy L. Macdonald, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 568 days.

(21) Appl. No.: 12/357,728

(22) Filed: Jan. 22, 2009

(65) Prior Publication Data

US 2009/0197835 A1 Aug. 6, 2009

Related U.S. Application Data

(63) Continuation of application No. PCT/US2007/074262, filed on Jul. 24, 2007.

(60) Provisional application No. 60/823,835, filed on Jul. 24, 2006.

(51) Int. Cl.
- *A01N 57/00* (2006.01)
- *A61K 31/675* (2006.01)
- *C07F 9/06* (2006.01)
- *C07F 9/28* (2006.01)
- *C07F 9/22* (2006.01)

(52) U.S. Cl. .............................. 514/89; 546/22; 562/11
(58) Field of Classification Search .................. 514/89; 546/22; 562/11
See application file for complete search history.

(56) References Cited

FOREIGN PATENT DOCUMENTS

| WO | WO-2005115150 A2 | 12/2005 |
| WO | WO-2008014286 A1 | 1/2008 |

OTHER PUBLICATIONS

"European Application Application No. 07813308.9, Office Action mailed Feb. 9, 2010", 2 pgs.
"European Application Application No. 07813308.9, Response filed Aug. 19, 2010 to Office Action mailedFeb. 9, 2010", 9 pgs.
"International Application Serial No. PCT/US2007/074262, International Search Report mailed Dec. 13, 2007", 3 pgs.
Cui, Peng, et al., "Synthesis and biological evalution of phostonate derivatives as autotaxin (STX) inhibitors", Bioorganic & Medical Chemistry Letters, vol. 17, No. 6, (Feb. 1997), 1634-1640.
Heasley, B. H, et al., "Initial structure-activity relationships of lysophosphatidic acid receptor antagonists: discovery of a high-affinity LPA1/LPA3 receptor antagonist.", Bioorg Med Chem Lett., 14(11), (Jun. 7, 2004), 2735-40.
Heasley, B.H., et al., "A novel series of 2-pyridyl-containing compounds as lysophosphatidic acid receptor antagonists: development of a nonhydrolyzable LPA3 receptor-selective antagonist", Bioorganic & Medicinal Chemistry Letters, vol. 14, No. 15, (Aug. 2004), 4069-4074.
Kassel, et al., "Different lysophosphatidic acid receptors mediate the direct stimulation of proliferation and the synegism with EGF in airway smooth muscle cells", ACTA Pharmacologica Sinica, vol. 27, No. Suppl. 1, (Jul. 2006), 379.

*Primary Examiner* — Sreeni Padmanabhan
*Assistant Examiner* — Kendra D Carter
(74) *Attorney, Agent, or Firm* — Schwegman, Lundberg & Woessner, P.A.

(57) ABSTRACT

The present invention provides LPA analogs that are antagonists at the LPA receptors.

17 Claims, 40 Drawing Sheets

Scheme 1

Scheme 2

CAM assay

BSA-treated CAM

LPA-treated CAM

VPC51299-treated CAM

LPA+51299-treated CAM

Thermal Hyperalgesia

07-0105_22_tumors 07-0105_22_vessels_clipped 07-0105_22_mip 07-0105_22_vessels 07-0105_39_tumors 07-0105_39_vessels_clipped 07-0105_39_mip 07-0105_39_vessels 07-0105_81_tumors 07-0105_81_vessels_clipped 07-0105_81_mip 07-0105_81_vessels 07-0105_85_tumors 07-0105_85_vessels_clipped 07-0105_85_mip 07-0105_85_vessels 07-0105_87_tumors 07-0105_87_vessels_clipped 07-0105_87_mip 07-0105_87_vessels 07-0105_88_tumors 07-0105_88_vessels_clipped 07-0105_88_mip 07-0105_88_vessels 07-0105_89_tumors 07-0105_89_vessels_clipped 07-0105_89_mip 07-0105_89_vessels 07-0105_92_tumors 07-0105_92_vessels_clipped 07-0105_92_mip 07-0105_92_vessels 07-0105_96_tumors 07-0105_96_vessels_clipped 07-0105_96_mip 07-0105_96_vessels

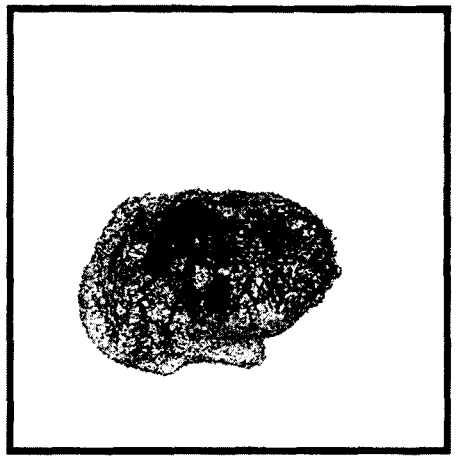
Fig. 11b 07-0105_5_tumors
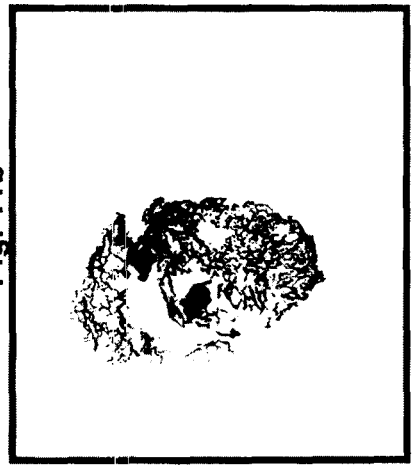
Fig. 11d 07-0105_5_vessels_clipped
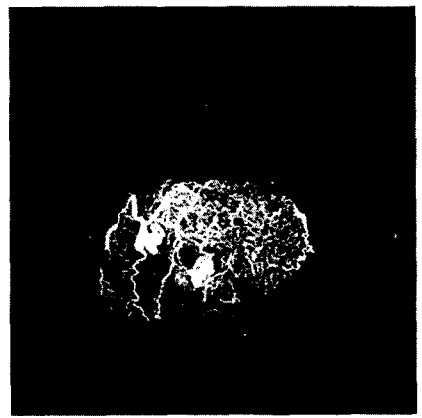
Fig. 11a 07-0105_5_mip
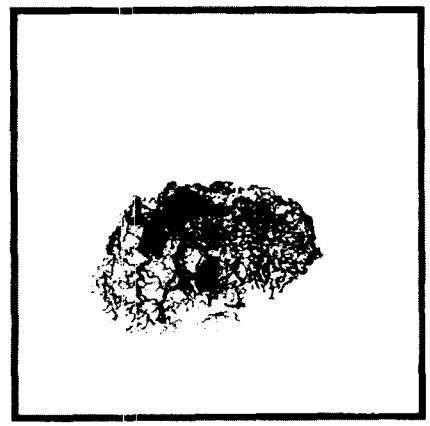
Fig. 11c 07-0105_5_vessels 07-0105_19_tumors 07-0105_19_vessels_clipped 07-0105_19_mip 07-0105_19_vessels 07-0105_25_tumors 07-0105_25_vessels_clipped 07-0105_25_mip 07-0105_25_vessels 07-0105_42_tumors 07-0105_42_vessels_clipped 07-0105_42_mip 07-0105_42_vessels 07-0105_59_tumors 07-0105_59_vessels_clipped 07-0105_59_mip 07-0105_59_vessels 07-0105_78_tumors 07-0105_78_vessels_clipped 07-0105_78_mip 07-0105_78_vessels 07-0105_90_tumors 07-0105_90_vessels_clipped 07-0105_90_mip 07-0105_90_vessels 07-0105_94_tumors 07-0105_94_vessels_clipped 07-0105_94_mip 07-0105_94_vessels 07-0105_99_tumors 07-0105_99_vessels_clipped 07-0105_99_mip 07-0105_99_vessels 07-0105_100_tumors 07-0105_100_vessels_clipped 07-0105_100_mip 07-0105_100_vessels 07-0105_12_tumors 07-0105_12_vessels_clipped 07-0105_12_mip 07-0105_12_vessels 07-0105_62_tumors 07-0105_62_vessels_clipped 07-0105_62_mip 07-0105_62_vessels 07-0105_72_tumors 07-0105_72_vessels_clipped 07-0105_72_mip 07-0105_72_vessels 07-0105_76_tumors 07-0105_76_vessels_clipped 07-0105_76_mip 07-0105_76_vessels 07-0105_77_tumors 07-0105_77_vessels_clipped 07-0105_77_mip 07-0105_77_vessels 07-0105_79_tumors 07-0105_79_vessels_clipped 07-0105_79_mip 07-0105_79_vessels 07-0105_80_tumors 07-0105_80_vessels_clipped 07-0105_80_mip 07-0105_80_vessels 07-0105_82_tumors 07-0105_82_vessels_clipped 07-0105_82_mip 07-0105_82_vessels 07-0105_83_tumors 07-0105_83_vessels_clipped 07-0105_83_mip 07-0105_83_vessels 07-0105_98_tumors 07-0105_98_vessels_clipped 07-0105_98_mip 07-0105_98_vessels Radiographic Analysis Group A | Group B Fluorescence imaging

VINYL PHOSPHONATE LYSOPHOSPHATIDIC ACID RECEPTOR ANTAGONISTS

CROSS-REFERENCE TO RELATED APPLICATION

This application is a continuation of international application PCT/US2007/074262, filed on Jul. 24, 2007, and published in English as WO 2008/014286 on Jan. 31, 2008, which claims priority from U.S. Provisional Application Ser. No. 60/832,835, filed Jul. 24, 2006, the disclosures of which are incorporated herein by reference.

US GOVERNMENT RIGHTS

This invention was made with United States Government support under Grant No. Grant No R01 GM052722 awarded by the National Institutes of Health. The United States Government may have certain rights in the invention.

BACKGROUND OF THE INVENTION

Lysophosphatidic acids (LPAs) are lysophospholipid mediators that can evoke a variety of responses when applied to living mammalian cells. These include calcium mobilization, changes in the cytoskeleton that may lead to increased migration, increased cell survival, resistance to apoptosis and mitogenesis. LPA is also believed to promote platelet aggregation in a number of mammalian species including humans. Further, LPA is a pro-angiogenic factor. LPA signals through a set of at least three G protein-coupled receptors, named $LPA_1$, $LPA_2$ and $LPA_3$ (formerly EDG2, EDG4 and EDG7). Other receptors for LPA, including the G protein-coupled receptors GPR23 and GPR92 and a nuclear hormone receptor (PPAR-$\gamma$) have been suggested.

LPA is an intermediate that is present during phospholipid biosynthesis in all cells. It is made via a common de novo phospholipid biosynthetic pathway. Extracellular (plasma) LPA is derived mainly by the action of the plasma phosphodiesterase, autotaxin (ENPP-2), on lysophosphatidylcholine (LPC). LPA levels in human plasma are reported to be in the range of about 200-600 nanomolar (nM). LPA in serum is derived, directly and indirectly, from activated platelets. Serum LPA concentrations are in the range of about 2-6 micromolar ($\mu$M). Extracellular LPA accumulation is characteristic of the ascitic fluid often associated with human ovarian cancer. LPA is believed to be a pro-mitogenic stimulus for the ovarian cancer cells. LPA concentrations in these malignant ascites has been reported to be in the range of about 2-50 $\mu$M.

LPA has been suggested to have a role in preventing the progression of neoplastic diseases. However, the lack of suitable LPA receptor antagonist molecules has made this difficult to prove. LPA is angiogenic in a chicken chorioallantoic membrane model, which suggests a role of LPA signaling in angiogenic processes such tumor development. Mice wherein the LPA, receptor gene is deleted do not develop neuropathic pain normally, which suggests a role for this receptor type in development of neuropathic pain.

Currently, there is a need for novel, potent, and selective compounds and methods for preventing the progression of cancers. There is a longstanding need to identify LPA receptor antagonists that can modulate the activity of one or more LPA receptors. The present invention satisfies these needs.

SUMMARY

The present invention provides in one aspect compounds that have antagonist activity at one or more of the LPA receptors. The compounds are LPA analogs that can behave as antagonists at LPA receptors. Accordingly, there is provided a compound of formula I:

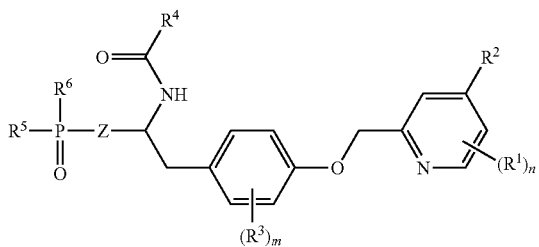

wherein Z is —CY=CH— or —C≡C—; wherein when Z is —CY=CH— then the double bond is in the trans (e) configuration; Y is hydrogen or halogen, each $R^1$ is independently halo, $(C_1-C_6)$alkyl, halo$(C_1-C_6)$alkyl, $(C_1-C_6)$alkoxy, —$NH_2$, —$NH(C_1-C_6)$alkyl, —$N((C_1-C_6)$alkyl$)_2$, or cyano; and $R^2$ is hydrogen, halo, $(C_1-C_{12})$alkyl, halo$(C_1-C_{12})$alkyl, halo$(C_1-C_{12})$alkoxyl, $(C_3-C_{12})$cycloalkyl, $(C_2-C_{12})$alkenyl, $(C_2-C_{12})$alkynyl, —$NH_2$, —$NH(C_1-C_{12})$alkyl, —$N((C_1-C_{12})$alkyl$)_2$, $(C_6-C_{10})$aryl, $(C_1-C_{12})$alkaryl, $(C_6-C_{10})$aryl$(C_1-C_{12})$alkyl, or $(C_6-C_{10})$aryl-substituted $(C_6-C_{10})$aryl$(C_1-C_{12})$alkyl. Each $R^3$ is independently halo, $(C_1-C_{12})$alkyl, halo$(C_1-C_{12})$alkyl, halo$(C_1-C_{12})$alkoxyl, $(C_3-C_{12})$cycloalkyl, $(C_2-C_{12})$alkenyl, $(C_2-C_{12})$alkynyl, —$NH_2$, —$NH(C_1-C_{12})$alkyl, —$N((C_1-C_{12})$alkyl$)_2$, $(C_6-C_{10})$aryl, $(C_1-C_{12})$alkyl$(C_6-C_{10})$aryl, $(C_6-C_{10})$aryl$(C_1-C_{12})$alkyl, or aryl-substituted aryl$(C_1-C_{12})$alkyl. $R^4$ is $(C_6-C_{24})$alkyl, halo$(C_6-C_{24})$alkyl, $(C_6-C_{24})$alkoxy, —$NH_2$, —$NH(C_1-C_{24})$alkyl, —$N((C_1-C_{24})$alkyl$)_2$, cyano, $(C_3-C_{10})$cycloalkyl, $(C_4-C_{15})$bicycloalkyl, $(C_6-C_{24})$alkenyl, $(C_6-C_{24})$-alkynyl, $(C_6-C_{10})$aryl, $(C_{12}-C_{34})$alkyl$(C_6-C_{10})$aryl, $(C_6-C_{10})$aryl$(C_{12}-C_{34})$alkyl, or $(C_6-C_{10})$aryl-substituted $(C_6-C_{10})$aryl$(C_{12}-C_{34})$alkyl; wherein the alkyl, alkenyl aryl groups of $R^4$ can be optionally substituted with halo, alkoxy or cyano. $R^5$ and $R^6$ are independently hydroxy, $(C_1-C_{12})$alkyl-O—, $(C_2-C_{12})$alkenyl-O—, $(C_2-C_{12})$alkynyl-O—, $(C_6-C_{10})$aryl-O—,

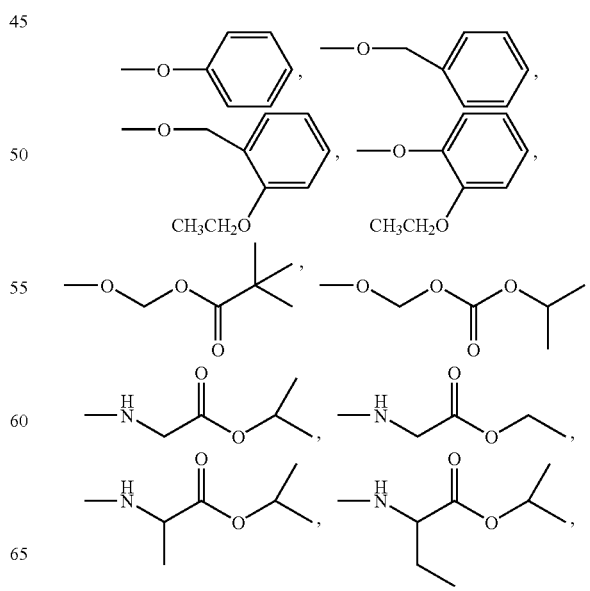

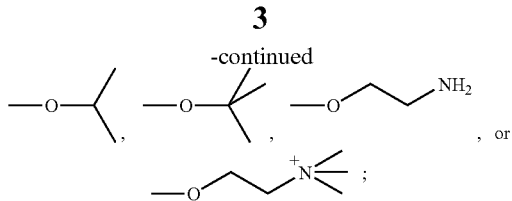

m is 0, 1, 2, 3, or 4; n is 0, 1, 2, or 3; or a pharmaceutically acceptable salt or ester thereof.

The present invention also provides esters of any of the compounds having formula I having an ester function added to form pro-drugs to increase oral availability.

The invention also provides compounds of formula (I) for use in medical therapies.

In another aspect, the present invention also provides:
a method for inhibiting angiogenesis in a tumor, including contacting the cancerous cells with an effective amount of a compound of formula I, a pharmaceutically acceptable salt or ester thereof;
a method for preventing, inhibiting or treating neuropathic pain, wherein the method includes administering an effective amount of at least one compound of formula I or a compound of formula I and a pharmaceutically-acceptable carrier to a subject in need thereof;
a method for repairing vascular injuries following catheterization, including contacting the lumen of the affected vessel with an effective amount of the compound of formula I; or
a compound of formula I, or a pharmaceutically acceptable salt thereof for use in medical treatment (for example, treatment of neoplastic disease, treatment of neuropathic pain or treatment of an ischemia-reperfusion injury).

In another aspect, the invention provides a method for reducing damage resulting from an ischemia-reperfusion injury. Examples of an ischemia-reperfusion injury include myocardial infarction, ischemic stroke, an ischemic-reperfusion injury to the kidney and the like The method includes administration of an effective amount of a compound of formula I, a pharmaceutically acceptable salt or ester thereof to a patient in need thereof (for example, a human).

In another aspect, the invention provides the use of a compound of formula I, a pharmaceutically acceptable salt or ester thereof to prepare a medicament for inhibiting tumor growth, metastasis or tumor angiogenesis in a mammalian species (for example, a human).

In another aspect, the invention provides a compound of formula I, a pharmaceutically acceptable salt or ester thereof for use in medical treatment (for example, treatment of neoplastic disease, inhibiting tumor growth, treatment of neuropathic pain, or treating vascular injuries or treatment of an ischemia-reperfusion injury).

In another aspect, the invention provides pro-drugs of the compounds of formula I. The invention also provides pharmaceutically acceptable salts or esters of compounds of formula I for use in medial therapy.

In another aspect, the invention provides for the use of a compound of formula I, a pharmaceutically acceptable salt or ester thereof to prepare a medicament for treating neuropathic pain in a mammalian species (for example, a human).

In another aspect, the invention provides a method for the use of a compound of formula I, a pharmaceutically acceptable salt or ester thereof to prepare a medicament for inhibiting tumor growth, metastasis or tumor angiogenesis in a mammalian species (for example, a human).

In another aspect, the present invention provides compositions and methods for the use of LPA analogs and LPA pro-drugs for the treatment of neoplastic disease. In one aspect, this treatment is effected by application of LPA receptor antagonists that are efficacious by virtue of their anti-angiogenic properties.

The invention includes also a method for binding a compound of formula I (e.g., $LPA_1/LPA_3$ receptor antagonists) to designated receptor sites comprising in vivo or in vitro, with an amount of a compound of formula I effective to bind said receptors. Tissue having ligand bound designated LPA receptor sites can be used to measure the selectivity of test compounds for specific receptor subtypes, or can be used as a tool to identify potential therapeutic agents for the treatment of diseases, by contacting said agents with said ligand-receptor complexes, and measuring the extent of displacement of the ligand and/or binding of the agent.

In another aspect, the invention provides novel intermediates and processes disclosed herein that are useful for preparing compounds of formula I, including the generic and specific intermediates as well as the synthetic processes described herein.

In another aspect, the present invention provides synthetic schemes and methods of use of compounds having formula I and analogs or derivatives thereof. In another aspect, the invention provides synthetic and modification schemes for preparing analogs and derivatives of the compounds of formula I, as well as compositions and methods for the use of such analogs and derivatives.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The details of one or more embodiments of the invention are set forth in the accompanying description below. Other features, objects, and advantages of the invention will be apparent from the description and drawings, and from the claims.

DETAILED DESCRIPTION

Figure 1A:
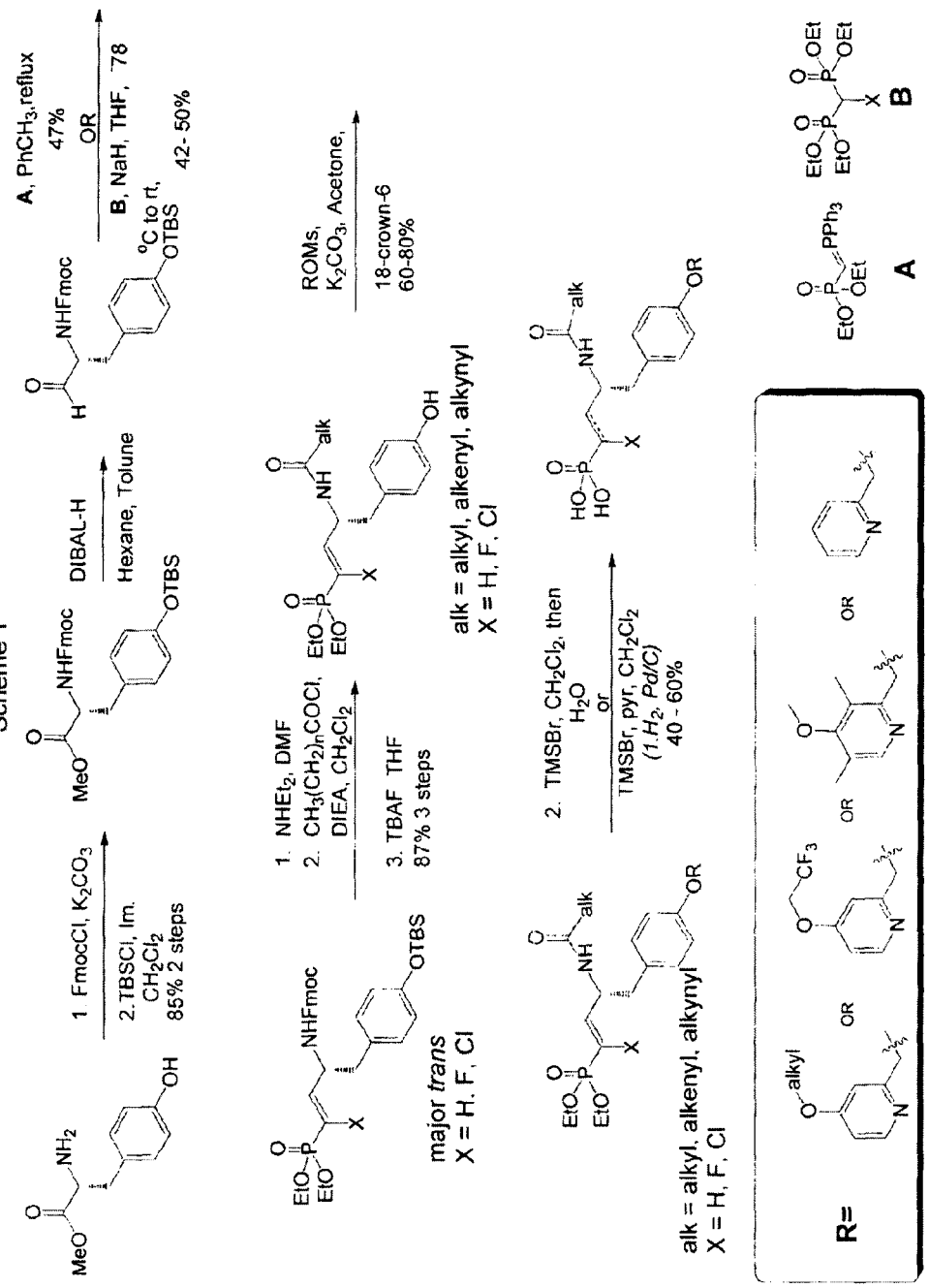
FIGS. 1A and 1B illustrate a general synthesis of the LPA antagonists.

The following abbreviations are used herein: GPCR, G-protein coupled receptor; SAR, structure-activity relationship; LPA, lysophosphatidic acid; $LPA_1$, $LPA_2$, $LPA_3$, LPA receptor types; EDG, endothelial cell differentiation gene; and RT-PCR, reverse transcriptase polymerase chain reaction.

In describing and claiming the invention, unless otherwise defined, all technical and scientific terms used herein have the same meaning as commonly understood by one of ordinary skill in the art to which this invention belongs. Although any materials and methods similar or equivalent to those described herein can be used in the practice or testing of the present invention, the preferred materials and methods are described herein. Each of the following terms has meaning associated with it in this section. Specific and preferred values listed below for radicals, substituents, and ranges are for illustrations only; they do not exclude other defined values or other values within defined ranges for the radicals and substituents.

The terms "a," "an," "the," "at least one," and "one or more" are used interchangeably. Thus, for example, a composition that comprises "an" element means one element or more than one element.

The term "receptor agonists" are compounds that mimic the action of LPA at one or more of its receptors but may have differing potency and/or efficacy.

The term "receptor antagonists" are compounds that 1) lack intrinsic agonist activity and 2) block agonist (e.g., LPA) activation of the LPA receptor(s), often in a manner that is both fully surmountable and reversible ('competitive antagonist').

The term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

A disease or disorder is "alleviated" if the severity of a symptom of the disease or disorder, the frequency with which such a symptom is experienced by a patient, or both, is reduced.

An "analog" of a chemical compound is a compound that, by way of example, resembles another in structure but is not necessarily an isomer (e.g., 5-fluorouracil is an analog of thymine).

The terms "cell," "cell line," and "cell culture" may be used interchangeably.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

A "detectable marker" or a "reporter molecule" is an atom or a molecule that permits the specific detection of a compound having the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" means an amount sufficient to produce a selected effect. For example, an effective amount of an LPA receptor antagonist is an amount that decreases the cell signaling activity of the LPA receptor.

A "functional" molecule is a molecule in a form in which it exhibits a property by which it is characterized. By way of example, a functional enzyme is one which exhibits the characteristic catalytic activity by which the enzyme is characterized.

The term "inhibit" refers to the ability of a disclosed compound to reduce or impede a described function. Preferably, inhibition is by at least 10%, more preferably by at least 25%, even more preferably by at least 50%, and most preferably, the function is inhibited by at least 75%.

"Instructional material" includes a publication, a recording, a diagram, or any other medium of expression which can be used to communicate the usefulness of the disclosed compounds in the kit for effecting alleviation of the various diseases or disorders recited herein. Optionally, or alternately, the instructional material may describe one or more methods of alleviating the diseases or disorders in a cell or a tissue of a mammal. The instructional material of the kit may, for example, be affixed to a container which contains a disclosed compound or be shipped together with a container which contains the identified compound. Alternatively, the instructional material may be shipped separately from the container with the intention that the instructional material and the compound be used cooperatively by the recipient.

The term "parenteral" means not through the alimentary canal but by some other route such as subcutaneous, intramuscular, intraspinal, or intravenous.

The term "purified" and similar terms relate to the isolation of a molecule or compound in a form that is substantially free (at least 75% free, preferably 90% free, and most preferably at least 95% free) from other components normally associated with the molecule or compound in a native environment. The term "purified" does not necessarily indicate that complete purity of the particular molecules achieved during the process. A "very pure" compound refers to a compound that is greater than 90% pure. A "highly purified" compound refers to a compound that is greater than 95% pure.

A "sample" refers preferably to a biological sample from a subject, including, but not limited to, normal tissue samples, diseased tissue samples, biopsies, blood, saliva, feces, semen, tears, and urine. A sample can also be any other source of material obtained from a subject, which contains cells, tissues, or fluid of interest. A sample can also be obtained from cell or tissue culture.

The term "standard," refers to something used for comparison. For example, a standard can be a known standard agent or compound which is administered or added to a control sample and used for comparing results when measuring said compound in a test sample. Standard can also refer to an "internal standard," such as an agent or compound that is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "treating" includes prophylaxis of the specific disorder or condition, or alleviation of the symptoms associated with a specific disorder or condition or preventing or eliminating said symptoms.

The disclosed compounds are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours, "rt" for room temperature, and "rac" for racemic mixture).

The values listed below for radicals, substituents, and ranges, are for illustration only; they do not exclude other defined values or other values within defined ranges for the radicals and substituents. The disclosed compounds include compounds of formula I having any combination of the values, specific values, more specific values, and preferred values described herein.

The term "halogen" or "halo" includes bromo, chloro, fluoro, and iodo. The term "haloalkyl", refers to an alkyl radical bearing at least one halogen substituent, non-limiting examples include, but are not limited to, chloromethyl, fluoroethyl or trifluoromethyl and the like. The term "$C_1$-$C_{24}$ alkyl" refers to a branched or linear alkyl group having from one to nine carbons. Non-limiting examples include, but are not limited to, methyl, ethyl, n-propyl, iso-propyl, butyl, iso-butyl, sec-butyl, tert-butyl, pentyl, hexyl, heptyl, octyl and the like. The term "$C_2$-$C_{24}$ alkenyl", refers to an olefinically unsaturated branched or linear group having from two to nine carbon atoms and at least one double bond. Typically, $C_2$-$C_{24}$ alkenyl groups include, but are not limited to, 1-propenyl, 2-propenyl, 1,3-butadienyl, 1-butenyl, hexenyl, pentenyl, hexenyl, heptenyl, octenyl and the like. The term ($C_2$-$C_{24}$) alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl, and the like. The term "($C_1$-$C_{24}$)alkoxy or alkoxyl" refers to an alkyl group attached through an oxygen atom. Examples of ($C_1$-$C_{24}$)alkoxy can be methoxy, ethoxy, propoxy, isopropoxy, butoxy, iso-butoxy, sec-butoxy, pentoxy, 3-pentoxy, or hexyloxy and the like. The term; ($C_2$-$C_{26}$) alkoxyalkyl can be methoxy methyl, methoxy ethyl, ethoxy methyl, ethoxy ethyl, and the like.

The term "$C_3$-$C_{12}$ cycloalkyl", can be cyclopropyl, cyclobutyl, cyclopentyl, cyclohexyl, cycloheptyl, cyclooctyl and the like.

The term "optionally substituted" refers to zero, one, two, three or four substituents, wherein the substituents are each independently selected. Each of the independently selected substituents may be the same or different than other substituents.

The term "($C_6$-$C_{10}$)aryl" refers to a mono or bicyclic carbocyclic ring system having one or two aromatic rings including, but not limited to, phenyl, benzyl, naphthyl, tetrahydronaphthyl, indanyl, indenyl, and the like.

The term "($C_6$-$C_{10}$)aryl($C_1$-$C_{24}$)alkyl" or "aralkyl" refers to an alkyl group substituted with a mono or bicyclic carbocyclic ring system having one or two aromatic rings including, a group such as phenyl, naphthyl, tetrahydronaphthyl, indanyl, indenyl, and the like. Non-limiting examples of arylalkyl include benzyl, phenylethyl, naphthylmethyl and the like.

The term "($C_1$-$C_{24}$)alkyl($C_6$-$C_{10}$)aryl" refers to any aryl group that is attached to the parent moiety via the alkyl group, and the term "($C_1$-$C_{24}$)alkyl($C_6$-$C_{10}$)aryl" to an aromatic ring that is attached to the parent moiety via an alkyl group.

The term "optionally substituted aryl" includes aryl compounds having zero, one, two, three or four substituents, and a substituted aryl includes aryl compounds having one, two, three or four substituents, wherein the substituents include groups such as, for example, alkyl, halo, or amino substituents.

The "($C_2$-$C_{10}$)heterocyclic group" refers to an optionally substituted mono- or bicyclic carbocyclic ring system containing one, two, or three heteroatoms (optionally in each ring) wherein the heteroatoms are oxygen, sulfur, and nitrogen.

The term "($C_4$-$C_{10}$)heteroaryl" refers to an optionally substituted mono- or bicyclic carbocyclic ring system containing one, two, or three heteroatoms (optionally in each ring) wherein the heteroatoms are oxygen, sulfur, and nitrogen. Non-limiting examples of heteroaryl groups include furyl, thienyl, pyridyl, and the like.

The term "bicyclic" represents either an unsaturated or saturated stable bridged or fused bicyclic carbon ring. The bicyclic ring may be attached at any carbon atom which affords a stable structure. Typically a bicyclic ring system can have from about 7- to about 12 atoms in the ring system. The term includes, but is not limited to, naphthyl, dicyclohexyl, dicyclohexenyl, and the like.

The term "phosphate analog", "phosphate ester", "phosphonate ester" and "phosphonate analog" comprise analogs of phosphate and phosphonate wherein the phosphorous atom is in the +5 oxidation state and one or more of the oxygen atoms is replaced with a non-oxygen moiety, including for example, the phosphate analogs phosphorothioate, phosphorodithioate, phosphoroselenoate, phosphorodiselenoate, phosphoroanilothioate, phosphoranilidate, phosphoramidate, boronophosphates, and the like, including associated counterions, e.g., H, $NH_4$, Na, K, and the like if such counterions are present.

A "derivative" of a compound refers to a chemical compound that may be produced from another compound of similar structure in one or more steps, such as replacement of hydrogen by an alkyl, acyl, or amino group.

The term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "pharmaceutically-acceptable salt" refers to salts that retain the biological effectiveness and properties of the disclosed compounds and that are not biologically or otherwise undesirable. In many cases, the disclosed compounds are capable of forming acid or base salts by virtue of the presence of amino or carboxyl groups or groups similar thereto.

An "effective amount" means an amount sufficient to produce a selected effect. For example, an effective amount of an LPA receptor agonist is an amount that decreases the cell signaling activity of the LPA receptor.

The disclosed compounds may exist in tautomeric forms and the invention includes both mixtures and separate individual tautomers. For example, the following structure:

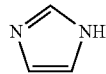

is understood to represent a mixture of the structures:

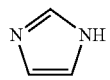

as well as

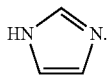

The terms 16:0, 18:0, 18:1, 20:4 or 22:6 hydrocarbon refers to a branched or straight alkyl or alkenyl group, wherein the first integer represents the total number of carbons in the group and the second integer represent the number of double bonds in the group.

An "LPA modulating agent" refers a compound or composition that is capable of inducing a detectable change in LPA receptor activity in vivo or in vitro (e.g., at least 10% increase or decrease in LPA activity as measured by a given assay such as the bioassay described in the examples and known in the art. "LPA receptor," refers to all of the LPA receptor subtypes (for example, the LPA receptors $LPA_1$, $LPA_2$, and $LPA_3$), unless the specific subtype is indicated.

The disclosed compounds can contain one or more asymmetric centers in the molecule. In accordance with the present disclosure any structure that does not designate the stereochemistry is to be understood as embracing all the various optical isomers, as well as racemic mixtures thereof.

It will be appreciated by those skilled in the art that the disclosed compounds having chiral centers may exist in and be isolated in optically active and racemic forms. It is to be understood that the disclosed compounds encompass any racemic, optically active or stereoisomeric form, or mixtures thereof, of the compound, which possess the useful properties described herein, such as the S,R; S,S; R,R; or R,S diastereomers. It is well known in the art how to prepare such optically active forms (for example, by resolution of the racemic form by recrystallization techniques, by synthesis from optically-active starting materials, by chiral synthesis, or by chromatographic separation using a chiral stationary phase) and how to determine LPA agonist activity using the standard tests described herein, or using other similar tests which are well known in the art. In addition, some compounds may exhibit polymorphism.

Neuropathic pain is characterized by its chronic nature, an absence of an obvious, direct cause (e.g., tissue damage), hyperalgesia or allodynia. Hyperalgesia is an exaggerated response to a painful stimulus. Allodynia is the perception of normal stimuli as painful (examples include the touch of clothing, warm or cool air, etc.). Neuropathic pain can be a sequel to nerve damage in an extremity such as an arm, or more often a leg. Precipitating events can include trauma, e.g., motor vehicle accidents or amputations (e.g., phantom limb pain). Neuropathic pain can occur due to an adverse effect of drug therapies, e.g., vincristine or paclitaxel (TAXOL™) or can occur as a component of disease pathologies, such as diabetes type 1 or type2, shingles, HIV-1 infections, etc. Typically, neuropathic pain is not responsive to opiates or non-steroidal anti-inflammatory drugs such as aspirin.

In another aspect, the present invention provides compositions and methods for the use of the LPA analogs of the invention to prevent, inhibit, or treat neuropathic pain by agonizing or antagonizing the LPA receptors. Pain can be nociceptive or neuropathic in nature. Neuropathic pain is characterized by its chronic nature, an absence of an obvious, direct cause (i.e., tissue damage), and allodynia. Allodynia is the perception of normal stimuli as painful (examples include the touch of clothing, warm or cool air, etc.). Neuropathic pain is often a sequel to nerve damage in an extremity such as an arm, or more often, a leg. Typically, neuropathic pain is not responsive to opiates or non-steroidal anti-inflammatory drugs such as aspirin.

In another aspect, the present invention provides compositions and methods for the use of LPA analogs and LPA prodrugs for the treatment of neoplastic disease. In one aspect, this treatment is effected by application of LPA receptor antagonists that are efficacious by virtue of their anti-angiogenic properties. In another aspect, the treatment is effected by administration of sphingosine analogs that inhibit the multiple substrate lipid kinase.

The present invention is also includes pharmaceutical compositions including the compounds of the present invention. More particularly, such compounds can be formulated as pharmaceutical compositions using standard pharmaceutically acceptable carriers, fillers, solubilizing agents and stabilizers known to those skilled in the art. For example, a pharmaceutical composition having a compound of the invention, or analog, derivative, or modification thereof, as described herein, is used to administer the appropriate compound to a subject.

The compounds of the invention are useful for treating a disease or disorder including administering to a subject in need thereof of a therapeutically acceptable amount of a compound of formula I, or a pharmaceutical composition including a therapeutically effective amount of a compound of formula I, and a pharmaceutically-acceptable carrier.

The present invention is directed to lysophosphatidic acid (LPA) analogs that have activity as receptor antagonists at one or more LPA receptors, specifically $LPA_1$, $LPA_2$, and $LPA_3$ receptor types. The invention includes both compounds that have a phosphate moiety as well as compounds with hydrolysis-resistant phosphate surrogates such as phosphonates, alpha-substituted phosphonates particularly where the alpha substitution is a halogen and phosphothionates.

Specific and preferred values listed below for radicals, substituents, and ranges, are for illustration only; they do not exclude other defined values or other values within defined ranges for the radicals and substituents.

An exemplary value for Z is —CY═CH—.

Another exemplary value for wherein Z is —C≡C—.

An exemplary value for Y is hydrogen, fluorine, chlorine or bromine.

Another exemplary value for Y is hydrogen or fluorine.

Another exemplary value for Y is hydrogen.

Another exemplary value for Y is fluorine.

Exemplary values for $R^1$ include fluorine, chlorine, bromine, trifluoro-methyl, methoxy, $(C_1\text{-}C_6)$alkyl, $(C_1\text{-}C_6)$haloalkyl, or $(C_1\text{-}C_6)$alkyl substituted with, alkoxy or cyano.

Additional exemplary values for $R^1$ include fluorine, trifluoromethyl, trifluoromethoxy, 1,1,1-trifluoroethyl, 1,1,1-trifluoroethoxy, methoxy, or ethoxy.

Exemplary values for $R^3$ include fluorine, chlorine, bromine, trifluoro-methyl, methoxy, $(C_1\text{-}C_6)$alkyl, $(C_1\text{-}C_6)$haloalkyl, or $(C_1\text{-}C_6)$alkyl substituted with, alkoxy or cyano.

Additional exemplary values for $R^3$ include fluorine, trifluoromethyl, trifluoromethoxy, 1,1,1-trifluoroethyl, 1,1,1-trifluoroethoxy, methoxy, or ethoxy.

Exemplary values for $R^4$ include alkyl, or alkenyl.

Exemplary values for $R^2$ include hydrogen, methyl, ethyl, fluoro, chloro, trifluoromethyl, trifluoromethoxy, 1,1,1-trifluoroethyl, 1,1,1-trifluoroethoxy, methoxy, ethoxy, propoxy, butoxy, and pentoxy.

Exemplary values for $R^2$ include hydrogen, trifluoromethyl, trifluoromethoxy, 1,1,1-trifluoroethyl, and 1,1,1-trifluoroethoxy.

Additional exemplary values for $R^2$ include hydrogen, trifluoromethoxy, and 1,1,1-trifluoroethoxy.

Additional exemplary values for $R^4$ include $C_5H_{11}$, $C_6H_{13}$, $C_7H_{14}CH$═$CHC_8H_{17}$ and $C_{15}H_{31}$.

Additional exemplary values for $R^4$ include $C_7H_{14}CH$═$CHC_8H_{17}$ and $C_{15}H_{31}$.

Exemplary values for $R^5$, and $R^6$, include trifluoromethoxy, 1,1,1-trifluoroethoxy, methoxy, and ethoxy.

Additional exemplary values for $R^5$ and $R^6$ include hydroxy, methoxy, and ethoxy.

Values for $R^3$ include methyl, hydroxymethyl, ethyl, hydroxyethyl, propyl, hydroxypropyl, or isopropyl.

Additional values for $R^3$ are methyl, hydroxymethyl, ethyl, or hydroxyethyl.

Values for $R^4$ include is hydroxy, or phosphate (—$OPO_3H_2$).

Specific compounds of the invention have the general formula IA and are illustrated in table 1, below.

TABLE 1

IA

| VPC | Compound | $Z^1$ | $Y^1$ | $R^1$ | $R^4$ | R/S |
|---|---|---|---|---|---|---|
| 32210 | 1a | $CH_2OPO_3H$ | $CH_3$ | $CH_3$ | $C_7H_{14}CH$═$CHC_8H_{17}$ | R |
| 51098 | 1b | $CH_2OPO_3H$ | $CH_2CF_3$ | H | $C_7H_{14}CH$═$CHC_8H_{17}$ | R |
| 51156 | 1c | $CH_2OPO_3H$ | $(CH_2)_4CH_3$ | H | $C_7H_{14}CH$═$CHC_8H_{17}$ | R |
| 32301 | 1d | $CH_2CH_2PO_3H$ | $CH_3$ | $CH_3$ | $C_7H_{14}CH$═$CHC_8H_{17}$ | R |
| 51304 | 7a | $CH$═$CHPO_3H$ | $CH_3$ | $CH_3$ | $C_{15}H_{31}$ | R |
| 51299 | 7b | $CH$═$CHPO_3H$ | $CH_2CF_3$ | H | $C_{15}H_{31}$ | R |
| 52156 | 7c | $CH$═$CHPO_3H$ | $CH_2CF_3$ | H | $C_{15}H_{31}$ | S |
| 52071 | 7d | $CH$═$CHPO_3H$ | $(CH_2)_4CH_3$ | H | $C_{15}H_{31}$ | R |
| 52007 | 7e | $CH_2CH_2PO_3H$ | $CH_3$ | $CH_3$ | $C_{15}H_{31}$ | R |
| 51303 | 7f | $CH_2CH_2PO_3H$ | $CH_2CF_3$ | H | $C_{15}H_{31}$ | R |
| 52162 | 7g | $CH_2CH_2PO_3H$ | $CH_2CF_3$ | H | $C_{15}H_{31}$ | S |
| 8a270 | 7h | $CH$═$CFPO_3H$ | $CH_3$ | $CH_3$ | $C_{15}H_{31}$ | R |
| 52289 | 7i | $CH$═$CFPO_3H$ | $CH_2CF_3$ | H | $C_{15}H_{31}$ | R |
| 52300 | 7j | $CH$═$CFPO_3H$ | $CH_2CF_3$ | H | $C_{15}H_{31}$ | S |
| 8a248 | 7k | $CH_2CHFPO_3H$ | $CH_3$ | $CH_3$ | $C_{15}H_{31}$ | R |
| 8a250 | 7l | $CH_2CHFPO_3H$ | $CH_3$ | $CH_3$ | $C_{15}H_{31}$ | R |
| 52293 | 7m | $CH_2CHFPO_3H$ | $CH_2CF_3$ | H | $C_{15}H_{31}$ | R |
| 52294 | 7n | $CH_2CHFPO_3H$ | $CH_2CF_3$ | H | $C_{15}H_{31}$ | R |
| 103125 | 7o | $CH_2CHFPO_3H$ | $CH_2CF_3$ | H | $C_{15}H_{31}$ | S |
| 103127 | 7p | $CH_2CHFPO_3H$ | $CH_2CF_3$ | H | $C_{15}H_{31}$ | S |

TABLE 1-continued

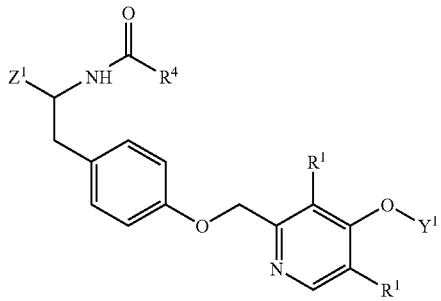

| VPC | Compound | $Z^1$ | $Y^1$ | $R^1$ | $R^4$ | R/S |
|---|---|---|---|---|---|---|
| 52217 | 12 | CH=CHCO$_2$H | CH$_2$CF$_3$ | H | C$_{15}$H$_{31}$ | R |
| 52226 | 13 | CH=CHSO$_3$H | CH$_2$CF$_3$ | H | C$_{15}$H$_{31}$ | R |
| 8a089 | 18a | CH$_2$CHOHPO$_3$H | CH$_3$ | CH$_3$ | C$_{15}$H$_{31}$ | S,R |
| 8a157 | 18b | CH$_2$CHOHPO$_3$H | CH$_3$ | CH$_3$ | C$_{15}$H$_{31}$ | R,R |
| 8a137 | 18c | CH$_2$CHOHPO$_3$H | CH$_3$ | CH$_3$ | C$_{15}$H$_{31}$ | S,S |
| 8a120 | 18d | CH$_2$CHOHPO$_3$H | CH$_3$ | CH$_3$ | C$_{15}$H$_{31}$ | R,S |
| 53012 | 18e | CH$_2$CHOHPO$_3$H | CH$_2$CF$_3$ | H | C$_{15}$H$_{31}$ | R,R |
| 53016 | 18f | CH$_2$CHOHPO$_3$H | CH$_2$CF$_3$ | H | C$_{15}$H$_{31}$ | R,S |
| 53018 | 18g | CH$_2$CHOHPO$_3$H | CH$_2$CF$_3$ | H | C$_{15}$H$_{31}$ | S,R |
| 53019 | 18h | CH$_2$CHOHPO$_3$H | CH$_2$CF$_3$ | H | C$_{15}$H$_{31}$ | S,S |

Without wishing to be bound by any particular theory, it is expected that the compounds described herein are pro-drugs, e.g. are activated by phosphorylation of the primary alcohol to form the mono-phosphorylated analog. Additionally, the active drugs are expected to be antagonists at the LPA type 1 receptor.

In cases where compounds of formula I are sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically acceptable base addition salts can be prepared from inorganic and organic bases. Salts from inorganic bases, include but are not limited to, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included are amines where the two or three substituents, together with the amino nitrogen, form a heterocyclic or heteroaryl group. Non-limiting examples of amines include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

The compounds of formula I can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Exemplary pharmaceutical dosage forms for injection or infusion can include sterile aqueous solutions or dispersions or sterile powders having the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium including, for example, water, ethanol, a polyol (for example, glycerol, propylene glycol, liquid polyethylene glycols, and the like), vegetable oils, nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Exemplary solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1 to about 25 weight percent, preferably from about 0.5-10 weight percent. The concentration in a semi-solid or solid composition such as a gel or a powder will be about 0.1-5 weight percent preferably about 0.5-2.5 weight percent based on the total weight of the composition.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu M$, preferably, about 1 to 50 $\mu M$, most preferably, about 2 to about 30 $\mu M$. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method includes a kit including an inhibitor compound of formula I and instructional material that describes administering the inhibitor compound or a composition including the inhibitor compound to a cell or a subject. This should be construed to include other embodiments of kits that are known to those skilled in the art, such as a kit having a (preferably sterile) solvent for dissolving or suspending the inhibitor compound or composition prior to administering the compound or composition to a cell or a subject. Preferably, the subject is a human.

The disclosed compounds and methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the disclosed compounds.

Figure 1B:
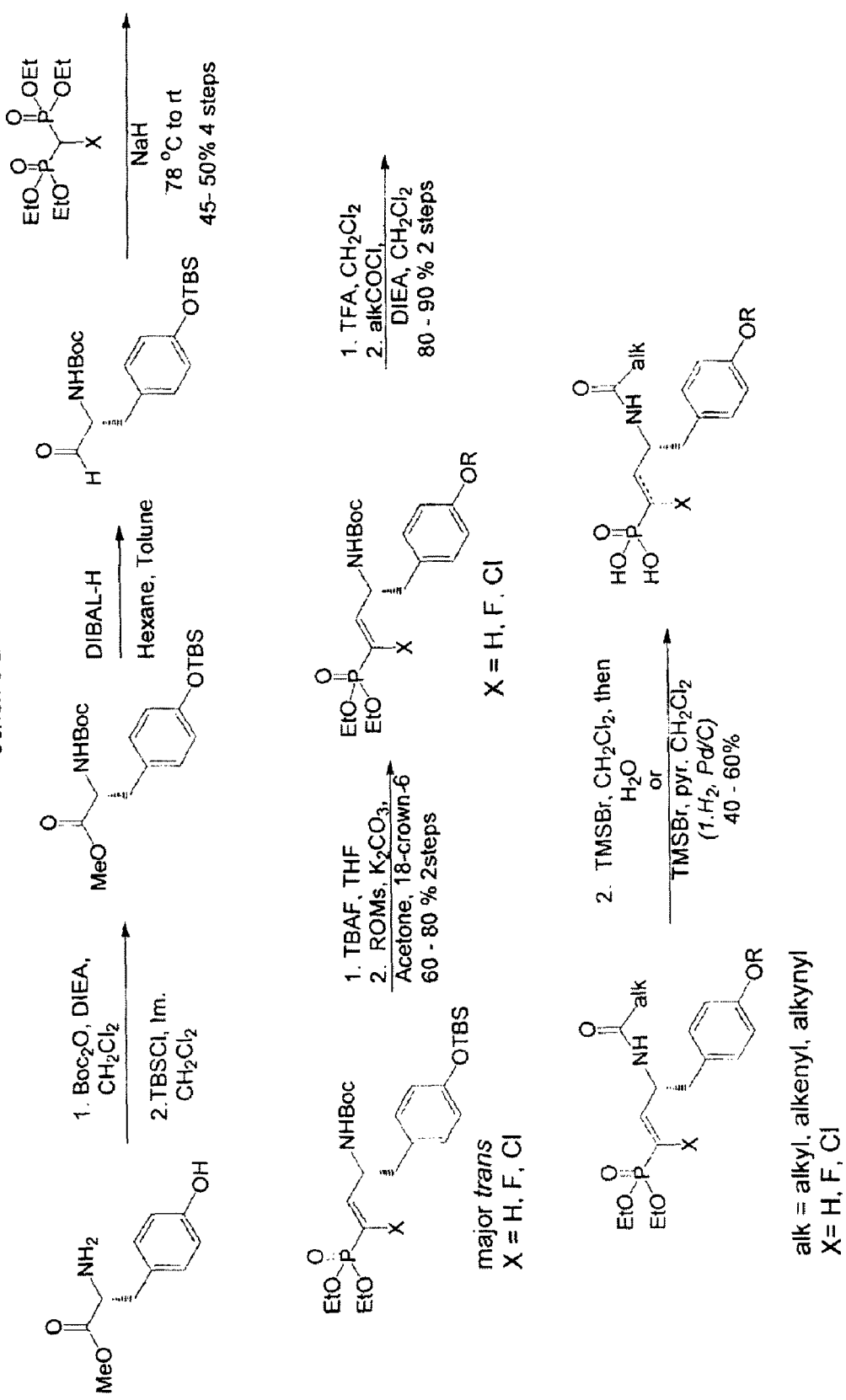

Processes for preparing compounds of formula I or for preparing intermediates useful for preparing compounds of formula I are provided as further embodiments. Intermediates useful for preparing compounds of formula I are also provided as further embodiments. The processes are provided as further embodiments and are illustrated in the schemes herein wherein the meanings of the generic radicals are as given above unless otherwise qualified. A general method for preparing the disclosed compounds is illustrated in Scheme 1 and Scheme 2, illustrated in FIGS. 1A and 1B, respectively.

The invention is now described with reference to the following Examples and Embodiments. Without further description, it is believed that one of ordinary skill in the art can, using the preceding description and the following illustrative examples, make and utilize the disclosed compounds. The following working examples therefore, are provided for the purpose of illustration only and specifically point out the preferred embodiments, and are not to be construed as limiting in any way the remainder of the disclosure. Therefore, the examples should be construed to encompass any and all variations which become evident as a result of the teaching provided herein.

Materials. Chemicals for synthesis were purchased from Aldrich Chemical Company (Milwaukee, Wis.), Sigma Chemicals (St. Louis, Mo.), and/or NovaBiochem Chemical Company (Laufelfingen, Switzerland) and were of highest quality available and used without further purification. All reactions were carried out under an inert atmosphere of nitrogen unless otherwise stated. All solvents were filtered through Alumina (Activity 1) prior to use in reactions. Merck silica gel F-254 pre-coated, aluminum backed plates were used for Thin later chromatography (TLC). Merck Silica Gel 6 (230-400 mesh) or Silicycle Ultra Pure Silica Gel (230-400 mesh) was used for column chromatography. Nuclear magnetic resonance spectra were collected using a Varian Unity spectrometer at 300 MHz and chemical shifts are reported in ppm and coupling constant, J, is reported in Hz. Mass spectrometry was collected using a Finnigan (model LCQ Classic) quadrupole ion trap mass spectrometer.

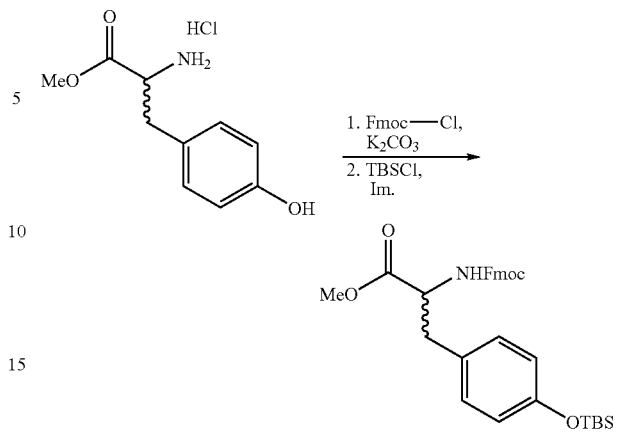

EXAMPLE 1

N-Fmoc, O-TBS, Tyrosine OMe

To tyrosine OMe ester hydrochloride (5 g, 21.6 mmol) in $H_2O$ (20 ml) is added $K_2CO_3$ (5.97 g, 43.2 mmol) in $H_2O$ (10 ml) at 0° C. The precipitate is dissolved in dioxane (40 ml) and FmocCl is added in small portions. The cloudy mixture is stirred at 0° C. for 4 hours until completion as judged by TLC (4:1 Hexane:EtOAc). The reaction is extracted with EtOAc, dried over $MgSO_4$, and evaporated. The crude O-Fmoc protected tyrosine and imidazole (4.4 g, 64.7 mmol) are dissolved in anhydrous $CH_2Cl_2$ (50 ml). TBSCl (8.13 g, 54.0 mmol) in anhydrous $CH_2Cl_2$ (20 ml) is added at 0° C. The mixture is stirred at room temperature for 4 hours until completion as judged by TLC (4:1 Hexane:EtOAc). The mixture is extracted with $Et_2O$, dried over $MgSO_4$, and the solvent evaporated under reduced pressure. Flash chromatography provided the product as a white solid (10.55 g, 86.5% yield). Rf ($SiO_2$, 15% ethyl acetate in hexanes)=0.25.

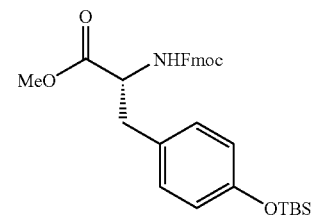

EXAMPLE 2

(2-R)-3-[4-(tert-Butyl-dimethyl-silanyloxy)-phenyl]-2-(9H-fluoren-9-ylmethoxycarbonylamino)-propionic Acid Methyl Ester $^1$H NMR (300 MHz, $CDCl_3$) δ=0.19 (s, 6H), 1.00 (s, 9H), 3.06 (t, 2H, J=5.6), 3.71 (s, 3H), 4.21 (t, 2H, J=7.0), 4.31-4.49 (m, 2H), 4.65 (dd, 1H, J=13.9, 7.9), 5.39 (t, 1H, J=6.6), 6.77 (d, 2H, J=8.1), 6.97 (d, 2H, J=8.1), 7.32 (t, 2H, J=7.5), 7.41 (t, 2H, J=7.5), 7.58 (dd, 2H, J=2.6, 6.9), 7.77 (d, 2H, J=7.5). $^{13}$C NMR (300 MHz, $CDCl_3$) δ=−4.54, 18.05, 25.56, 37.36, 47.06, 52.13, 54.83, 66.80, 119.87, 120.05, 125.02, 124.94, 126.95, 127.59, 128.28, 130.18, 141.21, 143.66, 143.77, 154.67, 155.47, 171.95. MS (ESI) m/z=532.0 (M+H)$^+$, 100%).

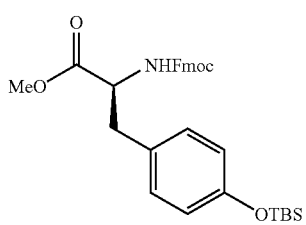

EXAMPLE 3

(2-S)-3-[4-(tert-Butyl-dimethyl-silanyloxy)-phenyl]-2-(9H-fluoren-9-ylmethoxycarbonylamino)-propionic Acid Methyl Ester This product has similar spectral properties as its enantiomer.

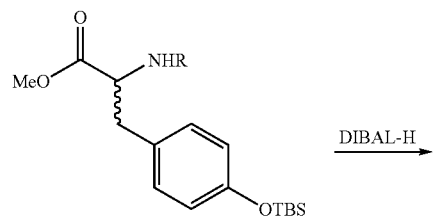

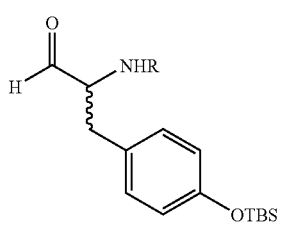

R = Boc, Fmoc

EXAMPLE 4

N-Boc or N-Fmoc, O-TBS, Tyrosinal

N-Boc or N-Fmoc, O-TBS, tyrosine OMe (10.2 mmol) in anhydrous toluene (100 ml), cooled to −78° C. is added DIBAL-H (1M in hexanes, 30.5 ml, 30.5 mmol) over 45 minutes via cannulation. The reaction is stirred an additional 5 minutes and quenched with MeOH. The mixture is removed from cooling bath, saturated aqueous Rochelle's salt (150 ml) is added and the mixture stirred vigorously for 1.5 hours or until the phases become clear. The mixture is extracted with ether, and the ethereal extract is washed with brine, dried over MgSO$_4$), and concentrated under reduced pressure to give the aldehyde as a glassy solid which is used without further purification.

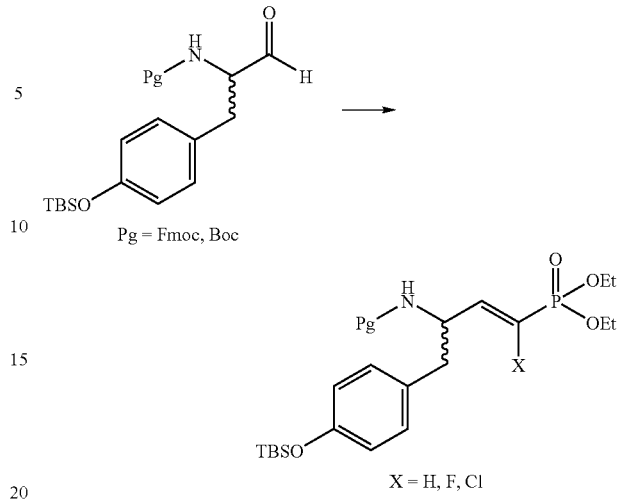

Pg = Fmoc, Boc

X = H, F, Cl

EXAMPLE 5

[4-[4-(tert-Butyl-dimethyl-silanyloxy)-phenyl]-3-(9H-fluoren-9-ylmethoxycarbonylamino)-trans-but-1-enyl]-phosphonic Acid Diethyl Ester or [4-[4-(tert-Butyl-dimethyl-silanyloxy)-phenyl]-3-(tert-butoxycarbonylamino)-trans-but-1-enyl]-phosphonic Acid Diethyl Ester Method A. To a solution of N-PG, O-TBS tyrosinal, (10 mmol) in anhydrous toluene is added [(diethoxyphosphinyl)methylidene]triphenylphosphirane following the method of Xu, Y. et al., *J. Organic Chemistry*, 1996, 61, 7697-7701 (15 mmol) at room temperature under N$_2$. The mixture is heated to 100° C. for 16 h. or until completion as judged by TLC (1:1 Hexane:EtOAc). Upon completion, the solvents were removed under reduced pressure, and the residue subject to flash chromatography (1:1 Hexane:EtOAc to 100% EtOAc) to afford the product as a pale yellow oil (66% yield). Rf (SiO$_2$, EtOAc)=0.61.

Method B. To a solution of NaH (60% in mineral oil, 375 mg, 9.4 mmol) in THF (15 ml) at 0° C. is added the appropriate tetra-ethyl diphosphonate (9.4 mmol) in THF (15 ml) via cannulation. The mixture is stirred at 0° C. for 30 min and the aldehyde, dissolved in THF (25 ml), is added via cannulation. The mixture is allowed to stir an additional 30 minutes at 0° C. Excess NaH is consumed with saturated aqueous ammonium chloride, and the aqueous layer is extracted with Ethyl Acetate. The organic layer is washed with brine, dried (MgSO$_4$), evaporated to dryness, and subject to flash:chromatography (1:1 Hexane:EtOAc to 100% EtOAc) to afford the product as a pale yellow oil (43% yield). Rf (SiO$_2$, EtOAc)= 0.61.

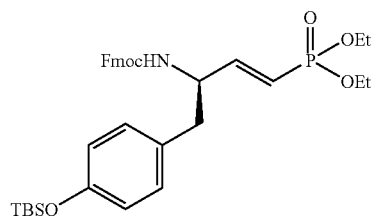

EXAMPLE 6

(3R)-[4-[4-(tert-Butyl-dimethyl-silanyloxy)-phenyl]-3-(9H-fluoren-9-ylmethoxycarbonylamino)-trans-but-1-enyl]-phosphonic Acid Diethyl Ester $^1$H NMR (300 MHz, CDCl$_3$) δ=0.16 (s, 6H), 0.97 (s, 9H), 1.28 (q, 6H, J=8.8, 7.1), 2.83 (d, 2H, J=6.1), 3.92-4.05 (m, 4H), 4.17 (t, 2H, J=7.0), 4.25-4.46 (m, 2H), 4.52-4.66 (m, 1H), 5.03-5.19 (m, 1H), 5.67 (apparent t, 1H, J=18.0), 6.64-6.81 (m, 3H), 6.99 (d, 2H, J=7.7), 7.33 (d, 2H, J=7.3), 7.38 (d, 2H, J=7.5), 7.53 (dd, 2H, J=2.9, 7.0), 7.75 (d, 2H, J=7.5). $^{13}$C NMR (300 MHz, CDCl$_3$) δ=−4.62, 16.16 (d, $^3J_{C,P}$=6.0 Hz), 17.97, 25.48, 39.58, 47.03, 54.02 (d, $^3J_{C,P}$=24.2 Hz), 61.59 (d, $^2J_{C,P}$=6.0 Hz), 66.56, 117.13 (d, $^1J_{C,P}$=186.7 Hz), 119.81, 119.95, 124.81, 124.89, 126.92, 127.56, 130.20, 141.15, 143.64, 151.32 (d, $^2J_{C,P}$=6.0 Hz), 151.38, 154.46, 155.39, 169.49. MS (ESI) m/z=636.7 ((M+H)$^+$, 100%).

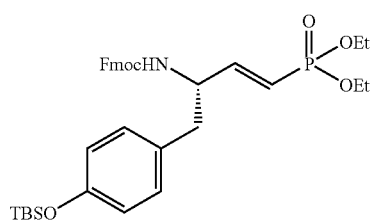

EXAMPLE 7

(3S)-[4-[4-(tert-Butyl-dimethyl-silanyloxy)-phenyl]-3-(9H-fluoren-9-ylmethoxycarbonylamino)-trans-but-1-enyl]-diethyl Phosphonate This product has similar spectral properties as its enantiomer.

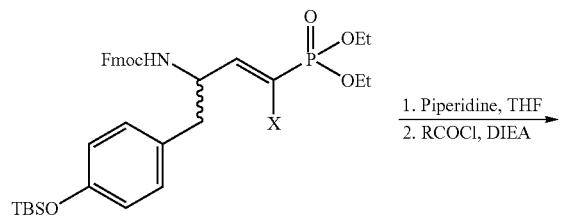

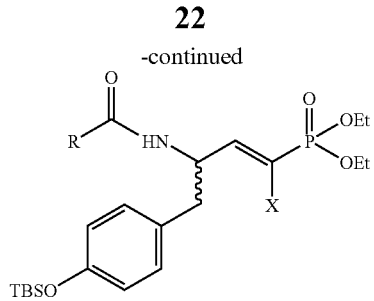

X = H, F, Cl

EXAMPLE 8

General Procedure for Fmoc Deprotection and Acylation. Synthesis of {4-[4-(tert-Butyl-dimethyl-silanyloxy)-phenyl]-3-acylamino-trans-but-1-enyl}-diethyl Phosphonates To [4-[4-(O-TBS)-phenyl]-3-(N-Fmoc)-trans-but-1-enyl]-diethyl phosphonate (1.3 g, 2.0 mmol) in DMF (10 ml) is added piperidine (10.0 mmol, 1 ml). The solution is stirred at room temperature under N$_2$ for 15 min. then evaporated to dryness to afford the free amine. To the amine dissolved in CH$_2$Cl$_2$ (50 ml) is added Hünigs base (6.0 mmol, 1.1 ml) and acid chloride (2.4 mmol) and the mixture stirred at room temperature under N$_2$. On completion, as judged by TLC, the solvent is evaporated under reduced pressure, and the residue subject to flash chromatography to afford the product as yellow oil (60-80% yield).

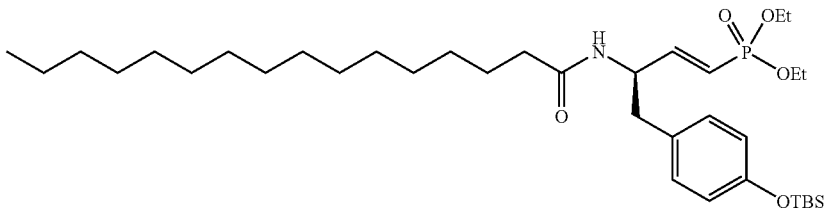

EXAMPLE 9

(3R)-{4-[4-(tert-Butyl-dimethyl-silanyloxy)-phenyl]-3-hexadecanoylamino-trans-but-1-enyl}-diethyl Phosphonate $^1$H NMR (300 MHz, CDCl$_3$) δ=0.14 (s, 6H), 0.84 (t, 3H, J=6.8), 0.93 (s, 9H), 1.09-1.26 (m, 30H), 1.43-1.56 (m, 2H), 2.10 (t, 2H, J=7.5), 2.79 (d, 2H, J=6.8), 3.86-4.01 (m, 4H), 4.77-4.95 (m, 1H), 5.62 (apparent t, 1H, J=19.5), 6.03 (d, 1H, J=8.4), 6.58-6.76 (m, 3H), 6.98 (d, 2H, J=8.4). $^{13}$C NMR (300 MHz, CDCl$_3$) δ=−4.54, 14.02, 16.22 (d, $^3J_{C,P}$=6.0 Hz), 18.05, 25.56, 29.19, 29.27, 29.41, 29.57, 29.62, 31.84, 36.56, 39.45, 51.91 (d, $^3J_{C,P}$=22.2 Hz), 61.76 (d, $^2J_{C,P}$=6.0 Hz), 116.91 (d, $^1J_{C,P}$=187.4 Hz), 120.00, 130.18, 132.05, 151.64 (d, $^2J_{C,P}$=6.0 Hz), 154.48, 172.56. MS (ESI) m/z=651.44 ((M+H)$^+$, 100%).

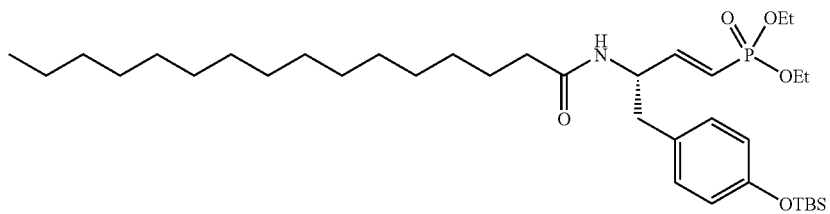

EXAMPLE 10

(3S)-{4-[4-(tert-Butyl-dimethyl-silanyloxy)-phenyl]-3-hexadecanoylamino-trans-but-1-enyl}-diethyl Phosphonate This product has similar spectral properties as its enantiomer.

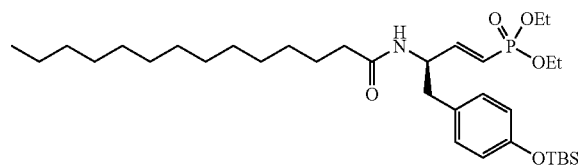

EXAMPLE 11

(3R)-{4-[4-(tert-Butyl-dimethyl-silanyloxy)-phenyl]-3-tetradecanoylamino-trans-but-1-enyl}-diethyl Phosphonate $^1$H NMR (300 MHz, CDCl$_3$) δ=0.15 (s, 6H), 0.85 (t, 3H, J=6.7), 0.95 (s, 9H), 1.15-1.29 (m, 26H), 1.46-1.59 (m, 2H), 2.11 (t, 2H, J=7.3), 2.81 (d, 2H, J=7.0), 3.88-4.06 (m, 4H), 4.81-4.94 (m, 1H), 5.60 (apparent t, 1H, J=199.1), 5.84 (d, 1H, J=8.6), 6.60-6.77 (m, 3H), 6.99 (d, 2H, J=8.4). $^{13}$C NMR (300 MHz, CDCl$_3$) δ=-4.52, 14.05, 16.25 (d, $^3J_{C,P}$=6.0 Hz), 18.08, 22.62, 25.56, 25.64, 29.19, 29.30, 29.43, 29.59, 31.86, 36.62, 39.42, 51.85 (d, $^3J_{C,P}$=22.2 Hz), 61.74 (t, $^2J_{C,P}$=6.0 Hz), 116.94 (d, $^1J_{C,P}$=187.4 Hz), 120.05, 128.92, 130.20, 151.61 (d, $^2J_{C,P}$=6.0 Hz), 154.51, 172.56MS (ESI) m/z=623.41 ((M+H)$^+$, 100%).

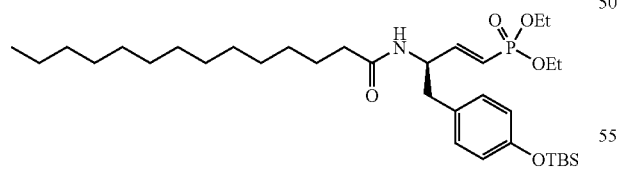

EXAMPLE 12

(3S)-{4-[4-(tert-Butyl-dimethyl-silanyloxy)-phenyl]-3-tetradecanoylamino-trans-but-1-enyl}-diethyl Phosphonate This product has similar spectral properties as its enantiomer.

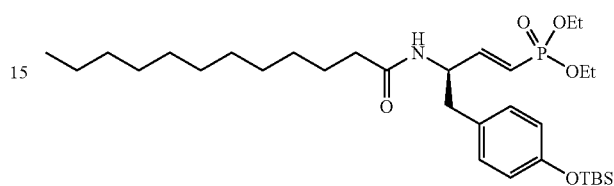

EXAMPLE 13

(3R)-{4-[4-(tert-Butyl-dimethyl-silanyloxy)-phenyl]-3-dodecanoylamino-trans-but-1-enyl}-diethyl Phosphonate $^1$H NMR (300 MHz, CDCl$_3$) δ=0.13 (s, 6H), 0.82 (t, 3H, J=7.0), 0.92 (s, 9H), 1.14-1.34 (m, 22H), 1.45-1.57 (m, 2H), 2.10 (t, 2H, J=7.4), 2.78 (d, 2H, J=7.0), 3.87-4.09 (m, 4H), 4.76-4.95 (m, 1H), 5.62 (apparent t, 1H, J=18.4), 6.20 (d, 1H, J=8.6), 6.57-6.78 (m, 3H), 6.98 (d, 2H, J=8.4). $^{13}$C NMR (300 MHz, CDCl$_3$) δ=-4.60, 13.97, 16.17 (d, $^3J_{C,P}$=6.0 Hz), 18.00, 22.54, 25.51, 29.14, 29.19, 29.35, 29.46, 29.51, 31.76, 36.48, 39.39, 51.94 (d, $^3J_{C,P}$=22.2 Hz), 61.70 (d, $^2J_{C,P}$=6.0 Hz), 116.74 (d, $^1J_{C,P}$=185.4 Hz), 119.92, 128.31, 130.12, 131.86, 151.66 (d, $^2J_{C,P}$=6.1 Hz), 154.38, 172.56.

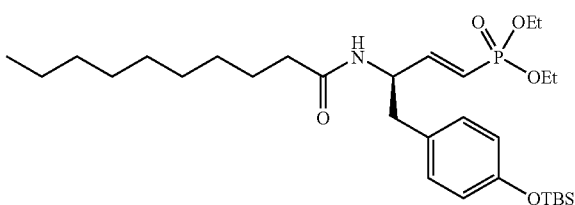

EXAMPLE 14

(3R)-{4-[4-(tert-Butyl-dimethyl-silanyloxy)-phenyl]-3-decanoylamino-trans-but-1-enyl}-diethyl Phosphonate $^1$H NMR (300 MHz, CDCl$_3$) δ=0.14 (s, 6H), 0.83 (t, 3H, J=6.4), 0.93 (s, 9H), 1.15-1.33 (m, 18H), 1.43-1.58 (m, 2H), 2.10 (t, 2H, J=7.5), 2.78 (d, 2H, J=6.6), 3.85-4.01 (m, 4H), 4.77-4.92 (m, 1H), 5.61 (apparent t, 1H, J=18.7), 6.20 (d, 1H, J=8.6), 6.56-6.78 (m, 3H), 6.98 (d, 2H, J=8.4). $^{13}$C NMR (300 MHz, CDCl$_3$) δ=-4.60, 13.91, 16.17 (d, $^3J_{C,P}$=6.0 Hz), 18.00, 22.46, 25.51, 25.59, 28.87, 29.06, 29.14, 29.22, 29.30, 31.52, 36.48, 39.37, 51.88 (d, $^3J_{C,P}$=22.2 Hz), 61.67 (t, $^2J_{C,P}$=6.0 Hz), 116.76 (d, $^1J_{C,P}$=185.3 Hz), 119.92, 128.47, 130.12, 131.86, 151.66 (d, $^2J_{C,P}$=6.0 Hz), 154.38, 172.56.

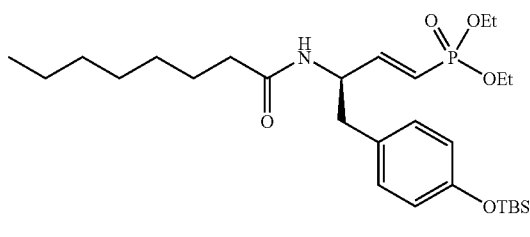
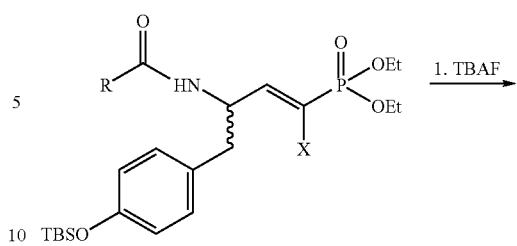 1. TBAF →

EXAMPLE 15

(3R)-{4-[4-(tert-Butyl-dimethyl-silanyloxy)-phenyl]-3-octanoylamino-trans-but-1-enyl}-diethyl Phosphonate $^1$H NMR (300 MHz, CDCl$_3$) δ=0.13 (s, 6H), 0.85 (t, 3H, J=6.4), 0.92 (s, 9H), 1.10-1.33 (m, 14H), 1.45-1.59 (m, 2H), 2.10 (t, 2H, J=7.5), 2.79 (d, 2H, J=6.7), 3.87-4.02 (m, 4H), 4.78-4.93 (m, 1H), 5.62 (apparent t, 1H, J=18.5), 6.04 (d, 1H, J=8.1), 6.59-6.77 (m, 3H), 6.99 (d, 2H, J=8.6). $^{13}$C NMR (300 MHz, CDCl$_3$) δ=−4.57, 13.99, 16.20 (d, $^3J_{C,P}$=6.0 Hz), 18.05, 22.49, 25.53, 25.61, 28.90, 29.19, 29.24, 29.32, 31.76, 36.54, 39.39, 51.88 (d, $^3J_{C,P}$=22.2 Hz), 61.70 (t, $^2J_{C,P}$=6.0 Hz), 116.84 (d, $^1J_{C,P}$=187.4 Hz), 119.97, 128.3, 130.15, 131.89, 151.64 (d, $^2J_{C,P}$=6.0 Hz), 154.43, 172.56.

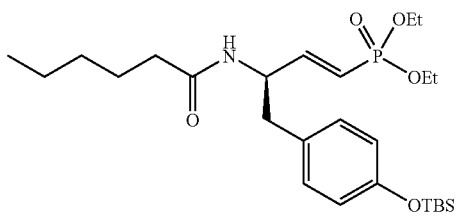

EXAMPLE 16

(3R)-{4-[4-(tert-Butyl-dimethyl-silanyloxy)-phenyl]-3-hexanoylamino-trans-but-1-enyl}-diethyl Phosphonate $^1$H NMR (300 MHz, CDCl$_3$) δ=0.13 (s, 6H), 0.83 (t, 3H, J=7.2), 0.92 (s, 9H), 1.14-1.33 (m, 10H), 1.44-1.59 (m, 2H), 2.11 (t, 2H, J=7.5), 2.79 (d, 2H, J=7.0), 3.85-4.04 (m, 4H), 4.77-4.95 (m, 1H), 5.62 (apparent t, 1H, J=18.5), 6.44 (d, 1H, J=8.1), 6.57-6.78 (m, 3H), 6.99 (d, 2H, J=8.1). $^{13}$C NMR (300 MHz, CDCl$_3$) δ=−4.60, 13.78, 16.15 (d, $^3J_{C,P}$=8.0 Hz), 18.00, 22.22, 25.27, 25.48, 31.25, 36.83, 39.42, 52.02 (d, $^3J_{C,P}$=22.2 Hz), 61.69 (t, $^2J_{C,P}$=6.0 Hz), 116.70 (d, $^1J_{C,P}$=187.4 Hz), 119.89, 128.31, 130.10, 131.83, 151.74 (d, $^2J_{C,P}$=6.0 Hz), 154.35, 172.64.

X = H, F, Cl

EXAMPLE 17

General Procedure for O-TBS Deprotection. Synthesis of 3-acylamino-4-[4-hydroxy-phenyl]-3-acyl amine-trans-but-1-enyl}-diethyl Phosphonates To {4-[4-(O-TBS)-phenyl]-3-acylamino-trans-but-1-enyl}-diethyl phosphonate (1 mmol) in THF (10 ml) is added TBAF (3 mmol) and the mixture is stirred at room temperature under N$_2$. Upon completion, as judged by TLC, the solvent is removed under reduced pressure and the residue subject to flash chromatography to afford the product as white crystals (94-100% yield).

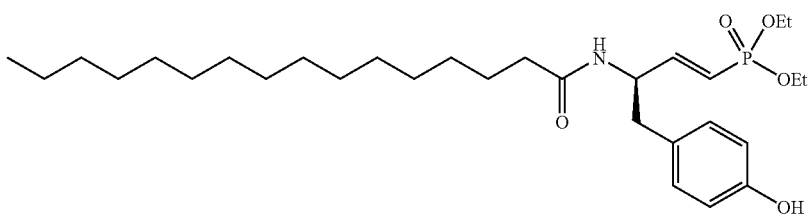

EXAMPLE 18

(3R)-[3-Hexadecanoylamino-4-(4-hydroxy-phenyl)-trans-but-1-enyl]-diethyl Phosphonate $^1$H NMR (300 MHz, CDCl$_3$) δ=0.87 (t, 3H, J=6.5), 1.15-1.36 (m, 30H), 1.49-1.64 (m, 2H), 2.15 (t, 2H, J=7.7), 2.72-

2.89 (m, 2H), 3.89-4.06 (m, 4H), 4.84-4.97 (m, 1H), 5.65 (apparent t, 1H, J=19.5), 6.03 (d, 1H, J=8.4), 6.66-6.83 (m, 3H), 6.97 (d, 2H, J=7.9). $^{13}$C NMR (300 MHz, CDCl$_3$) δ=14.07, 16.22 (d, $^3J_{C,P}$=8.1 Hz), 22.65, 25.69, 29.24, 29.46, 29.67, 31.89, 36.67, 39.58, 52.07 (d, $^3J_{C,P}$=22.2 Hz), 62.07 (q, $^2J_{C,P}$=10.1, 6.1 Hz), 116.60 (d, $^1J_{C,P}$=191.4 Hz), 115.62, 127.72, 130.28, 152.19 (d, $^2J_{C,P}$=8.1 Hz), 156.22, 172.99.

EXAMPLE 19

(3S)-[3-Hexadecanoylamino-4-(4-hydroxy-phenyl)-trans-but-1-enyl]-diethyl Phosphonate This product has similar spectral properties as its enantiomer.

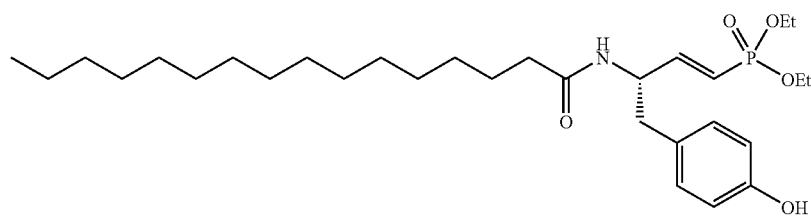

EXAMPLE 20

(3R)-[3-tetradecanoylamino-4-(4-hydroxy-phenyl)-trans-but-1-enyl]-diethyl Phosphonate $^1$H NMR (300 MHz, CDCl$_3$) δ=0.86 (t, 3H, J=6.6), 1.14-1.32 (m, 26H), 1.49-1.63 (m, 2H), 2.16 (t, 2H, J=7.6), 2.73-2.89 (m, 2H), 3.90-4.07 (m, 4H), 4.85-4.98 (m, 1H), 5.65 (apparent t, 1H, J=18.4), 5.80 (d, 1H, J=8.5), 6.66-6.84 (m, 3H), 6.97 (d, 2H, J=8.3). $^{13}$C NMR (300 MHz, CDCl$_3$) δ=14.10, 16.24 (d, $^3J_{C,P}$=8.1 Hz), 22.65, 25.69, 29.03, 29.24, 29.49, 29.62, 29.67, 31.89, 36.70, 39.58, 52.02 (d, $^3J_{C,P}$=22.2 Hz), 62.20 (q, $^2J_{C,P}$=10.0, 6.0 Hz), 115.59, 116.59 (d, $^1J_{C,P}$=189.4 Hz), 115.62, 126.68, 130.31, 152.17 (d, $^2J_{C,P}$=6.0 Hz), 156.11, 172.99. MS (ESI) m/z=510.2 ((M+H)$^+$, 100%).

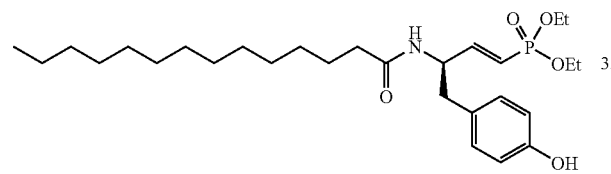

EXAMPLE 21

(3S)-[3-tetradecanoylamino-4-(4-hydroxy-phenyl)-trans-but-1-enyl]-diethyl Phosphonate This product has similar spectral properties as its enantiomer.

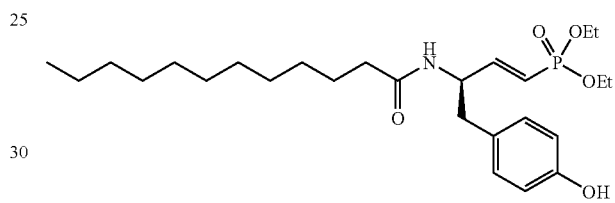

EXAMPLE 22

(3R)-[3-dodecanoylamino-4-(4-hydroxy-phenyl)-trans-but-1-enyl]-diethyl Phosphonate $^1$H NMR (300 MHz, CDCl$_3$) δ=0.83 (t, 3H, J=6.4), 1.05-1.32 (m, 22H), 1.49-1.66 (m, 2H), 2.10 (t, 2H, J=7.7), 2.69-2.86 (m, 2H), 3.87-4.04 (m, 4H), 4.78-4.96 (m, 1H), 5.61 (apparent t, 1H, J=18.3), 5.80-5.99 (bs, 1H), 6.63-6.81 (m, 3H), 6.95 (d, 2H, J=8.1). $^{13}$C NMR (300 MHz, CDCl$_3$) δ=14.05, 16.20 (d, $^3J_{C,P}$=6.1 Hz), 22.59, 25.67, 29.19, 29.27, 29.41, 29.57, 31.84, 36.62, 39.47, 52.07 (d, $^3J_{C,P}$=22.2 Hz), 62.05 (q, $^2J_{C,P}$=10.1, 6.1 Hz), 115.57, 116.47 (d, $^1J_{C,P}$=189.4 Hz), 128.60, 130.23, 152.17 (d, $^2J_{C,P}$=6.0 Hz), 156.16, 173.04.

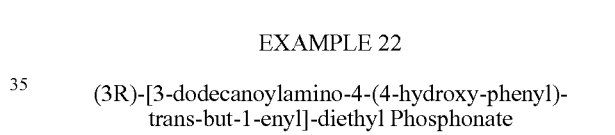

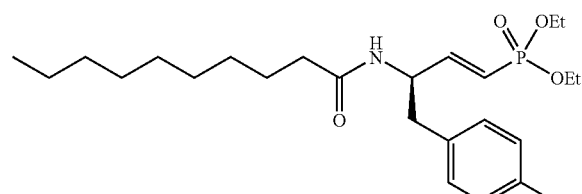

EXAMPLE 23

(3R)-[3-decanoylamino-4-(4-hydroxy-phenyl)-trans-but-1-enyl]-diethyl Phosphonate $^1$H NMR (300 MHz, CDCl$_3$) δ=0.86 (t, 3H, J=6.6), 1.19-1.32 (m, 18H), 1.49-1.61 (m, 2H), 2.15 (t, 2H, J=7.6), 2.73-2.89 (m, 2H), 3.91-4.07 (m, 4H), 4.85-4.98 (m, 1H), 5.57-5.76 (m, 2H), 6.66-6.83 (m, 3H), 6.97 (d, 2H, J=8.4). $^{13}$C NMR (300 MHz, CDCl$_3$) δ=14.02, 16.24 (d, $^3J_{C,P}$=8.1 Hz), 22.57, 25.67, 28.92, 29.14, 29.24, 29.41, 31.62, 36.70, 39.58,

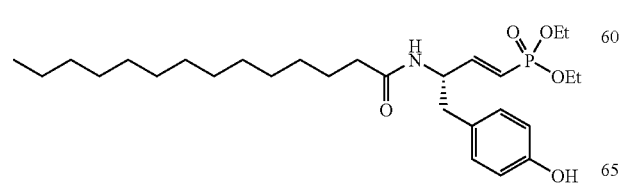

51.96 (d, $^3J_{C,P}$=22.2 Hz), 62.10 (q, $^2J_{C,P}$=11.0, 6.0 Hz), 115.59, 116.59 (d, $^1J_{C,P}$=189.4 Hz), 115.62, 126.70, 130.31, 152.15 (d, $^2J_{C,P}$=6.1 Hz), 156.08, 172.96.

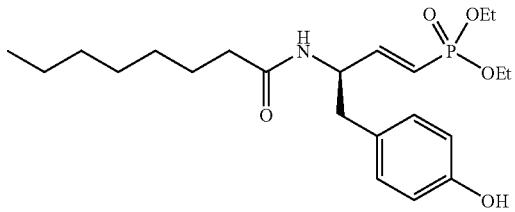

EXAMPLE 24

(3R)-[3-octanoylamino-4-(4-hydroxy-phenyl)-trans-but-1-enyl]-diethyl Phosphonate $^1$H NMR (300 MHz, CDCl$_3$) δ=0.85 (t, 3H, J=6.5), 1.12-1.34 (m, 14H), 1.48-1.63 (m, 2H), 2.14 (t, 2H, J=7.6), 2.71-2.88 (m, 2H), 3.89-4.06 (m, 4H), 4.81-4.97 (m, 1H), 5.64 (apparent t, 1H, J=18.7), 5.95 (d, 1H, J=8.5), 6.64-6.82 (m, 3H), 6.96 (d, 2H, J=8.4). $^{13}$C NMR (300 MHz, CDCl$_3$) δ=14.05, 16.20 (d, $^3J_{C,P}$=6.1 Hz), 22.59, 25.67, 28.90, 29.11, 29.22, 29.38, 31.78, 36.62, 39.50, 52.07 (d, $^3J_{C,P}$=22.2 Hz), 62.05 (t, $^2J_{C,P}$=7.1 Hz), 115.57, 116.49 (d, $^1J_{C,P}$=187.4 Hz), 126.65, 130.26, 152.17 (d, $^2J_{C,P}$=6.0 Hz), 156.14, 173.04.

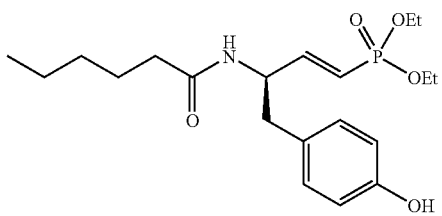

EXAMPLE 25

(3R)-[3-hexanoylamino-4-(4-hydroxy-phenyl)-trans-but-1-enyl]-diethyl Phosphonate $^1$H NMR (300 MHz, CDCl$_3$) δ=0.84 (t, 3H, J=6.9), 1.16-1.33 (m, 10H), 1.54 (p, 2H, J=8.3, 7.5), 2.14 (t, 2H, J=7.5), 2.73-2.82 (m, 2H), 3.87-4.05 (m, 4H), 4.80-4.95 (m, 1H), 5.64 (apparent t, 1H, J=18.5), 6.17 (d, 1H, J=8.5), 6.64-6.81 (m, 3H), 6.95 (d, 2H, J=8.4). $^{13}$C NMR (300 MHz, CDCl$_3$) δ=13.83, 16.18 (d, $^3J_{C,P}$=8.1 Hz), 22.27, 25.35, 31.27, 36.51, 39.47, 52.18 (d, $^3J_{C,P}$=22.2 Hz), 62.07 (t, $^2J_{C,P}$=7.1 Hz), 115.54, 116.44 (d, $^1J_{C,P}$=187.4 Hz), 126.73, 130.20, 152.20 (d, $^2J_{C,P}$=6.1 Hz), 156.14, 173.15.

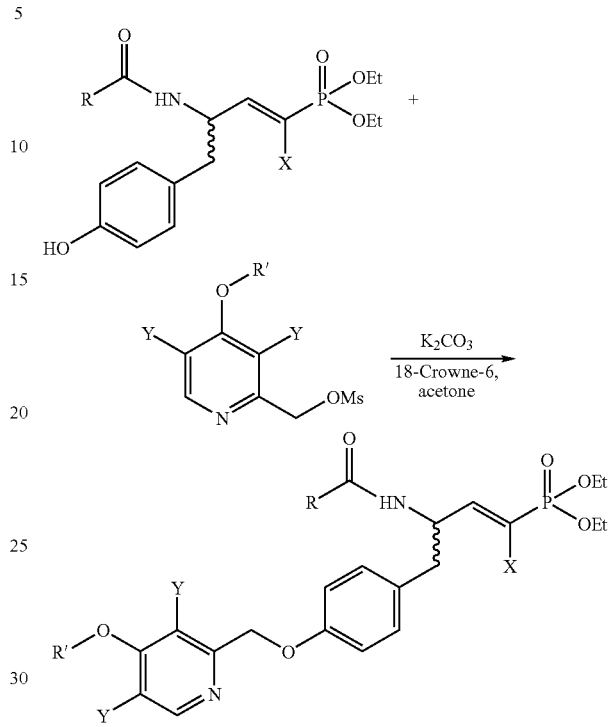

X = H, F, Cl

EXAMPLE 26

General Procedure for Ether Coupling, Synthesis of (3-acylamino-4-pyridin-2-ylmethoxy]-phenyl}-trans-but-1-enyl)-diethyl Phosphonates To the appropriate 3-acylamino-4-[4-hydroxy-phenyl]-3-acyl amine-trans-but-1-enyl}-diethyl phosphonate (1 mmol) and the substituted 2-methanesulfoxymethylpyridine (1.2 mmol) in acetone are added K$_2$CO$_3$ (10 mmol) and 18-crown-6 (0.1 mmol). The reaction mixture is refluxed for 16 hours until completion, as judged by TLC. Upon completion, the reaction is filtered, the solvent evaporated under reduced pressure, and subject to flash chromatography (1% MeOH in EtOAc to 10% MeOH in EtOAc) to afford the product as white crystals (85-98% yields).

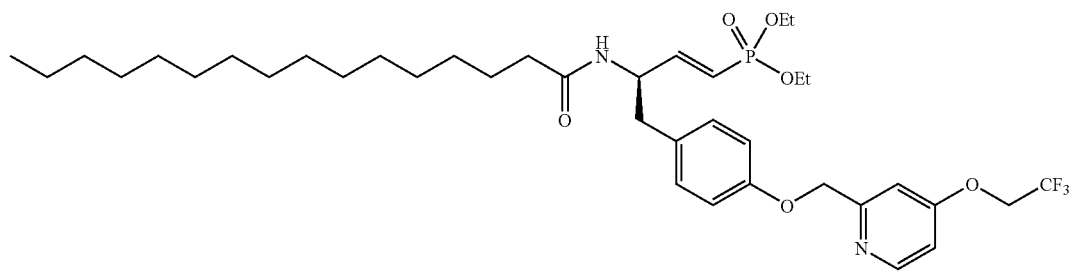

EXAMPLE 27

(3R)-(3-Hexadecanoylamino-4-{4-[4-(2,2,2-trifluoro-ethoxy)-pyridin-2-ylmethoxy]-phenyl}-trans-but-1-enyl)-diethyl Phosphonate $^1$H NMR (300 MHz, CDCl$_3$) δ=0.87 (t, 3H, J=6.5), 1.15-1.35 (m, 30H), 1.45-1.57 (m, 2H), 2.10 (t, 2H, J=7.4), 2.81 (apparent d, 2H, J=7.0), 3.87-4.02 (m, 4H), 4.39 (q, 2H, J=8.0), 4.80-4.92 (m, 1H), 5.09 (s, 2H), 5.63 (ddd, 1H, J=19.5, 17.1, 1.65), 6.03 (d, 1H, J=8.6), 6.67 (ddd, 1H, J=21.0, 18.0, 5.1), 6.75 (dd, 1H, J=5.8, 2.5), 6.86 (d, 2H, J=8.6), 7.03-7.10 (m, 3H), 8.42 (d, 1H, J=5.9). $^{13}$C NMR (300 MHz, CDCl$_3$) δ=13.94, 14.05, 16.17 (d, $^3J_{C,P}$=6.0 Hz), 20.86, 22.54, 25.59, 28.92, 29.24, 29.38, 29.51, 29.57, 31.78, 36.51, 39.39, 51.91 (d, $^3J_{C,P}$=22.2 Hz), 61.70 (d, $^2J_{C,P}$=5.0 Hz), 64.79 (q, $^2J_{C,F}$=36.26), 70.16, 107.21, 109.00, 114.74, 117.01 (d, $^1J_{C,P}$=185.3 Hz), 129.22, 130.31, 150.72, 151.45 (d, $^2J_{C,P}$=6.0 Hz), 157.05, 159.66, 160.04, 172.51. MS (ESI) m/z=727.5 ((M+H)$^+$, 100%).

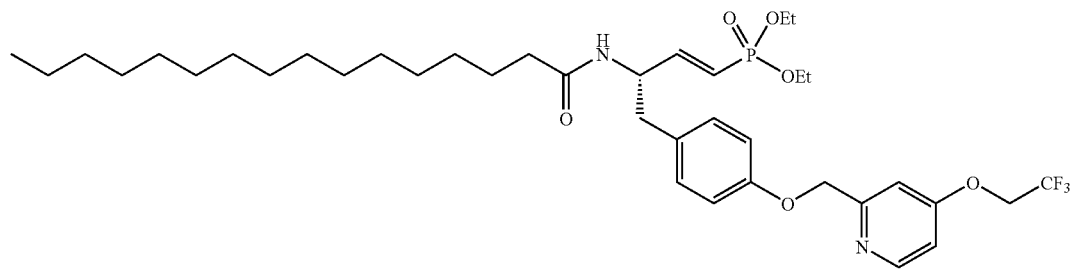

EXAMPLE 28

(3S)-(3-Hexadecanoylamino-4-{4-[4-(2,2,2-trifluoro-ethoxy)-pyridin-2-ylmethoxy]-phenyl}-trans-but-1-enyl)-diethyl Phosphonate This product has similar spectral properties as its enantiomer.

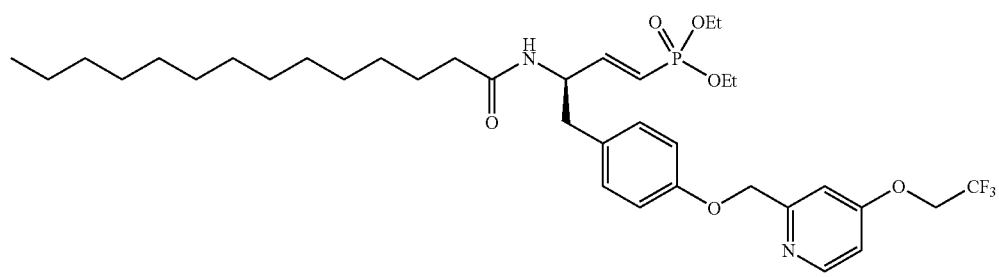

EXAMPLE 29

(3R)-(3-tetraadecanoylamino-4-{4-[4-(2,2,2-trifluoro-ethoxy)-pyridin-2-ylmethoxy]-phenyl}-trans-but-1-enyl)-diethyl Phosphonate $^1$H NMR (300 MHz, CDCl$_3$) δ=0.86 (t, 3H, J=6.7), 1.13-1.35 (m, 26H), 1.46-1.60 (m, 2H), 2.12 (t, 2H, J=7.4), 2.84 (d, 2H, J=7.0), 3.91-4.07 (m, 4H), 4.41 (q, 2H, J=7.9), 4.83-4.97 (m, 1H), 5.12 (s, 2H), 5.52 (d, 1H, J=8.4), 5.65 (ddd, 1H, J=18.0, 17.0, 1.8), 6.70 (ddd, 1H, J=21.1, 17.0, 5.1), 6.78 (dd, 1H, J=5.3, 2.4), 6.90 (d, 2H, J=8.8), 7.06-7.11 (m, 3H), 8.45 (d, 1H, J=5.7). $^{13}$C NMR (300 MHz, CDCl$_3$) δ=14.05, 16.35 (d, $^3J_{C,P}$=6.0 Hz), 22.62, 25.61, 29.16, 29.30, 29.43, 29.57, 31.84, 36.64, 39.42, 51.80 (d, $^3J_{C,P}$=22.2 Hz), 61.76 (d, $^2J_{C,P}$=6.0 Hz), 64.85 (q, $^2J_{C,F}$=36.3), 70.19, 107.23, 109.08, 114.82, 117.13 (d, $^1J_{C,P}$=187.3 Hz), 129.06, 130.28, 130.39, 150.80, 151.40 (d, $^2J_{C,P}$=6.0 Hz), 157.13, 159.69, 159.98, 164.10, 172.51. MS (ESI) m/z=699.4 ((M+H)$^+$, 100%).

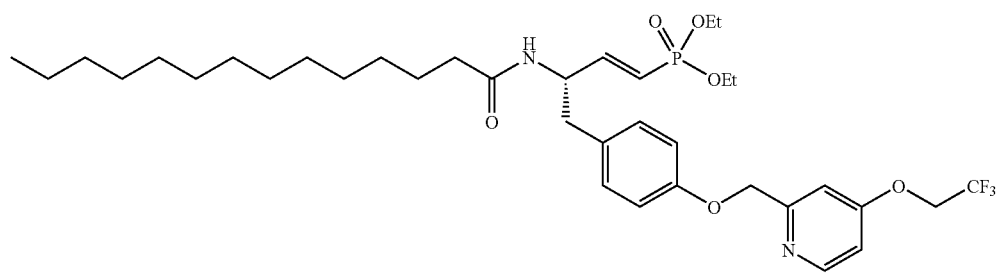

EXAMPLE 30

(3S)-(3-tetraadecanoylamino-4-{4-[4-(2,2,2-trifluoro-ethoxy)-pyridin-2-ylmethoxy]-phenyl}-trans-but-1-enyl)-diethyl Phosphonate This product has similar spectral properties as its enantiomer.

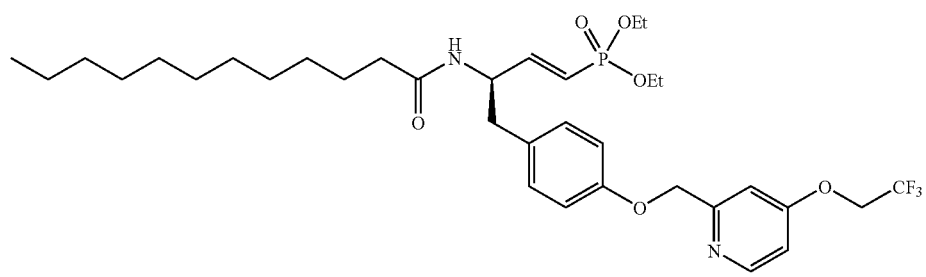

EXAMPLE 31

(3R)-(3-dodecanoylamino-4-{4-[4-(2,2,2-trifluoro-ethoxy)-pyridin-2-ylmethoxy]-phenyl}-trans-but-1-enyl)-diethyl Phosphonate $^1$H NMR (300 MHz, CDCl$_3$) δ=0.86 (t, 3H, J=6.2), 1.14-1.43 (m, 22H), 1.48-1.62 (m, 2H), 2.12 (t, 2H, J=7.4), 2.84 (d, 2H, J=6.8), 3.91-4.08 (m, 4H), 4.42 (q, 2H, J=7.9), 4.85-4.97 (m, 1H), 5.14 (s, 2H), 5.44 (d, 1H, J=8.4), 5.65 (ddd, 1H, J=18.1, 17.1, 1.7), 6.69 (ddd, 1H, J=20.6, 16.8, 4.8), 6.79 (dd, 1H, J=6.0, 2.6), 6.89 (d, 2H, J=8.8), 7.05-7.16 (m, 3H), 8.45 (d, 2H, J=5.7). $^{13}$C NMR (300 MHz, CDCl$_3$) δ=14.02, 16.25 (d, $^3J_{C,P}$=6.0 Hz), 22.59, 25.61, 29.16, 29.24, 29.30, 29.41, 29.57, 31.84, 36.64, 39.39, 51.80 (d, $^3J_{C,P}$=22.2 Hz), 61.76 (d, $^2J_{C,P}$=6.0 Hz), 64.85 (q, $^2J_{C,F}$=36.3), 70.14, 107.26, 109.10, 114.82, 117.11 (d, $^1J_{C,P}$=187.4 Hz), 129.06, 130.39, 130.84, 150.72, 151.40 (d, $^2J_{C,P}$=6.0 Hz), 157.10, 160.25, 166.45, 172.51.

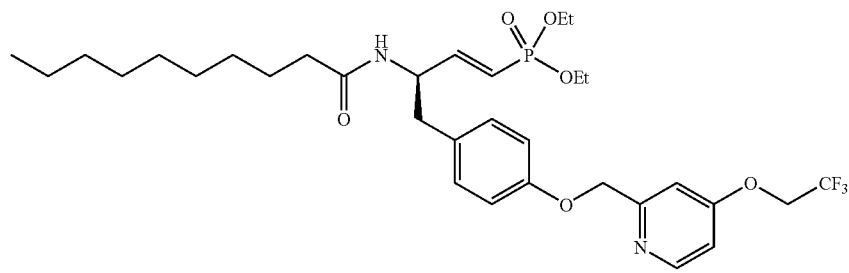

EXAMPLE 32

(3R)-(3-decanoylamino-4-{4-[4-(2,2,2-trifluoro-ethoxy)-pyridin-2-ylmethoxy]-phenyl}-trans-but-1-enyl)-diethyl Phosphonate $^1$H NMR (300 MHz, CDCl$_3$) δ=0.84 (t, 3H, J=6.2), 1.14-1.31 (m, 18H), 1.44-1.60 (m, 2H), 2.11 (t, 2H, J=7.6), 2.82 (d, 2H, J=6.4), 3.89-4.06 (m, 4H), 4.40 (q, 2H, J=7.9), 4.83-4.97 (m, 1H), 5.10 (s, 2H), 5.64 (apparent t, 1H, J=18.4), 5.83 (d, 1H, J=8.0), 6.59-6.81 (m, 2H), 6.88 (d, 2H, J=8.4), 7.04-7.12 (m, 3H), 8.44 (d, 1H, J=5.7). $^{13}$C NMR (300 MHz, CDCl$_3$) δ=13.97, 16.24 (d, $^3J_{C,P}$=8.0 Hz), 22.51, 25.61, 28.92, 29.08, 29.62, 31.57, 36.59, 39.39, 51.86 (d, $^3J_{C,P}$=22.2 Hz), 61.84 (d, $^2J_{C,P}$=6.0 Hz), 64.85 (q, $^2J_{C,F}$=36.3), 70.11, 107.26, 109.08, 114.79, 117.02 (d, $^1J_{C,P}$=187.4 Hz), 129.14, 130.39, 150.72, 151.48 (d, $^2J_{C,P}$=6.0 Hz), 157.07, 159.64, 164.12, 172.56.

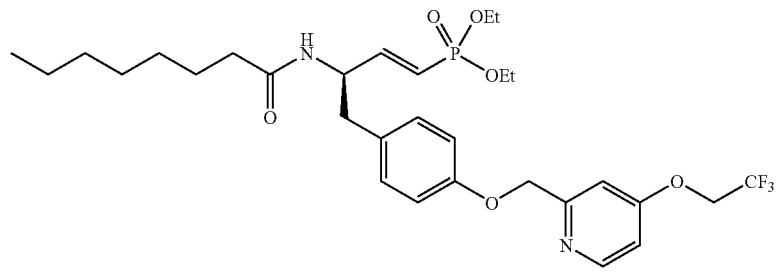

EXAMPLE 33

(3R)-(3-octanoylamino-4-{4-[4-(2,2,2-trifluoro-ethoxy)-pyridin-2-ylmethoxy]-phenyl}-trans-but-1-enyl)-diethyl Phosphonate $^1$H NMR (300 MHz, CDCl$_3$) δ=0.85 (t, 3H, J=6.6), 1.18-1.31 (m, 14H), 1.48-1.57 (m, 2H), 2.12 (t, 2H, J=7.5), 2.84 (d, 2H, J=6.8), 3.90-4.07 (m, 4H), 4.41 (q, 2H, J=7.9), 4.84-4.97 (m, 1H), 5.13 (s, 2H), 5.57-5.72 (m, 2H), 6.70 (ddd, 1H, J=21.4, 16.8, 4.8), 6.80 (dd, 1H, J=5.7, 2.6), 6.90 (d, 2H, J=8.6), 7.05-7.12 (m, 3H), 8.46 (d, 1H, J=5.7). $^{13}$C NMR (300 MHz, CDCl$_3$) δ=14.05, 16.28 (d, $^3J_{C,P}$=6.0 Hz), 22.62, 25.64, 29.24, 29.67, 31.81, 36.70, 39.42, 51.83 (d, $^3J_{C,P}$=22.2 Hz), 61.82 (t, $^2J_{C,P}$=6.0 Hz), 65.14 (q, $^2J_{C,F}$=36.3), 70.14, 107.31, 109.16, 114.87, 117.13 (d, $^1J_{C,P}$=187.4 Hz), 129.06, 129.62, 130.44, 150.74, 151.42 (d, $^2J_{C,P}$=6.0 Hz), 157.15, 159.66, 164.20, 172.54.

EXAMPLE 34

(3R)-(3-hexanoylamino-4-{4-[4-(2,2,2-trifluoro-ethoxy)-pyridin-2-ylmethoxy]-phenyl}-trans-but-1-enyl)-diethyl Phosphonate $^1$H NMR (300 MHz, CDCl$_3$) δ=0.86 (t, 3H, J=6.9), 1.16-1.35 (m, 10H), 1.54 (p, 2H, J=7.5), 2.13 (t, 2H, J=7.4), 2.84 (d, 2H, J=7.0), 3.92-4.08 (m, 4H), 4.42 (q, 2H, J=7.9), 4.84-4.97 (m, 1H), 5.13 (s, 2H), 5.58-5.78 (m, 2H), 6.71 (ddd, 1H, J=22.4, 16.9, 4.8), 6.80 (dd, 1H, J=5.9, 2.6), 6.90 (d, 2H, J=8.6), 7.09 (apparent d, 3H, J=8.6), 8.46 (d, 1H, J=5.7). $^{13}$C NMR (300 MHz, CDCl$_3$) δ=13.83, 16.21 (d, $^3J_{C,P}$=6.0 Hz), 22.30, 25.29, 29.65, 31.27, 36.59, 39.37, 51.83 (d, $^3J_{C,P}$=22.2 Hz), 61.87 (d, $^2J_{C,P}$=6.0 Hz), 64.87 (q, $^2J_{C,F}$=36.3), 70.11, 107.29, 109.16, 114.85, 117.07 (d, $^1J_{C,P}$=187.4 Hz), 129.08, 130.42, 150.69, 151.49 (d, $^2J_{C,P}$=6.0 Hz), 157.13, 159.64, 167.14, 172.56.

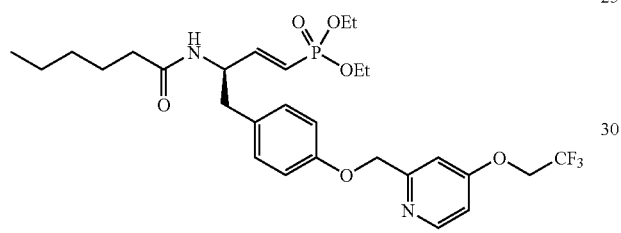

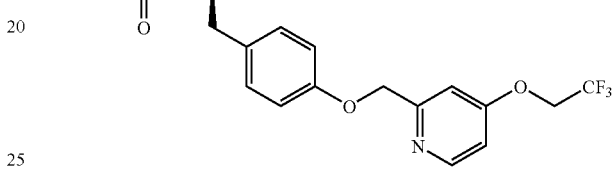

EXAMPLE 35

(3R)-(3-benzylamino-4-{4-[4-(2,2,2-trifluoro-ethoxy)-pyridin-2-ylmethoxy]-phenyl}-trans-but-1-enyl)-diethyl Phosphonate $^1$H NMR (300 MHz, CDCl$_3$) δ=1.19-1.32 (m, 6H), 2.98 (apparent d, 2H, J=6.9), 3.92-4.08 (m, 4H), 4.39 (q, 2H, J=7.9), 5.12 (s, 2H), 5.72 (ddd, 1H, J=21.4, 17.1, 1.2), 6.58 (d, 1H, J=8.4), 6.75-6.68 (m, 2H), 6.91 (d, 2H, J=8.6), 7.09 (d, 1H, J=2.4), 7.14 (d, 2H, J=8.4), 7.35-7.57 (m, 4H), 7.72 (d, 2H, J=7.0), 8.47 (d, 1H, J=5.7). $^{13}$C NMR (300 MHz, CDCl$_3$) δ=16.24 (d, $^3J_{C,P}$=8.1 Hz), 39.39, 52.58 (d, $^3J_{C,P}$=22.2 Hz), 61.91 (d, $^2J_{C,P}$=6.0 Hz), 64.85 (q, $^2J_{C,F}$=36.3), 70.03, 107.26, 109.21, 114.90, 117.32 (d, $^1J_{C,P}$=187.4 Hz), 126.92, 128.52, 129.06, 130.50, 131.65, 134.00, 150.64, 151.38 (d, $^2J_{C,P}$=4.0 Hz), 157.13, 159.61, 164.20, 172.51.

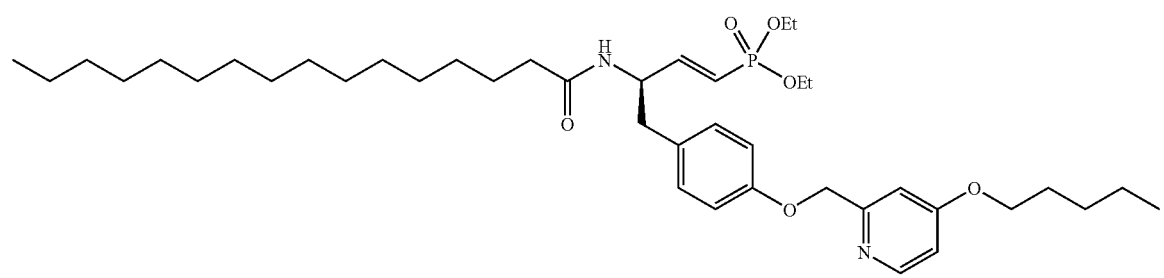

EXAMPLE 36

(3R)-(3-hexadecanoylamino-4-{4-[4-(pentoxy)-pyridin-2-ylmethoxy]-phenyl}-trans-but-1-enyl)-diethyl Phosphonate

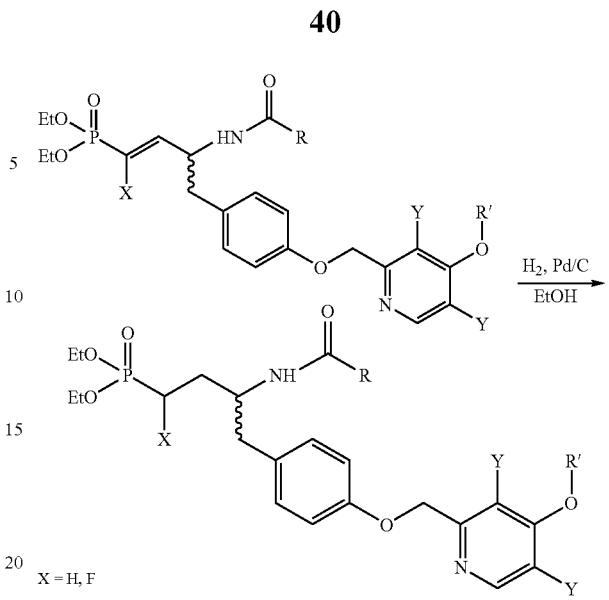

X = H, F $^1$H NMR (300 MHz, CDCl$_3$) δ=0.87 (t, 3H, J=6.6), 0.93 (t, 3H, J=6.8), 1.15-1.36 (m, 30H), 1.37-1.49 (m, 4H), 1.49-1.60 (m, 2H), 2.79 (p, 2H, J=6.9), 2.13 (t, 2H, J=7.5), 2.85 (dd, 2H, J=1.7, 6.6), 3.96-4.07 (m, 4H), 4.12 (q, 2H, J=7.3), 4.85-4.98 (m, 1H), 5.10 (s, 2H), 5.37 (d, 2H, J=8.6), 5.65 (ddd, 1H, J=19.3, 17.1, 1.6), 6.63-6.80 (m, 2H), 6.91 (d, 2H, J=8.6), 7.02 (d, 1H, J=2.4), 7.08 (d, 2H, J=8.6), 8.38 (d, 1H, J=5.7).
$^{13}$C NMR (300 MHz, CDCl$_3$) δ=13.91, 14.07, 16.39 (d, $^3J_{C,P}$=6.0 Hz), 22.35, 22.65, 25.64, 28.02, 28.55, 29.22, 29.32, 29.46, 29.62, 29.67, 31.89, 36.72, 39.39, 51.78 (d, $^3J_{C,P}$=22.2 Hz), 61.83 (t, $^2J_{C,P}$=6.0 Hz), 68.03 (q, $^2J_{C,F}$=36.3), 70.56, 107.63, 109.21, 114.95, 117.27 (d, $^1J_{C,P}$=187.4 Hz), 128.71, 130.36, 150.37, 151.40 (d, $^2J_{C,P}$=6.0 Hz), 166.07, 172.46

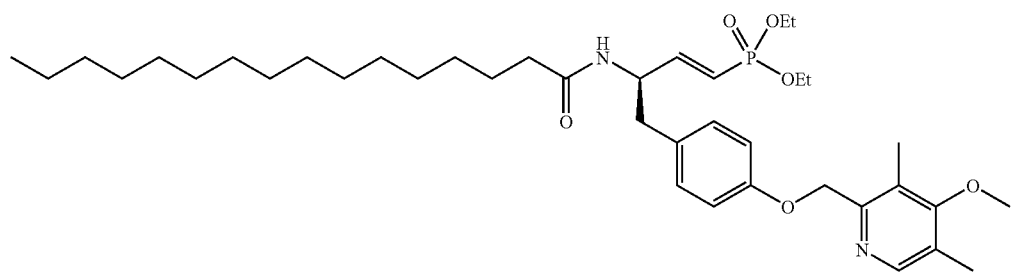

EXAMPLE 37

(3R)-{3-Hexadecanoylamino-4-[4-(4-methoxy-3,5-dimethyl-pyridin-2-ylmethoxy)-phenyl]-trans-but-1-enyl}-diethyl Phosphonate $^1$H NMR (300 MHz, CDCl$_3$) δ=0.86 (t, 3H, J=6.7), 1.15-1.36 (m, 26H), 1.47-1.62 (m, 2H), 2.13 (t, 2H, J=7.6), 2.25 (s, 3H). 2.31 (s, 3H), 2.83 (d, 2H, J=6.6), 3.77 (s, 3H), 3.90-4.09 (m, 4H), 4.84-4.97 (m, 1H), 5.10 (s, 2H), 5.56-5.71 (m, 2H), 6.70 (ddd, 1H, J=21.0, 17.0, 5.1), 6.93 (d, 2H, J=8.6), 7.05 (d, 2H, J=8.6), 8.22 (s, 1H). $^{13}$C NMR (300 MHz, CDCl$_3$) δ=10.90, 13.33, 14.07, 16.30 (d, $^3J_{C,P}$=6.0 Hz), 22.65, 25.64, 29.22, 29.30, 29.46, 29.65, 31.89, 36.70, 39.39, 51.78 (d, $^3J_{C,P}$=22.2 Hz), 59.85, 61.80 (d, $^2J_{C,P}$=6.0 Hz), 70.83, 114.95, 117.16 (d, $^1J_{C,P}$=187.4 Hz), 128.49, 130.26, 149.01, 151.49 (d, $^2J_{C,P}$=4.0 Hz), 154.11, 157.79, 172.48. MS (ESI) m/z=687.1 ((M+H)$^+$, 100%).

EXAMPLE 38

General Procedure for Reduction of Vinyl Phosphonate. Synthesis of {3-acylamino-[(4-pyridin-2-yl-methoxy)-phenyl]-butyl}-diethyl Phosphonates To (3-acylamino-4-pyridin-2-ylmethoxy]-phenyl}-trans-but-1-enyl)-diethyl phosphonate (0.1 mmol) dissolved in EtOH is added 10% Pd/C (0.01 mmol) and the solution allowed to stir at room temperature for 2 hours under a balloon of Hydrogen. Upon completion, the solution is filtered over celite and the volatiles are removed under reduced pressure. The residue is subject to flash chromatography (1-10% MeOH:EtOAc) to afford the product as colorless crystals (90-98% yield).

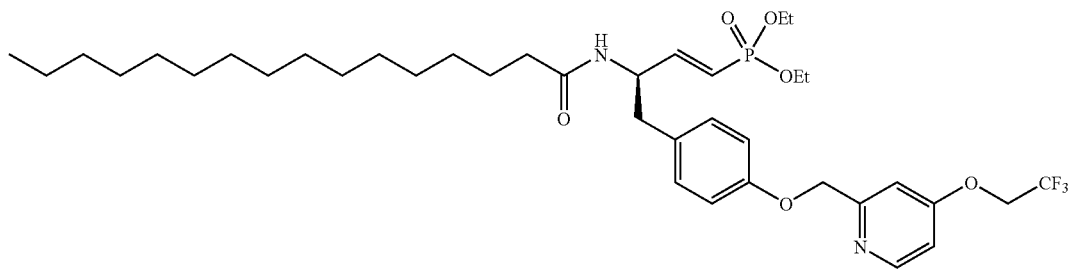

EXAMPLE 39

(1R)-(3-Hexadecanoylamino-4-{4-[4-(2,2,2-trifluoro-ethoxy)-pyridin-2-ylmethoxy]-phenyl}-butyl)-diethyl Phosphonate $^1$H NMR (300 MHz, CD$_3$OD) δ=0.79 (t, 3H, J=6.6), 1.04-1.20 (m, 30H), 1.38 (p, 2H, J=7.25), 1.60-1.75 (m, 2H), 2.00 (t, 2H, J=7.0), 2.50-2.71 (m, 2H), 3.88-4.03 (m, 7H), 4.61 (q, 2H, J=8.4), 5.00 (s, 2H), 6.84 (d, 2H, J=8.8), 6.92 (ddd, 1H, J=2.6, 5.9), 7.05 (d, 2H, J=8.8), 7.14 (d, 1H, J=2.6), 7.73 (d, 1H, J=9.0), 8.81 (d, 1H, J=5.7). $^{13}$C NMR (300 MHz, CD$_3$OD) δ=14.41, 16.72 (d, $^3J_{C,P}$=12.0 Hz), 21.97, 23.71. 23.87, 27.10, 28.30 (d, $^2J_{C,P}$=4.03 Hz), 30.17, 30.49, 30.62, 30.78, 33.05, 37.27, 40.88, 50.53 (d, $^3J_{C,P}$=16.1 Hz), 61.69 (d, $^2J_{C,P}$=10.1 Hz), 64.90 (d, $^2J_{C,F}$=36.3 Hz), 109.60, 110.56, 115.66, 115.74, 131.42, 132.52, 151.56, 158.35, 160.80, 161.42, 176.16. MS (ESI) m/z=729.4 ((M+H)$^+$, 100%).

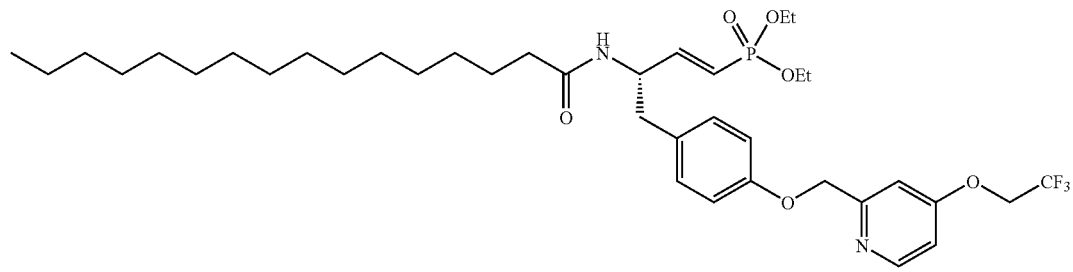

EXAMPLE 40

(1S)-(3-Hexadecanoylamino-4-{4-[4-(2,2,2-trifluoro-ethoxy)-pyridin-2-ylmethoxy]-phenyl}-butyl)-diethyl Phosphonate This product has similar spectral properties as its enantiomer.

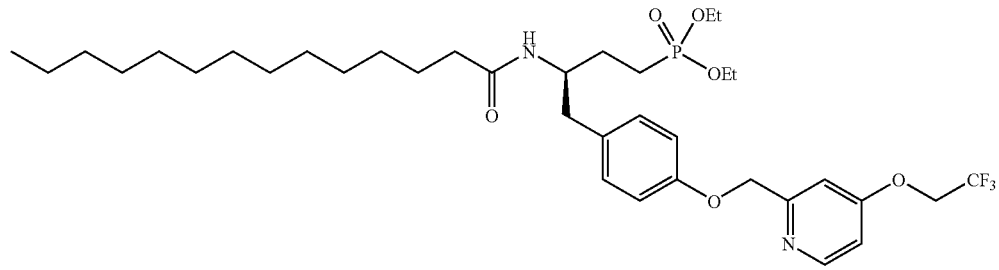

EXAMPLE 41

(1R)-(3-Tetradecanoylamino-4-{4-[4-(2,2,2-trifluoro-ethoxy)-pyridin-2-ylmethoxy]-phenyl}-butyl)-diethyl Phosphonate $^1$H NMR (300 MHz, CDCl$_3$) δ=0.86 (t, 3H, J=6.6), 1.15-1.34 (m, 28H), 1.46-1.64 (m, 2H), 1.66-1.89 (m, 2H), 2.10 (t, 2H, J=7.5), 2.62-2.83 (m, 2H), 3.94-4.20 (m, 7H), 4.41 (q, 2H, J=7.9), 5.13 (s, 2H), 5.74 (d, 1H, J=8.8), 6.78 (ddd, 1H, J=2.6, 5.7), 6.89 (d, 2H, J=8.1), 7.08 (apparent d, 3H, J=8.6), 8.46 (d, 1H, J=5.7). $^{13}$C NMR (300 MHz, CD$_3$OD) δ=14.05, 16.36 (d, $^3J_{C,P}$=6.0 Hz), 22.62, 23.13. 25.72, 26.44 (d, $^2J_{C,P}$=4.03 Hz), 29.22, 29.27, 29.32, 29.43, 29.59, 31.84, 36.86, 40.04, 50.65 (d, $^3J_{C,P}$=16.1 Hz), 61.63 (d, $^2J_{C,P}$=8.0 Hz), 64.85 (d, $^2J_{C,F}$=36.3 Hz), 107.18, 109.16, 114.71, 120.75, 120.96, 130.39, 150.69, 158.86, 159.82, 173.07.

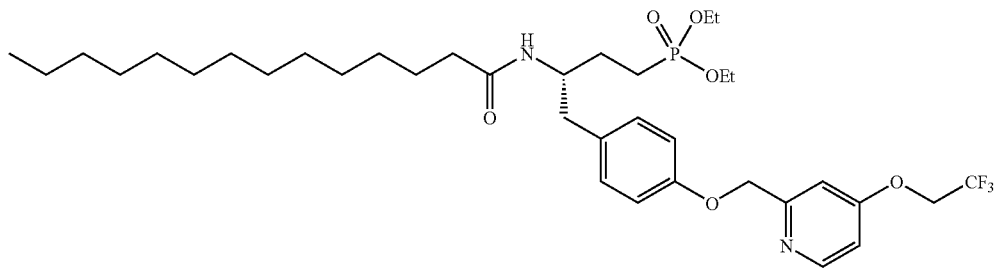

EXAMPLE 42

(1S)-(3-Tetradecanoyl-amino-4-{4-[4-(2,2,2-trifluoro-ethoxy)-pyridin-2-ylmethoxy]-phenyl}-butyl)-diethyl Phosphonate This product has similar spectral properties as its enantiomer.

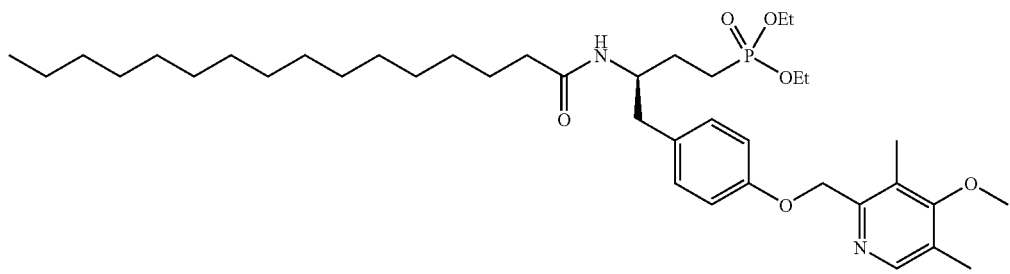

EXAMPLE 43

(1R)-{3-Hexadecanoylamino-4-[4-(4-methoxy-3,5-dimethyl-pyridin-2-ylmethoxy)-phenyl]-butyl}-diethyl Phosphonate $^1$H NMR (300 MHz, CDCl$_3$) δ=0.85 (t, 3H, J=6.6), 1.15-1.32 (m, 30H), 1.47-1.59 (m, 2H), 1.66-1.86 (m, 3H), 2.05-2.13 (m, 2H), 2.10 (t, 2H, J=7.5), 2.25 (s, 3H). 2.30 (s, 3H), 2.60-2.81 (m, 2H), 3.76 (s, 3H), 3.96-4.18 (m, 6H), 5.10 (s, 2H), 5.70 (d, 1H, J=8.6), 6.92 (d, 2H, J=8.6), 7.06 (d, 2H, J=8.6), 8.22 (s, 1H). $^{13}$C NMR (300 MHz, CD$_3$OD) δ=10.87, 13.30, 14.02, 16.36 (d, $^3J_{C,P}$=6.0 Hz), 22.59, 23.18, 25.69, 26.42 (d, $^2J_{C,P}$=4.0 Hz), 29.22, 29.30, 29.57, 29.62, 31.84, 36.83, 50.43 (d, $^3J_{C,P}$=16.1 Hz), 59.83, 61.59 (d, $^2J_{C,P}$=8.1 Hz), 70.72, 114.79, 129.83, 130.23, 148.85, 154.13, 157.47, 164.36, 172.99. MS (ESI) m/z=689.0 ((M+H)$^+$, 100%).

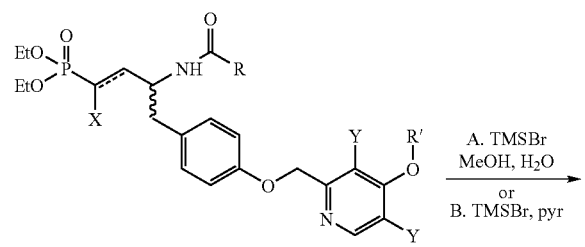

A. TMSBr MeOH, H$_2$O
or
B. TMSBr, pyr

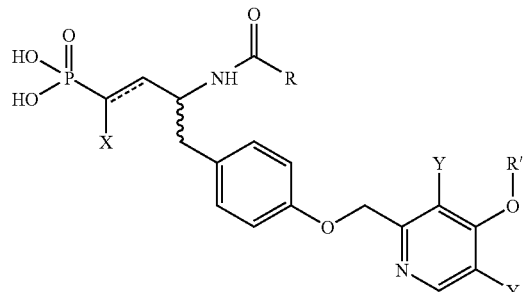

X = H, F, Cl

EXAMPLE 44

General Procedure for Ether Phosphonate Deprotection. Synthesis of {3-acylamino-[(4-pyridin-2-ylmethoxy)-phenyl-trans-but-1-enyl}-phosphonates Method A. To (3-acylamino-4-pyridin-2-ylmethoxy]-phenyl}-trans-but-1-enyl)-diethyl phosphonate (0.1 mmol) dissolved in CH$_2$Cl$_2$ is added TMSBr (1.0 mmol) and the solution allowed to stir at room temperature for 2 hours. The volatiles are removed under reduced pressure and water (2 mL) is added. The solution is stirred for 10 min, extracted with ether, and the aqueous layer is evaporated under reduced pressure. The residue is precipitated from either water or methanol and ether then filtered and washed with water and ether to provide the product as white crystals.

Method B. To (3-acylalkenylamino-4-pyridin-2-ylmethoxy]-phenyl}-trans-but-1-enyl)-diethyl phosphonate (0.1 mmol) dissolved in CH$_2$Cl$_2$ is added pyridine (1.0 mmol) then TMSBr (0.5 mmol) and the solution allowed to stir at room temperature for 6 hours. The volatiles are removed under reduced pressure and aqueous 1N NaOH (2 mL) is added. The solution is stirred for 20 min. then extracted with Et$_2$O to remove excess pyridine. The solution is made acidic (pH=1) with 1N HCl and the precipitate filtered and washed with water and ether to provide the product as white crystals.

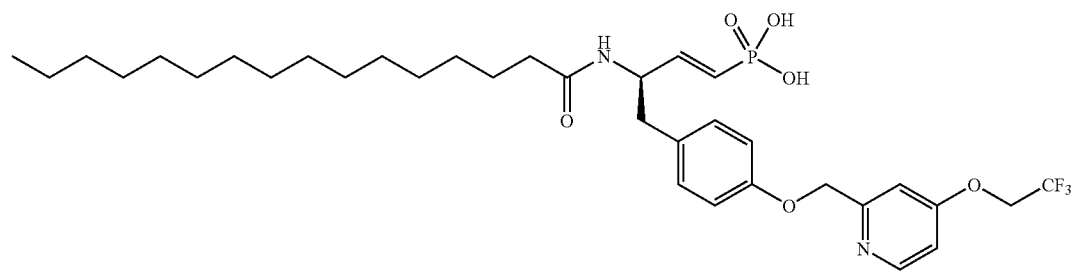

EXAMPLE 45

(3R)-(3-Hexadecanoylamino-4-{4-[4-(2,2,2-trifluoro-ethoxy)-pyridin-2-ylmethoxy]-phenyl}-trans-but-1-enyl)-phosphonic Acid (vpc51299)

$^1$H NMR (300 MHz, CD$_3$OD) δ=0.71 (t, 3H, J=6.7), 1.01-1.18 (m, 24H), 1.30-1.44 (m, 2H), 1.99 (t, 2H, J=7.6), 2.58-2.74 (m, 2H), 4.51-4.61 (m, 1H), 4.72 (q, 2H, J=7.8), 5.25 (s, 2H), 5.68 (apparent t, 1H, J=18.0), 6.37 (ddd, 1H, J=22.4, 17.1, 4.6), 6.83 (d, 2H, J=8.4), 7.02 (d, 2H, J=8.4), 7.37 (bs, 1H), 7.54 (bs, 1H), 8.64 (bs, 1H).

$^{13}$C NMR (300 MHz, CDCl$_3$) δ=14.44, 23.73, 27.05, 30.22, 30.46, 30.60, 30.78, 33.05, 37.06, 40.32, 54.15 (t, $^3J_{C,P}$=6.05 Hz), 67.35 (t, $^2J_{C,F}$=18.1 Hz), 112.22, 113.39, 115.96, 119.96 (d, $^1J_{C,P}$=167.2 Hz), 122.50, 131.72, 132.79, 145.79, 149.12 (d, $^2J_{C,P}$=6.0 Hz), 157.60, 170.79, 175.76. $^{31}$P NMR (121.5 MHz, CD$_3$OD:TFA) δ=16.53. $^{19}$F NMR (282 MHz, CD$_3$OD:TFA) δ=−75.71 (t, J=7.93 Hz, 3F). HRMS (ESI) m/z=671.3444 found (671.3437 calc). EA found: C, 54.51; H, 7.18; N, 3.70. (calc: C, 60.88; H, 7.51; N, 4.18.)

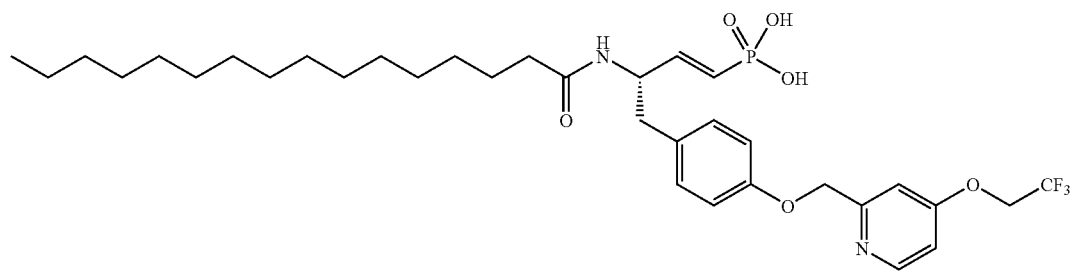

EXAMPLE 46

(3S)-(3-Hexadecanoylamino-4-{4-[4-(2,2,2-trifluoro-ethoxy)-pyridin-2-ylmethoxy]-phenyl}-trans-but-1-enyl)-phosphonic Acid (vpc52156)

This product has similar spectral properties as its enantiomer.

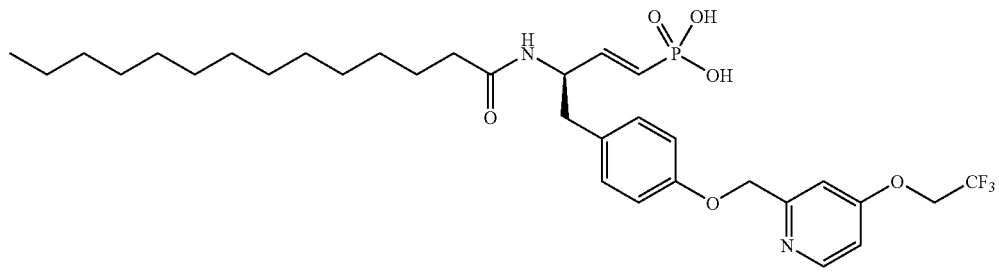

EXAMPLE 47

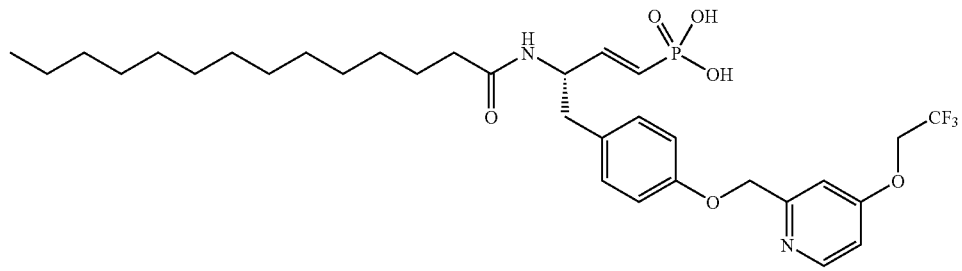

EXAMPLE 48

(3S)-(3-Tetradecanoylamino-4-{4-[4-(2,2,2-trifluoro-ethoxy)-pyridin-2-ylmethoxy]-phenyl}-trans-but-1-enyl)-phosphonic Acid (vpc52157)

This product has similar spectral properties as its enantiomer.

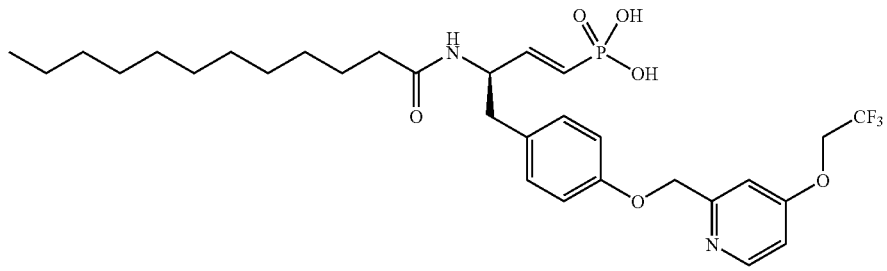

EXAMPLE 49

(3R)-(3-Dodecanoylamino-4-{4-[4-(2,2,2-trifluoro-ethoxy)-pyridin-2-ylmethoxy]-phenyl}-trans-but-1-enyl)-phosphonic Acid (vpc52172)

$^1$H NMR (300 MHz, DMSO) δ=0.83 (t, 3H, J=6.9), 1.07 (bs, 2H), 1.12-1.27 (m, 16H), 1.35 (p, 2H, J=7.3), 1.93-2.04 (m, 2H), 2.55-2.84 (m, 2H), 4.56 (bs, 1H), 4.94 (q, 2H, J=8.7), 5.10 (s, 2H), 5.71 (apparent t, 1H, J=18.4), 6.41 (ddd, 1H, J=22.4, 17.3, 4.5), 6.93 (d, 2H, J=6.9), 7.07-7.17 (m, 3H), 7.24 (s, 1H), 7.90 (d, 1H, J=8.65), 8.50 (d, 2H, J=5.1).

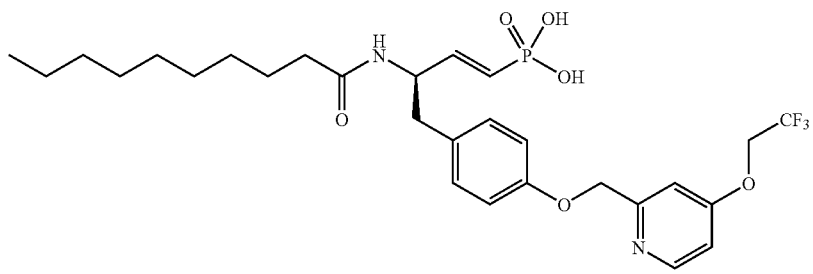

EXAMPLE 50

(3R)-(3-Decanoylamino-4-{4-[4-(2,2,2-trifluoro-ethoxy)-pyridin-2-ylmethoxy]-phenyl}-trans-but-1-enyl)-phosphonic Acid (vpc52173)

$^1$H NMR (300 MHz, DMSO) δ=0.82 (t, 3H, J=6.4), 1.08 (bs, 2H), 1.12-1.28 (m, 12H), 1.30-1.40 (m, 2H), 1.94-2.06 (m, 2H), 2.53-2.85 (m, 2H), 4.56 (bs, 1H), 4.95 (q, 2H, J=8.3), 5.11 (s, 2H), 5.71 (apparent t, 1H, J=18.0), 6.41 (ddd, 1H, J=22.3, 17.3, 3.6), 6.93 (d, 2H, J=7.4), 7.14 (d, 2H, J=7.0), 7.25 (s, 1H), 7.92 (d, 1H, J=8.7), 8.51 (s, 1H). $^{13}$C NMR (300 MHz, DMSO) δ=13.90, 22.07, 25.28, 28.45, 31.12, 35.35, 64.19 (q, $^2J_{C,F}$=34.6), 69.30, 108.75, 109.64, 114.36, 121.04 (d, $^1J_{C,P}$=181.0 Hz), 124.75, 131.19, 130.88, 146.92 (d, $^2J_{C,P}$=6.3 Hz), 156.38, 156.97, 164.32, 171.53. HRMS (ESI) m/z=587.2483 (M$^+$, C$_{28}$H$_{39}$F$_3$N$_2$O$_6$P requires 587.2498).

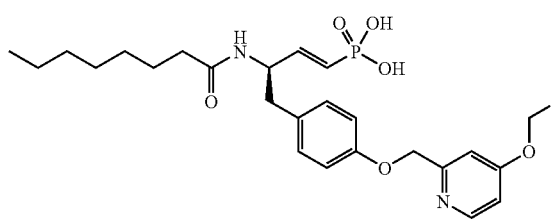

EXAMPLE 51

(1R)-(3-octanoylamino-4-{4-[4-(2,2,2-trifluoro-ethoxy)-pyridin-2-ylmethoxy]-phenyl}-trans-but-1-enyl)-phosphonic Acid (vpc52178)

$^1$H NMR (300 MHz, DMSO) δ=0.82 (t, 3H, J=6.4), 1.08-1.29 (m, 8H), 1.29-1.44 (m, 2H), 2.00 (t, 2H, J=6.3), 2.55-2.85 (m, 2H), 4.44-4.68 (m, 2H), 4.94 (q, 2H, J=8.8), 5.10 (s, 2H), 5.71 (apparent t, 1H, J=17.6), 6.41 (apparent t, 1H, J=19.4), 6.93 (d, 2H, J=7.7), 7.14 (d, 2H, J=7.7), 7.24 (s, 1H), 7.93 (d, 1H, J=7.5), 8.51 (bs, 1H). $^{13}$C NMR (300 MHz, DMSO) δ=13.89, 22.06, 24.54, 25.26, 28.47, 28.71, 28.84, 35.33, 51.68 (d, $^3J_{C,P}$=20.2 Hz), 64.50 (t, $^2J_{C,F}$=6.1 Hz), 69.47, 112.52, 113.27, 114.34, 118.45 (d, $^1J_{C,P}$=172.4 Hz), 124.35, 130.18, 130.84, 135.54, 146.99 (d, $^2J_{C,P}$=6.0 Hz), 156.46, 171.01, 171.65.

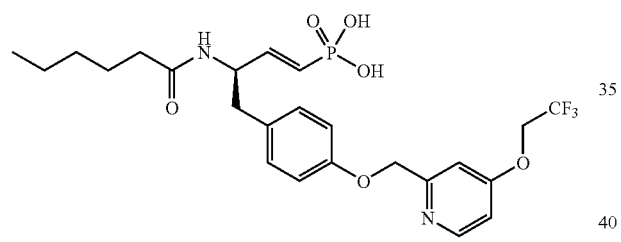

EXAMPLE 52

(3R)-(3-hexanoylamino-4-{4-[4-(2,2,2-trifluoro-ethoxy)-pyridin-2-ylmethoxy]-phenyl}-trans-but-1-enyl)-phosphonic Acid (vpc52183)

$^1$H NMR (300 MHz, DMSO) δ=0.80 (t, 3H, J=6.9), 0.99-1.14 (m, 2H), 1.14-1.29 (m, 2H), 1.30-1.46 (m, 2H), 1.92-.10 (m, 2H). 2.55-2.88 (m, 2H), 4.50-4.62 (m, 1H), 5.02-5.19 (m, 2H), 5.26 (s, 2H), 5.71 (apparent t, 1H, J=17.5), 6.41 (apparent t, 1H, J=19.2), 6.96 (d, 2H, J=7.1), 7.18 (d, 2H, J=6.5), 7.43-7.52 (m, 1H), 7.58 (d, 1H, J=5.8), 7.95 (d, 1H, J=8.1), 8.72 (s, 1H). $^{13}$C NMR (300 MHz, DMSO) δ=13.83, 21.81, 24.94, 30.68, 32.54, 35.30, 51.72 (d, $^3J_{C,P}$=22.2 Hz), 65.32 (t, $^2J_{C,F}$=34.2), 67.08, 110.65, 111.15, 114.45, 121.50 (d, $^1J_{C,P}$=178.7 Hz), 130.28, 131.45, 146.67, 146.96 (d, $^2J_{C,P}$=5.8 Hz), 155.95, 166.95, 17.52.

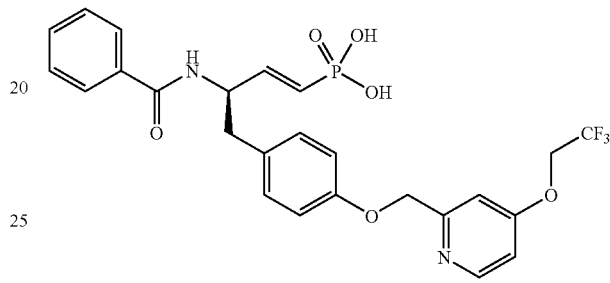

EXAMPLE 53

(3R)-(3-benzylamino-4-{4-[4-(2,2,2-trifluoro-ethoxy)-pyridin-2-ylmethoxy]-phenyl}-trans-but-1-enyl)-phosphonic Acid (vpc52206)

$^1$H NMR (300 MHz, CDCl$_3$) δ=2.84-3.10 (m, 2H), 4.93 (q, 2H, J=7.8), 5.31 (s, 2H), 5.74-6.00 (m, 1H), 6.70 (apparent t, 1H, J=17.6), 7.01 (d, 2H, J=7.5), 7.27 (d, 2H, J=7.7), 7.36-7.55 (m, 4H), 7.62 (apparent s, 1H), 7.72 (d, 2H, J=7.5), 8.60 (d, 1H, J=6.0). $^{13}$C NMR (300 MHz, CDCl$_3$) δ=40.31, 55.07 (d, $^3J_{C,P}$=22.2 Hz), 62.56, 67.26 (d, $^2J_{C,F}$=36.3), 106.66, 110.02, 116.16, 118.34 (d, $^1J_{C,P}$=187.4 Hz), 128.48, 129.71, 131.87, 132.91, 133.10, 135.72, 151.87 (d, $^2J_{C,P}$=4.0 Hz), 157.91, 159.61, 169.96, 170.28. HRMS (ESI) m/z=537.1397 (M$^+$, C$_{25}$H$_{25}$F$_3$N$_2$O$_6$P requires 537.1402).

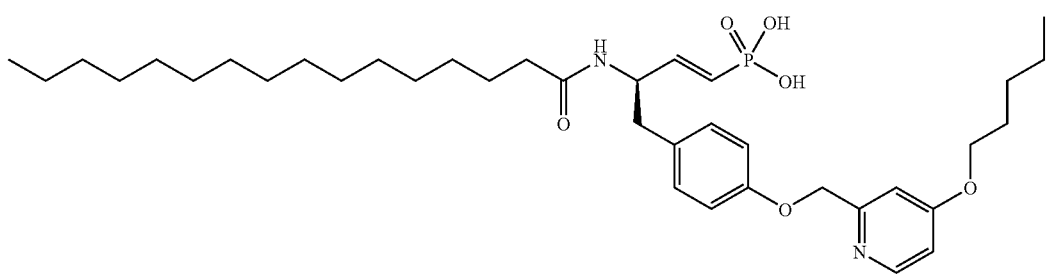

EXAMPLE 54

(1R)(3-Hexadecanoylamino-4-{4-[4-(Pentoxy)-pyridin-2-ylmethoxy]-phenyl}-trans-but-1-enyl)-phosphonic Acid (vpc52071)

$^1$H NMR (300 MHz, CD$_3$OD) δ=0.89 (t, 3H, J=6.7), 0.96 (t, 3H, J=7.1), 1.15-1.35 (m, 26H), 1.35-1.56 (m, 6H), 1.88 (p, 2H, J=6.7), 2.12 (t, 2H, J=7.5), 2.70-2.96 (m, 2H), 4.33 (t, 2H, J=6.4), 4.68-4.77 (m, 1H), 5.33 (s, 2H), 5.76 (apparent t, 1H, J=17.8), 6.61 (ddd, 1H, J=21.1, 16.7, 4.9), 7.00 (d, 2H, J=8.2), 7.22 (d, 2H, J=8.6), 7.89 (d, 1H, J=4.8), 7.53 (s, 1H), 8.54 (d, 1H, J=6.4).

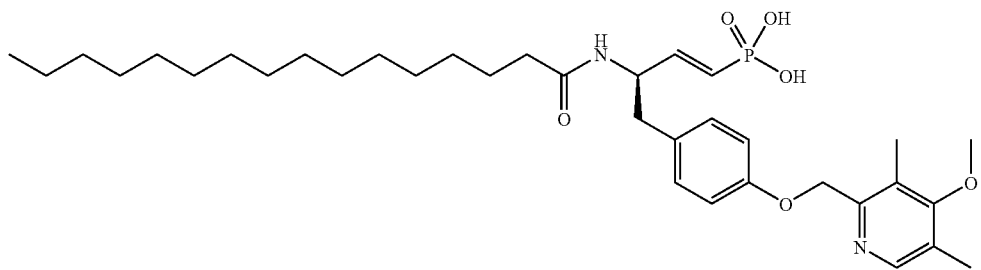

EXAMPLE 55

(3R)-{3-Hexadecanoylamino-4-[4-(4-methoxy-3,5-dimethyl-pyridin-2-ylmethoxy)-phenyl]-trans-but-1-enyl}-phosphonic Acid (vpc51304)

$^1$H NMR (300 MHz, CDCl$_3$/CD$_3$OD) δ=0.82 (t, 3H, J=6.6), 1.15-1.33 (m, 24H), 1.42-1.55 (m, 2H), 2.05-2.17 (m, 2H), 2.35 (s, 3H). 2.44 (s, 3H), 2.78 (d, 2H, J=6.0), 3.84-3.98 (m, 2H), 4.07 (s, 3H), 4.66-4.77 (m, 1H), 5.30 (s, 2H), 5.62 (apparent t, 1H, J=18.2), 6.54 (apparent t, 1H, J=18.6), 7.07 (d, 2H, J=8.6), 7.10 (d, 2H, J=7.5), 8.58 (s, 1H). $^{13}$C NMR (300 MHz, DMSO) δ=10.60, 13.69, 13.94, 22.06, 25.26, 28.50, 28.68, 28.79, 29.03, 31.27, 35.31, 50.71 (d, $^3J_{C,P}$=12.0 Hz), 58.41, 60.12, 70.54, 114.60, 118.13 (d, $^1J_{C,P}$=181.3 Hz), 124.35, 130.23, 149.58 (d, $^2J_{C,P}$=6.0 Hz), 155.95, 159.13, 171.75. HRMS (ESI) m/z=631.3870 (M$^+$, C$_{35}$H$_{56}$N$_2$O$_6$P requires 631.3876).

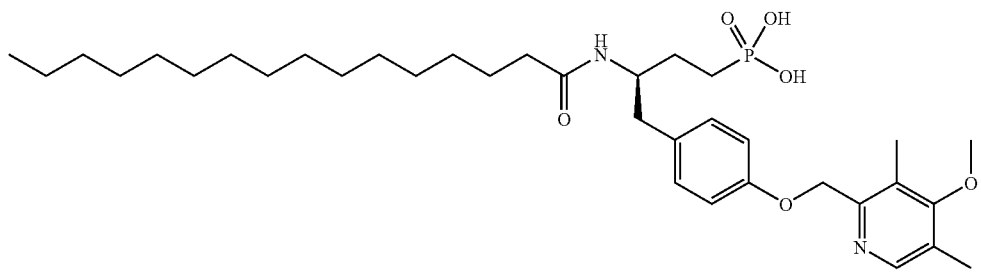

EXAMPLE 56

(1R)-{3-Hexadecanoylamino-4-[4-(4-methoxy-3,5-dimethyl-pyridin-2-ylmethoxy)-phenyl]-butyl}-phosphonic Acid (vpc52007)

$^1$H NMR (300 MHz, CDCl$_3$/CD$_3$OD) δ=0.80 (t, 3H, J=6.6), 1.05-1.28 (m, 24H), 1.37-1.57 (m, 2H), 1.69-1.81 (m, 3H), 2.05 (t, 2H, J=7.5), 2.31 (s, 3H). 2.35 (s, 3H). 2.48-2.75 (m, 2H), 3.84-4.05 (m, 5H), 5.18 (s, 2H), 6.90 (d, 2H, J=8.6), 7.05 (d, 2H, J=8.6), 8.39 (s, 1H). $^{13}$C NMR (300 MHz, CD$_3$OD) δ=10.19, 11.02, 13.96, 14.23, 14.41, 23.71, 27.13, 30.25, 30.46, 30.62, 30.78, 33.05, 37.40, 41.15, 52.85, 61.81, 65.77, 67.48, 116.07, 131.61, 131.66, 133.75, 133.85, 157.70, 176.03. HRMS (ESI) m/z=633.4033 (M$^+$, C$_{35}$H$_{58}$N$_2$O$_6$P requires 633.4033).

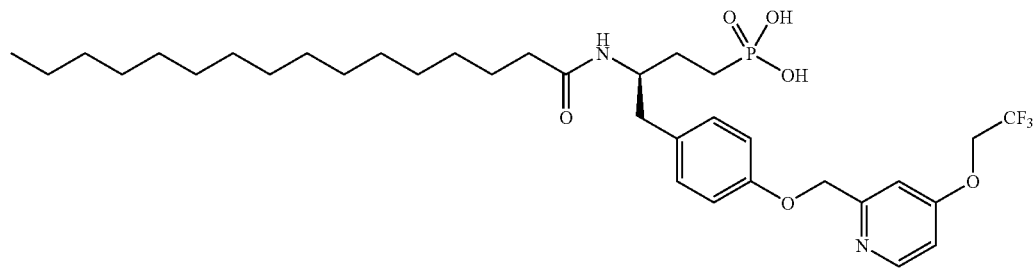

EXAMPLE 57

(1R)-(3-Hexadecanoylamino-4-{4-[4-(2,2,2-trifluoro-ethoxy)-pyridin-2-ylmethoxy]-phenyl}-butyl)-phosphonic Acid (vpc51303)

$^1$H NMR (300 MHz, CD$_3$OD) δ=0.89 (t, 3H, J=6.7), 1.12-1.39 (m, 22H), 1.40-1.55 (m, 2H), 1.56-1.72 (m, 2H), 1.72-1.91 (m, 2H), 2.09 (t, 2H, J=7.3), 2.58-2.83 (m, 2H), 3.93-4.12 (m, 3H), 4.90 (q, 2H, J=8.1), 5.28 (s, 2H), 6.98 (d, 2H, J=8.1), 7.18 (d, 2H, J=8.2), 7.42 (bs, 1H), 7.59 (bs, 1H), 8.61 (bs, 1H). $^{13}$C NMR (300 MHz, CD$_3$OD) δ=14.39, 23.71, 27.10, 28.89 (d, $^1$J$_{C,P}$=28.21 Hz), 30.22, 30.44, 30.60, 30.76, 33.03, 37.25, 41.01, 62.19, 66.63 (t, $^2$J$_{C,F}$=36.3 Hz), 115.88, 122.66, 126.32, 131.56, 133.48, 146.01, 157.76, 158.10, 169.14, 170.74, 176.11. HRMS (ESI)m/z=673.3597 (M$^+$, C$_{34}$H$_{53}$F$_3$N$_2$O$_6$P requires 673.3593).

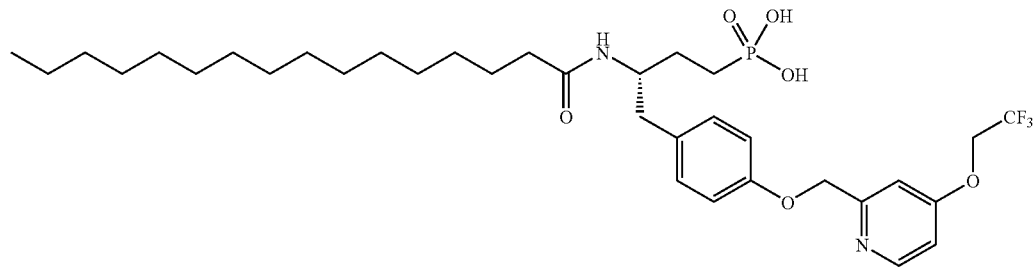

EXAMPLE 58

(1S)-(3-Hexadecanoylamino-4-{4-[4-(2,2,2-trifluoro-ethoxy)-pyridin-2-ylmethoxy]-phenyl}-butyl)-phosphonic Acid (vpc52162)

This product has similar spectral properties as its enantiomer.

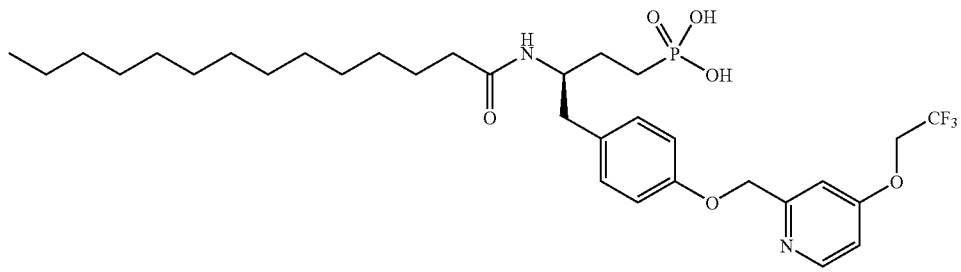

EXAMPLE 59

(1R)-(3-Tetradecanoylamino-4-{4-[4-(2,2,2-trifluoro-ethoxy)-pyridin-2-ylmethoxy]-phenyl}-butyl)-phosphonic Acid (vpc52079)

$^1$H NMR (300 MHz, CD$_3$OD) δ=0.88 (t, 3H, J=6.5), 1.09-1.35 (m, 20H), 1.44-1.57 (m, 2H), 1.60-1.90 (m, 2H), 2.00-2.18 (m, 2H), 2.62-2.82 (m, 2H), 3.95-4.12 (m, 3H), 4.99 (q, 2H, J=8.0), 5.37 (s, 2H), 6.70 (d, 1H, J=8.8), 7.01 (d, 2H, J=8.6), 7.20 (d, 1H, J=8.7), 7.57 (bs, 1H), 7.72 (bs, 1H), 8.70 (bs, 1H). HRMS (ESI) m/z=645.3273 (M$^+$, C$_{32}$H$_{49}$F$_3$N$_2$O$_6$P requires 645.3280).

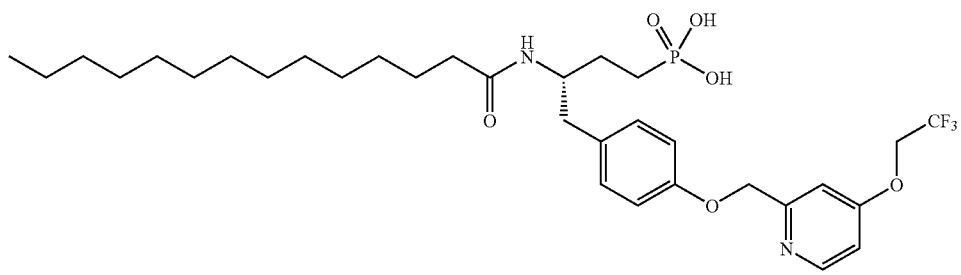

EXAMPLE 60

(1S)-(3-Tetradecanoylamino-4-{4-[4-(2,2,2-trifluoro-ethoxy)-pyridin-2-ylmethoxy]-phenyl}-butyl)-phosphonic Acid (vpc52163)

This product has similar spectral properties as its enantiomer.

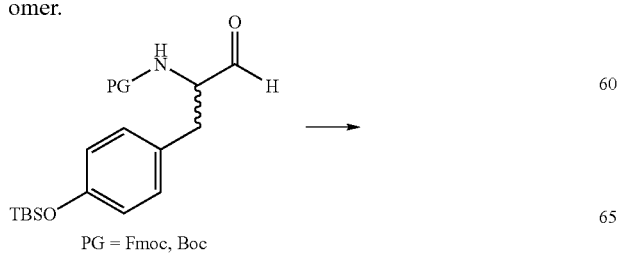

PG = Fmoc, Boc

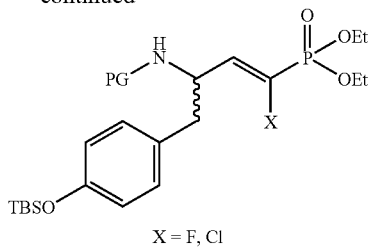

X = F, Cl

EXAMPLE 61

[4-[4-(tert-Butyl-dimethyl-silanyloxy)-phenyl]-3-(9H-fluoren-9-ylmethoxycarbonylamino)-trans-but-1-enyl]-phosphonic Acid Diethyl Ester or [4-[4-(tert-Butyl-dimethyl-silanyloxy)-phenyl]-3-(tert-butoxycarbonylamino)-trans-but-1-enyl]-phosphonic Acid Diethyl Ester To a solution of NaH (60% in mineral oil, 375 mg, 9.4 mmol) in THF (15 ml) at 0° C. is added the appropriate tetra-ethyl diphosphonate (9.4 mmol) in THF (15 ml) via cannulation. The mixture is stirred at 0° C. for 30 min and the aldehyde, dissolved in THF (25 ml), is added via cannulation. The mixture is allowed to stir an additional 30 minutes at 0° C. Excess NaH is consumed with saturated aqueous ammonium chloride, and the aqueous layer is extracted with Ethyl Acetate. The organic layer is washed with brine, dried (MgSO$_4$), evaporated to dryness, and subject to flash chromatography (1:1 Hexane:EtOAc to 100% EtOAc) to afford the product as a pale yellow oil (43% yield).

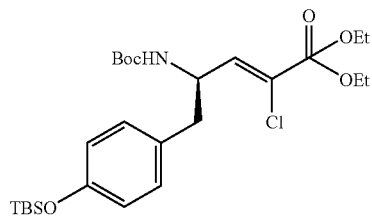

EXAMPLE 62

(3R)-[4-[4-(tert-Butyl-dimethyl-silanyloxy)-phenyl]-3-(tert-butoxycarbonylamino)-trans-1-chloro-but-1-enyl]-phosphonic Acid Diethyl Ester $^1$H NMR (300 MHz, CDCl$_3$) δ=0.07 (s, 6H), 0.87 (s, 9H), 1.21 (q, 6H, J=8.0, 7.5), 1.30 (s, 9H), 2.68-2.94 (m, 2H), 3.73-4.08 (m, 4H), 4.76 (bs, 1H), 4.76 (bs, 1H), 6.64 (d, 2H, J=8.4), 6.74 (dd, 1H, J=13.3, 9.9), 6.97 (d, 2H, J=8.4). $^{13}$C NMR (300 MHz, CDCl$_3$) δ=−5.02, 15.63 (d, $^3J_{C,P}$=8.0 Hz), 17.57, 25.10, 27.80, 38.67, 50.42 (d, $^3J_{C,P}$=16.1 Hz), 62.53 (dd, $^2J_{C,P}$=13.0, 5.0 Hz), 76.36, 119.39, 121.94 (d, $^1J_{C,P}$=207.51), 128.73, 129.91, 164.10 (d, $^2J_{C,P}$=16.1 Hz), 153.89, 154.54, 155.39, 169.49. $^{31}$P NMR (121.5 MHz, CDCl$_3$) δ=10.20. HRMS (ESI), M$^+$, Found: 548.2365. Calc for C$_{25}$H$_{44}$NO$_6$PSiCl, 548.2364.

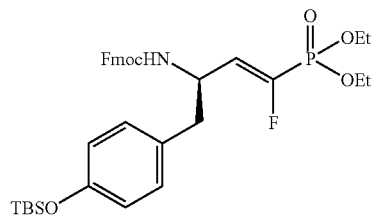

EXAMPLE 63

(3R)-[4-[4-(tert-Butyl-dimethyl-silanyloxy)-phenyl]-3-(9H-fluoren-9-ylmethoxycarbonylamino)-trans-1-fluoro-but-1-enyl]-phosphonic Acid Diethyl Ester $^1$H NMR (300 MHz, CDCl$_3$) δ=0.19 (s, 6H), 1.00 (s, 9H), 1.32 (t, 6H, J=7.0), 2.70-3.03 (m, 2H), 3.89-4.22 (m, 4H), 4.29-4.45 (m, 2H), 4.83-5.00 (m, 1H), 5.51 (d, 1H, J=6.8), 5.98 (dt, 1H, J=38.5, 8.1), 6.78 (d, 2H, J=8.4), 7.07 (d, 2H, J=7.0), 7.28-7.43 (m, 4H), 7.59 (d, 2H, J=7.5), 7.77 (d, 2H, J=7.3). $^{13}$C NMR (300 MHz, CDCl$_3$) δ=−4.60, 16.04 (d, $^3J_{C,P}$=6.0 Hz), 18.00, 25.51, 39.93, 47.06, 63.16 (dd, $^2J_{C,P}$=14.1, 6.0 Hz), 66.64, 119.84, 124.92, 125.50 (dd, $^1J_{C,P}$=27.2, 5.1), 126.95, 127.56, 128.90, 130.23, 141.15, 143.77, 154.46, 155.34. $^{31}$P NMR (121.5 MHz, CDCl$_3$) δ=5.21 (d, J=99.6 Hz).

$^{19}$F NMR (282 MHz, CDCl$_3$) δ=−126.77 (dd, J=101.1, 39.6 Hz). HRMS (ESI), M$^+$, Found: 654.2089. Calc for C$_{35}$H$_{46}$FNO$_6$PSi, 654.2816.

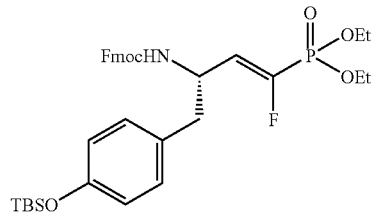

EXAMPLE 64

(3S)-[4-[4-(tert-Butyl-dimethyl-silanyloxy)-phenyl]-3-(9H-fluoren-9-ylmethoxycarbonylamino)-trans-1-fluoro-but-1-enyl]-phosphonic Acid Diethyl Ester This product has similar spectral properties as its enantiomer.

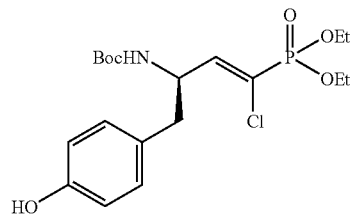

EXAMPLE 65

(3R)-[4-(4-hydroxy)-phenyl]-3-(tert-butoxycarbonylamino)-trans-1-chloro-but-1-enyl]-phosphonic Acid Diethyl Ester $^1$H NMR (300 MHz, CDCl$_3$) δ=1.15-1.34 (m, 6H), 1.38 (s, 9H), 2.65-2.96 (m, 2H), 3.81-4.18 (m, 4H), 4.83 (bs, 1H), 5.05 (bs, 1H), 6.68-6.79 (m, 3H), 6.98 (d, 2H, J=8.4). $^{13}$C NMR (75.5 MHz, CDCl$_3$) δ=15.80 (d, $^3J_{C,P}$=6.1 Hz), 27.99, 38.51, 50.45 (d, $^3J_{C,P}$=12.1 Hz), 63.25 (dd, $^2J_{C,P}$=10.1, 5.0 Hz), 76.36, 115.25, 122.02 (d, $^1J_{C,P}$=195.42), 126.52, 130.15, 146.51 (d, $^2J_{C,P}$=18.1 Hz), 155.66, 172.16. $^{31}$P NMR (121.5 MHz, CDCl$_3$) δ=10.16. δ=HRMS (ESI), M$^+$, Found: 456.1313. Calc for C$_{19}$H$_{29}$NO$_6$PClNa, 456.1319.

EXAMPLE 66

(3R)-[4-(4-hydroxy)-phenyl]-3-(tert-butoxycarbonylamino)-trans-1-fluoro-but-1-enyl]-phosphonic Acid Diethyl Ester $^1$H NMR (300 MHz, CDCl$_3$) δ=1.21-1.35 (m, 6H), 1.41 (s, 9H), 2.63-2.90 (m, 2H), 3.85-4.15 (m, 4H), 4.81 (bs, 1H), 5.83 (dt, 1H, J=38.1, 7.0), 6.75 (d, 2H, J=8.1), 6.99 (d, 2H, J=7.3), 7.63 (bs, 1H). $^{13}$C NMR (75.5 MHz, CDCl$_3$) δ=16.01 (d, $^3J_{C,P}$=6.0 Hz), 28.23, 39.79, 47.11, 63.49 (t, $^2J_{C,P}$=6.0 Hz), 115.43, 125.98, 127.13, 130.39, 155.68, 171.74. $^{31}$P NMR (121.5 MHz, CDCl$_3$) δ=5.61 (d, J=102.7 Hz). $^{19}$F NMR (282 MHz, CDCl$_3$) δ=−127.41 (dd, J=103.5, 39.1 Hz).

EXAMPLE 67

(3R)-[1-Fluoro-3-Hexadecanoylamino-4-(4-hydroxy-phenyl)-trans-but-1-enyl]-diethyl Phosphonate $^1$H NMR (300 MHz, CDCl$_3$) δ=0.87 (t, 3H, J=6.7), 1.20-1.35 (m, 30H), 1.50-1.63 (m, 2H), 2.12 (t, 2H, J=7.5), 2.69-2.95 (m, 2H), 3.84-4.18 (m, 4H), 5.11-5.26 (m, 1H), 5.89 (dt, 1H, J=38.6, 8.1), 6.05 (d, 1H, J=8.1), 6.75 (d, 2H, J=8.4), 6.99 (d, 2H, J=8.4). $^{13}$C NMR (300 MHz, CDCl$_3$) δ=14.07, 16.03 (dd, $^3J_{C,P}$=8.1, 4.0 Hz), 22.62, 25.59, 29.19, 29.30, 29.46, 29.65, 31.86, 36.56, 39.85, 45.86 (d, $^3J_{C,P}$=12.1 Hz), 63.55 (dd, $^2J_{C,P}$=10.1, 5.0 Hz), 115.46, 125.63 (d, $^1J_{C,P}$=28.21 Hz), 127.03, 130.28, 155.98, 172.94. $^{31}$P NMR (121.5 MHz, CDCl$_3$) δ=5.25 (d, J=101.1 Hz). $^{19}$F NMR (282 MHz, CDCl$_3$) δ=−126.62 (dd, J=101.5, 38.2 Hz).

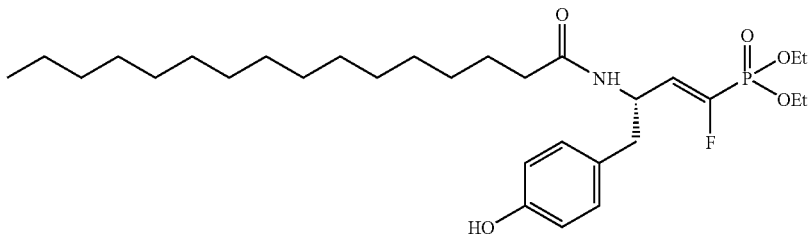

EXAMPLE 68

(3S)-[1-Fluoro-3-Hexadecanoylamino-4-(4-hydroxy-phenyl)-trans-but-1-enyl]-diethyl Phosphonate This product has similar spectral properties as its enantiomer.

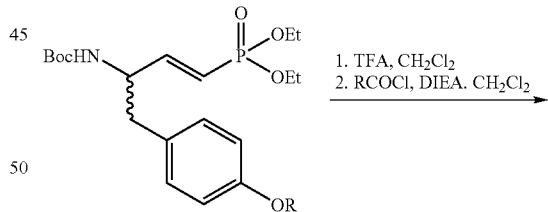

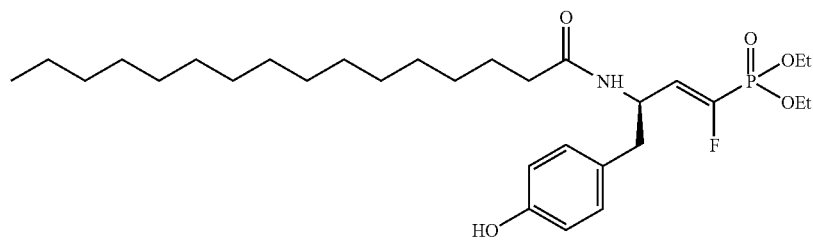

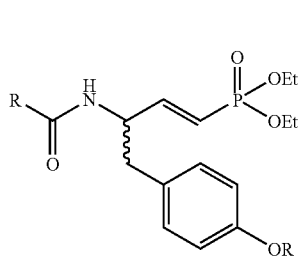

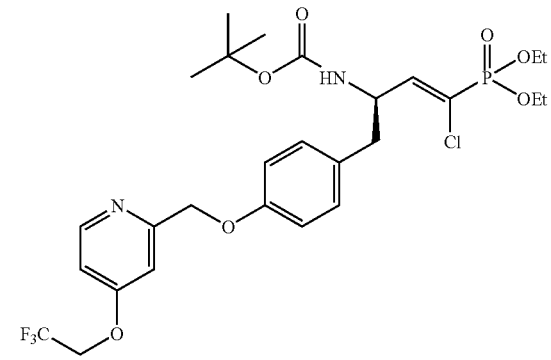

EXAMPLE 69

General Procedure for Boc Deprotection and Acylation. Synthesis of {4-[4-(O—R)-phenyl]-3-acylamino-trans-but-1-enyl}-diethyl Phosphonates To [4-[4-(O—R)-phenyl]-3-(N-Boc)-trans-but-1-enyl]-diethyl phosphonate (1.3 g, 2.0 mmol) in $CH_2Cl_2$ (10 ml) is added Trifluoroacetic acid (3 ml). The solution is stirred at room temperature under $N_2$ for 2 h. then evaporated to dryness to afford the free amine. To the amine dissolved in $CH_2Cl_2$ (50 ml) is added Hünigs base (6.0 mmol, 1.1 ml) and acid chloride (2.4 mmol) and the mixture stirred at room temperature under $N_2$. Upon completion, as judged by TLC, the solvent is evaporated under reduced pressure, and the residue subject to flash chromatography to afford the product as yellow oil (60-80% yield).

EXAMPLE 70

(3R)-(3-tert-Butoxycarbonylamino-1-chloro-4-{4-[4-(2,2,2-trifluoro-ethoxy)-pyridin-2-ylmethoxy]-phenyl}-trans-but-1-enyl)-diethyl Phosphonate $^1$H NMR (300 MHz, $CDCl_3$) δ=1.24-1.34 (m, 6H), 1.37 (s, 9H), 2.73-2.98 (m, 2H), 3.84-4.20 (m, 4H), 4.40 (q, 2H, J=7.9), 4.81 (bs, 1H), 5.12 (s, 2H), 6.70-6.85 (m, 2H), 6.89 (d, 2H, J=8.8), 7.08-7.12 (m, 3H), 8.45 (d, 1H, J=5.7). $^{13}$C NMR (75.5 MHz, $CDCl_3$) δ=16.11 (d, $^3J_{C,P}$=8.1 Hz), 28.20, 38.78, 52.03 (d, $^3J_{C,P}$=21.2 Hz), 63.00-63.33 (m, $^2J_{C,P}$; $^2J_{C,P}$), 70.16, 107.18, 109.10, 113.96, 114.79, 118.68 (d, $^1J_{C,P}$=205.5 Hz), 128.98, 130.52, 145.99 (d, $^2J_{C,P}$=6.0 Hz), 150.77, 159.50, 159.74, 164.12, 172.54. $^{31}$P NMR (121.5 MHz, $CDCl_3$) δ=10.02. $^{19}$F NMR (282 MHz, $CDCl_3$) δ=−74.04 (t, J=7.93 Hz, 3F). HRMS (ESI), M$^+$, Found: 623.1906. Calc for $C_{27}H_{36}ClF_3N_2O_7P$, 623.1901.

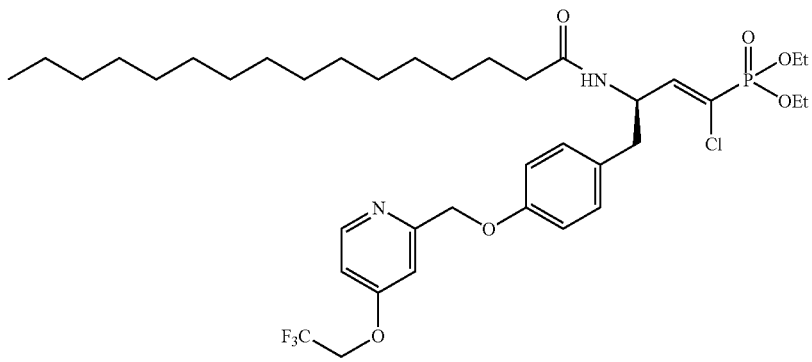

EXAMPLE 71

(3R)-(1-Chloro-3-Hexadecanoylamino-4-{4-[4-(2,2,2-trifluoro-ethoxy)-pyridin-2-ylmethoxy]-phenyl}-trans-but-1-enyl)-diethyl Phosphonate $^1$H NMR (300 MHz, CDCl$_3$) δ=0.86 (t, 3H, J=6.7), 1.19-1.36 (m, 30H), 1.47-1.59 (m, 2H), 2.10 (t, 2H, J=7.5), 2.80-2.97 (m, 2H), 3.88-4.17 (m, 4H), 4.41 (q, 2H, J=7.9), 5.12 (apparent s, 3H), 5.93 (d, 1H, J=7.69), 6.72-6.80 (m, 2H), 6.90 (d, 2H, J=8.6), 7.12 (apparent d, 3H, J=8.8), 8.46 (d, 1H, J=5.7). $^{13}$C NMR (300 MHz, CDCl$_3$) δ=14.05, 16.11 (d, $^3J_{C,P}$=8.1 Hz), 20.97, 22.62, 25.51, 28.87, 29.19, 29.30, 29.43, 29.59, 31.86, 36.51, 38.57, 49.45 (d, $^3J_{C,P}$=16.1 Hz), 63.78 (q, $^2J_{C,P}$=6.0 Hz), 64.85 (q, $^2J_{C,F}$=36.26), 70.11, 107.23, 109.08, 114.79, 120.84 (d, $^1J_{C,P}$=187.4 Hz), 129.00, 130.47, 145.74 (d, $^2J_{C,P}$=18.1 Hz), 150.77, 157.13, 159.66, 164.12, 172.51. $^{31}$P NMR (121.5 MHz, CDCl$_3$) δ=9.80. $^{19}$F NMR (282 MHz, CDCl$_3$) δ=−74.04 (t, J=7.93 Hz, 3F).

EXAMPLE 72

(3R)-(3-tert-Butoxycarbonylamino-1-fluoro-4-{4-[4-(2,2,2-trifluoro-ethoxy)-pyridin-2-ylmethoxy]-phenyl}-trans-but-1-enyl)-diethyl Phosphonate $^1$H NMR (300 MHz, CDCl$_3$) δ=1.24 (t, 3H, J=7.0), 1.30 (t, 3H, J=7.0), 1.87 (s, 9H), 2.65-2.97 (m, 2H), 3.84-4.14 (m, 4H), 4.38 (q, 2H, J=7.9), 4.79 (bs, 1H), 5.10 (s, 2H), 5.84 (dt, 1H, J=38.6, 7.0), 6.77 (dt, 1H, J=5.7, 2.4), 6.88 (d, 2H, J=8.8), 7.09 (apparent d, 3H, J=8.6), 8.43 (d, 1H, J=5.7). $^{13}$C NMR (75.5 MHz, CDCl$_3$) δ=16.04 (d, $^3J_{C,P}$=6.1 Hz), 28.18, 38.79, 47.25, 63.10 (dd, $^2J_{C,P}$=12.1, 6.1) 64.78 (q, $^2J_{C,F}$=36.26), 70.11, 107.15, 109.05, 114.69, 125.75 (d, $^1J_{C,P}$=32.2 Hz), 129.19, 130.44, 150.74, 154.78, 157.02, 159.69, 164.04, 171.76. $^{31}$P NMR (121.5 MHz, CDCl$_3$) δ=5.59 (d, J=99.5). $^{19}$F NMR (282 MHz, CDCl$_3$) δ=−127.22 (dd, J=105.65, 40.14, 1F), −74.05 (t, J=7.93 Hz, 3F).

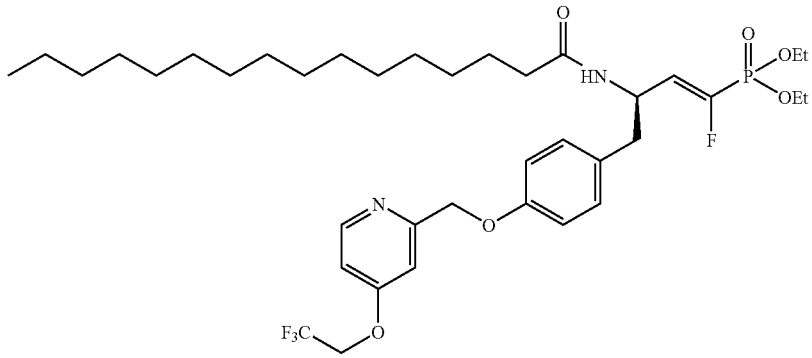

EXAMPLE 73

(3R)-(1-Fluoro-3-Hexadecanoylamino-4-{4-[4-(2,2,2-trifluoro-ethoxy)-Pyridin-2-ylmethoxy]-phenyl}-trans-but-1-enyl)-diethyl Phosphonate $^1$H NMR (300 MHz, CDCl$_3$) δ=0.85 (t, 3H, J=6.5), 1.16-1.33 (m, 30H), 1.48-1.60 (m, 2H), 2.09 (t, 2H, J=7.6), 2.70-2.99 (m, 2H), 3.85-4.15 (m, 4H), 4.40 (q, 2H, J=7.9), 5.10 (apparent s, 3H), 5.87 (dt, 1H, J=38.7, 8.3), 6.19 (d, 1H, J=8.14), 6.78 (dd, 1H, J=5.60, 2.6), 6.88 (d, 2H, J=8.8), 7.10 (apparent d, 3H, J=8.6), 8.43 (d, 1H, J=5.7). $^{13}$C NMR (300 MHz, CDCl$_3$) δ=14.02, 16.04 (d, $^3J_{C,P}$=6.1 Hz), 22.59, 25.53, 29.16, 26.24, 29.30, 29.41, 29.59, 31.81, 36.54, 39.71, 45.45 (dd, $^3J_{C,P}$=12.1, 4.0 Hz), 63.25 (dd, $^2J_{C,P}$=16.1, 4.0 Hz), 65.03 (t, $^2J_{C,F}$=36.3), 70.08, 107.18, 109.02, 114.66, 125.40 (dd, $^1J_{C,P}$=28.2, 4.0 Hz), 129.30, 130.42, 150.74, 157.02, 159.66, 164.07, 172.08, 172.43. $^{31}$P NMR (121.5 MHz, CDCl$_3$) δ=5.11 (d, J=99.5). $^{19}$F NMR (282 MHz, CDCl$_3$) δ=−126.55 (dd, 1F, J=38.64, 100.08), −74.06 (t, 3F, J=7.93 Hz). HRMS (ESI), M$^+$, Found: 745.3945. Calc for C$_{38}$H$_{58}$F$_4$N$_2$O$_6$P, 745.3969.

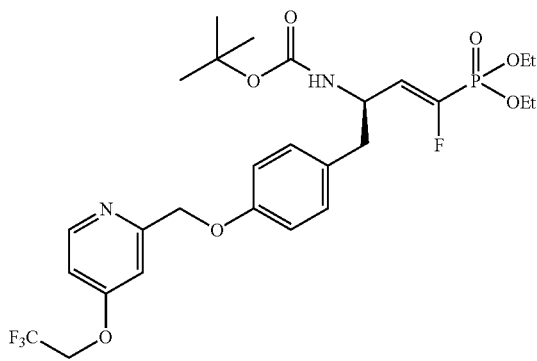

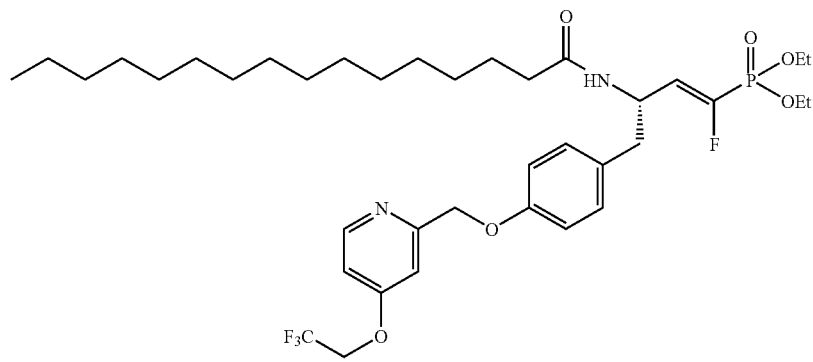

EXAMPLE 74

(3S)-(1-Fluoro-3-Hexadecanoylamino-4-{4-[4-(2,2,2-trifluoro-ethoxy)-pyridin-2-ylmethoxy]-phenyl}-trans-but-1-enyl)-diethyl Phosphonate This product has similar spectral properties as its enantiomer.

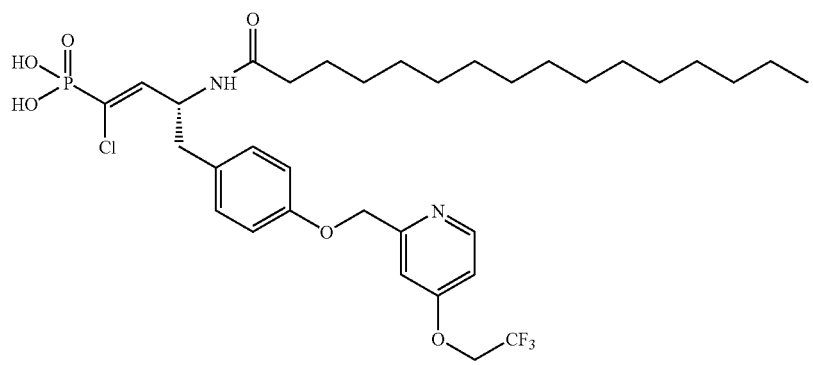

EXAMPLE 75

(3R)-(1-Chloro-3-Hexadecanoylamino-4-{4-[4-(2,2,2-trifluoro-ethoxy)-pyridin-2-ylmethoxy]-phenyl}-trans-but-1-enyl)-phosphonic Acid (vpc53048)

$^1$H NMR (300 MHz, CD$_3$OD:TFA) δ=0.67 (t, 3H, J=6.3), 1.05 (apparent s, 24H), 1.24-1.36 (m, 2H), 1.90 (q, 2H, J=7.0), 2.58-2.73 (m, 2H), 4.83 (q, 2H, J=7.9), 5.20 (s, 2H), 6.40-6.49 (m, 1H), 6.82 (d, 2H, J=8.4), 7.02 (d, 2H, J=8.4), 7.42 (dd, 1H, J=6.9, 2.8), 7.55 (d, 1H, J=2.2), 8.51 (d, 1H, J=6.8). $^{13}$C NMR (75.5 MHz, CD$_3$OD:TFA) δ=14.44, 23.76, 26.97, 30.25, 30.46, 30.62, 30.81, 33.08, 37.11, 39.76, 66.68, 67.55 (d, $^2J_{C,F}$=38.3), 112.67, 113.85, 116.01, 124.83 (d, $^1J_{C,P}$=189.37 Hz), 131.93, 132.62, 141.95 (d, $^2J_{C,P}$=20.1 Hz), 159.73, 160.27, 170.12, 175.60. $^{31}$P NMR (121.5 MHz, CD$_3$OD:TFA) δ=6.71. $^{19}$F NMR (282 MHz, CD$_3$OD:TFA) δ=−75.73 (t, J=7.93 Hz, 3F). HRMS (ESI), M$^+$, Found: 705.3086. Calc for C$_{34}$H$_{50}$ClF$_3$N$_2$O$_6$P, 705.3047.

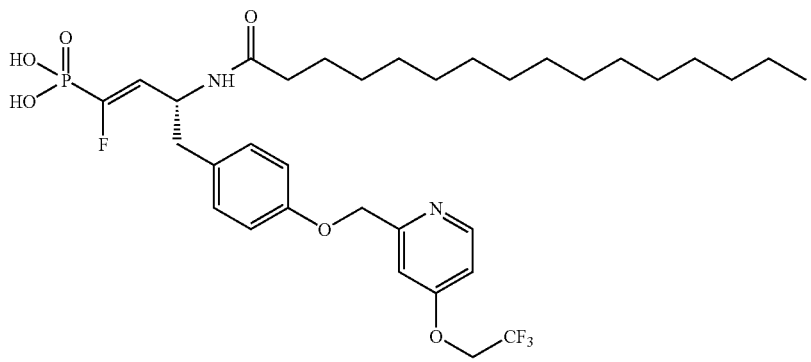

EXAMPLE 76

(3R)-(1-Fluoro-3-Hexadecanoylamino-4-{4-[4-(2,2,2-trifluoro-ethoxy)-pyridin-2-ylmethoxy]-phenyl}-trans-but-1-enyl)-phosphonic Acid (vpc52298)

$^1$H NMR (300 MHz, CD$_3$OD:TFA) δ=0.61 (t, 3H, J=6.5), 0.99 (apparent s, 24H), 1.17-1.29 (m, 2H), 1.82 (t, 2H, J=7.3), 2.38-2.66 (m, 2H), 5.14 (s, 2H), 5.47 (dt, 1H, J=38.9, 7.9), 6.76 (d, 2H, J=8.1), 6.95 (d, 2H, J=8.1), 7.35 (dd, 1H, J=5.7), 7.49 (s, 1H), 8.44 (d, 1H, J=6.2). $^{13}$C NMR (75.5 MHz, CD$_3$OD:TFA) δ=14.44, 23.76, 26.97, 30.25, 30.46, 30.62, 30.78, 33.08, 37.11, 40.88, 66.71, 67.54 (d, $^2J_{C,F}$=38.3), 112.65, 113.85, 115.96, 124.95 (d, $^1J_{C,P}$=38.3 Hz), 131.88, 132.84, 144.80, 157.49, 160.29, 169.59, 175.44. $^{31}$P NMR (121.5 MHz, CD$_3$OD:TFA) δ=2.35 (d, 1P, J=109.2).

$^{19}$F NMR (282 MHz, CD$_3$OD:TFA) δ=−127.54 (dd, 1F, J=108.48, 39.14), −75.73 (t, 3F, J=7.93 Hz). HRMS (ESI), M$^+$, Found: 689.3335. Calc for C$_{34}$H$_{50}$F$_4$N$_2$O$_6$P, 689.3343.

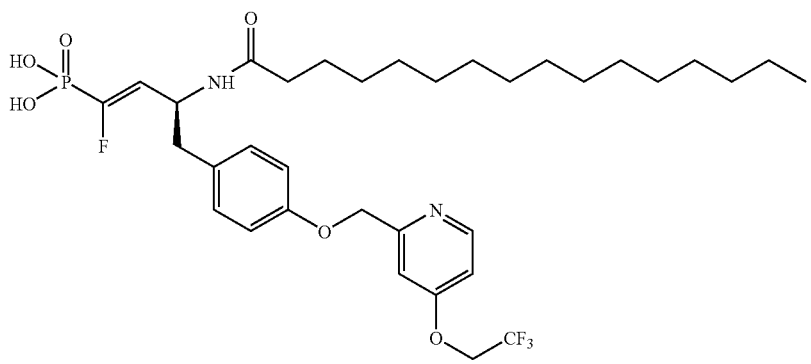

EXAMPLE 77

(3S)-(1-Fluoro-3-Hexadecanoylamino-4-{4-[4-(2,2,2-trifluoro-ethoxy)-pyridin-2-ylmethoxy]-phenyl}-trans-but-1-enyl)-phosphonic acid (vpc52300)

This product has similar spectral properties as its enantiomer.

EXAMPLE 78

Epidermoid Carcinoma

Figure 2:
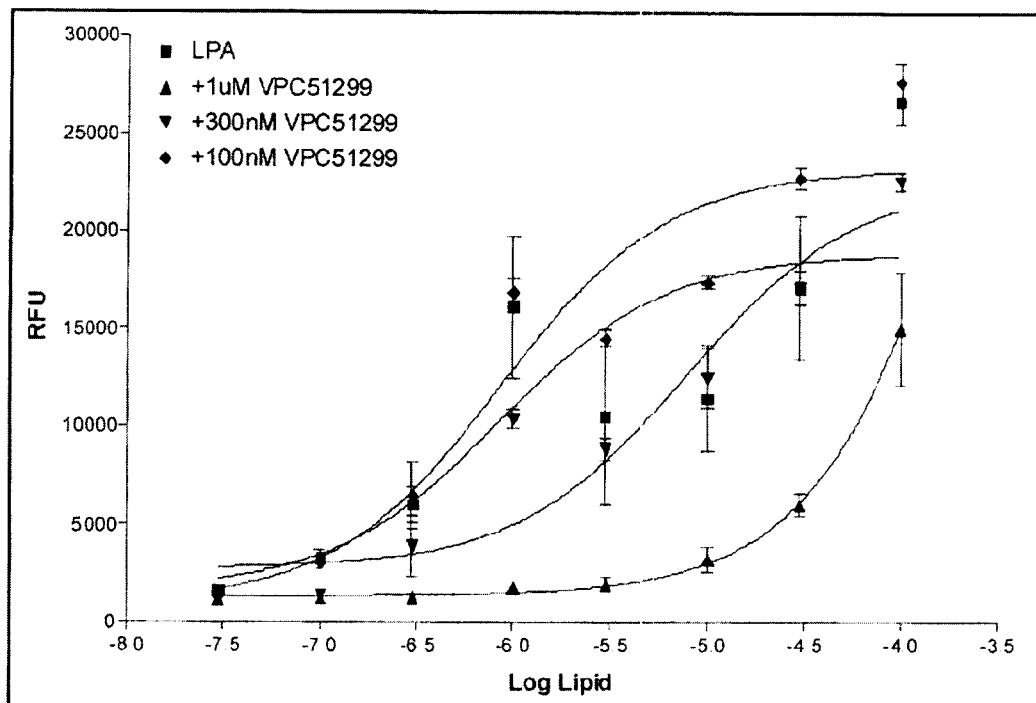
FIG. 2 is a graphic representation of LPA-driven calcium mobilization in A431 cells.

Human epidermoid carcinoma A431 cells, which mobilize calcium via a combination of LPA$_1$ and LPA$_3$ receptors, were loaded with a calcium-sensing fluorescent dye, and challenged with 1-oleoyl LPA in the presence of the indicated concentrations of VPC51299. Results are illustrated in FIG. 2.

EXAMPLE 79

LPA Inhibition

Figure 3:
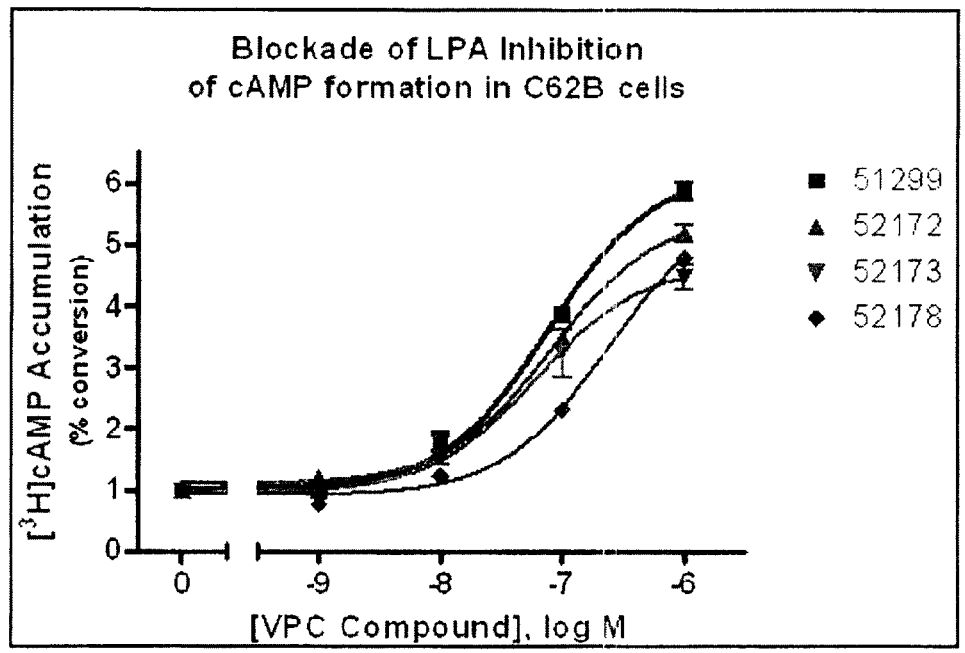
FIG. 3 is a graphic representation of LPA-driven adenylyl cyclase inhibition in C6 glioma cells.

Rat glioma C62B cells accumulate cAMP in response to isoproterenol, and this stimulation of adenylyl cyclase is blocked by LPA. As shown, the LPA inhibition of adenylyl cyclase activation is relieved by addition of VPC51299, VPC52172, VPC52173, and VPC52178, all in a dose-dependent manner. Results are illustrated in FIG. 3.

EXAMPLE 80

Melanoma Cell Migraton

Figure 4:
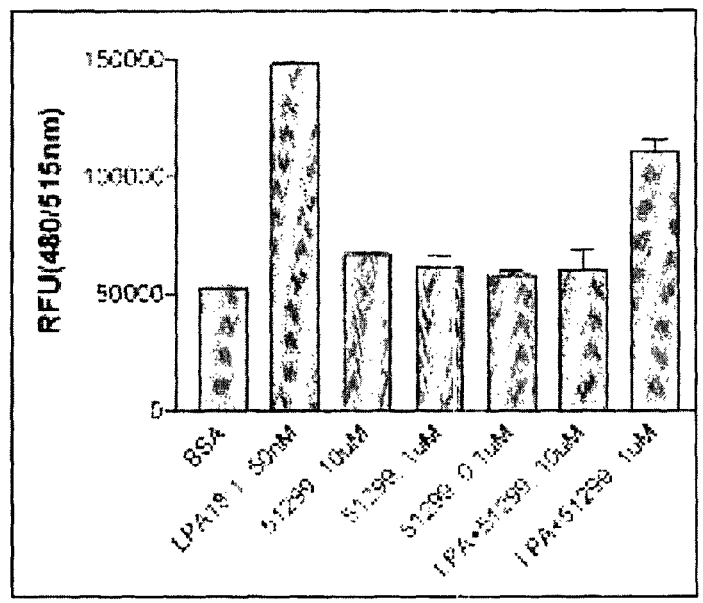
FIG. 4 illustrates LPA-driven cell migration in A2058 cells.

Human melanoma A2058 cells (1×10$^5$) were placed in the upper portion of a modified Boydon chamber. The indicated compounds were placed in the lower chamber and after four hours at 37° C., cells were collected from the underside of the membrane (8 μm pore size, Matrigel® coated) and their mass determined. Results are illustrated in FIG. 4.

Figure 5:
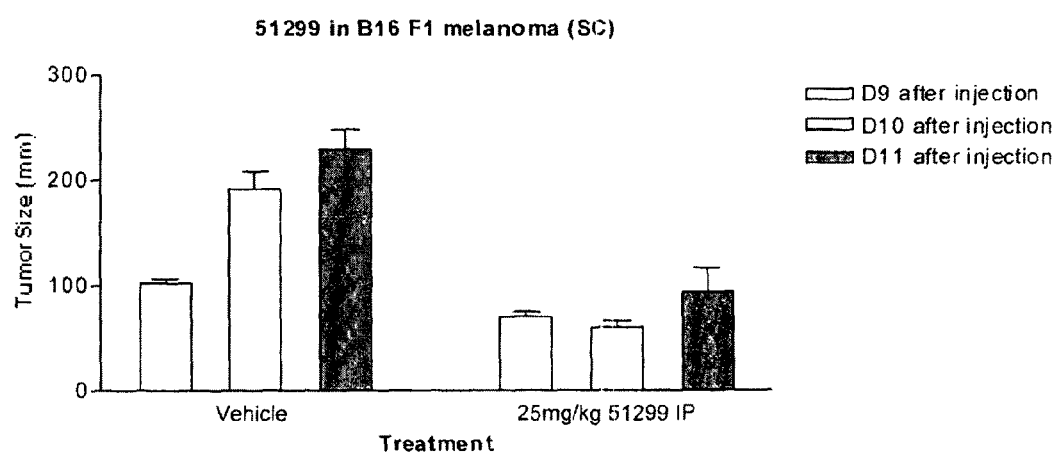
FIG. 5, FIGS. 6A and 6B illustrate melanoma tumor growth.
Figure 6A:
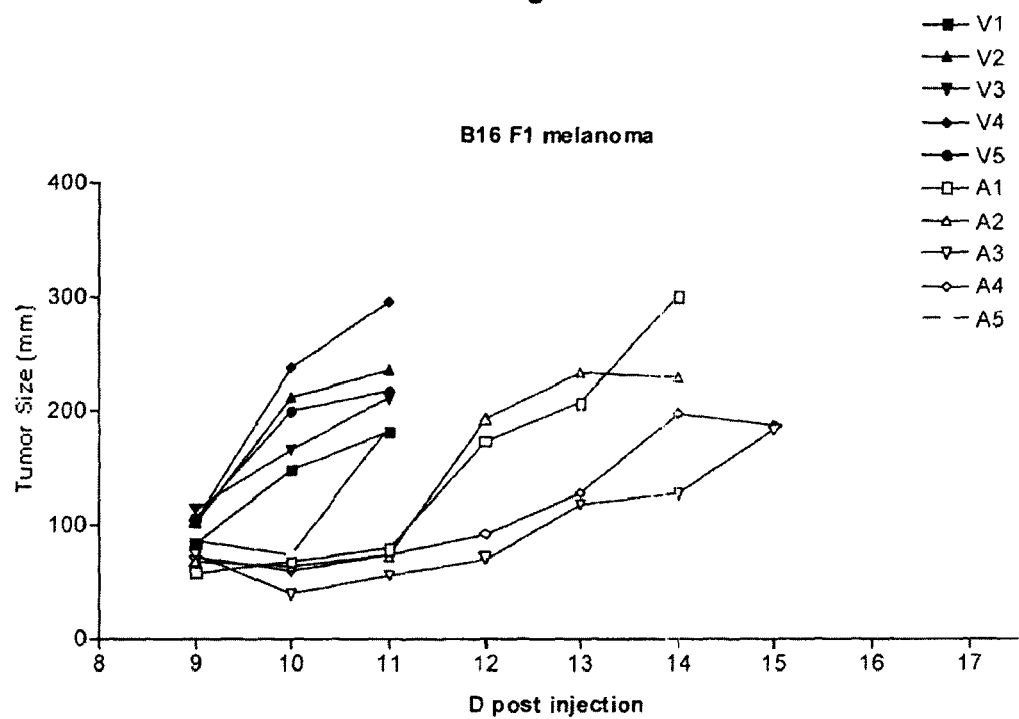
Figure 6B:
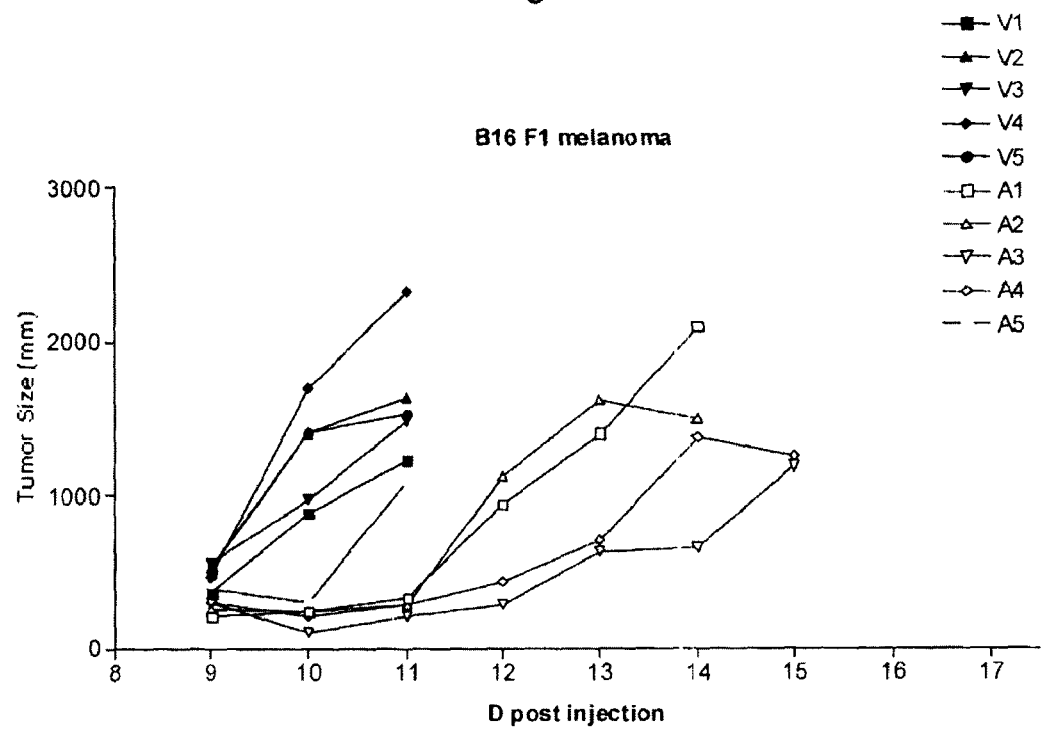
Figure 7:
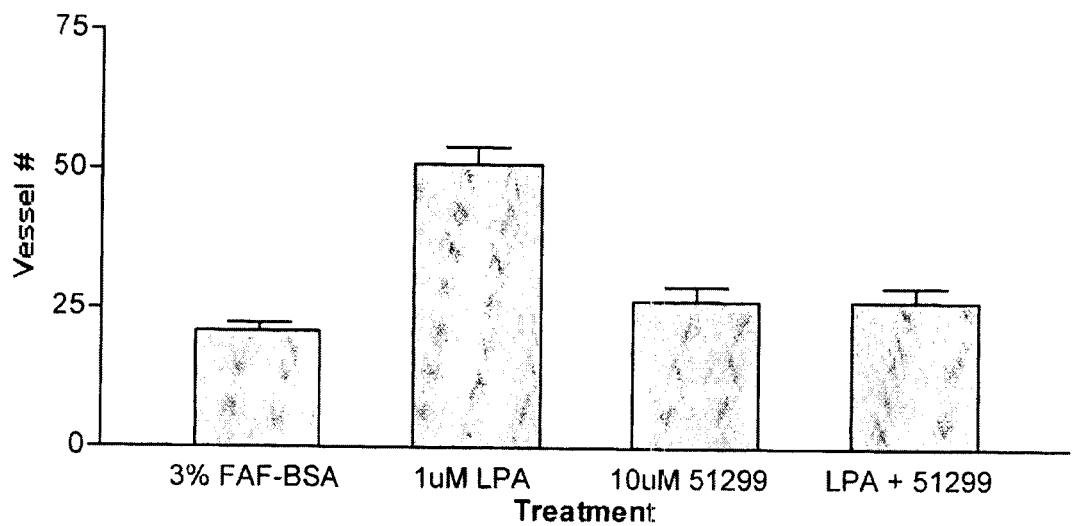
FIG. 7 illustrates the quantification of the extent of angiogenesis in a tumor.
Figure 8A:
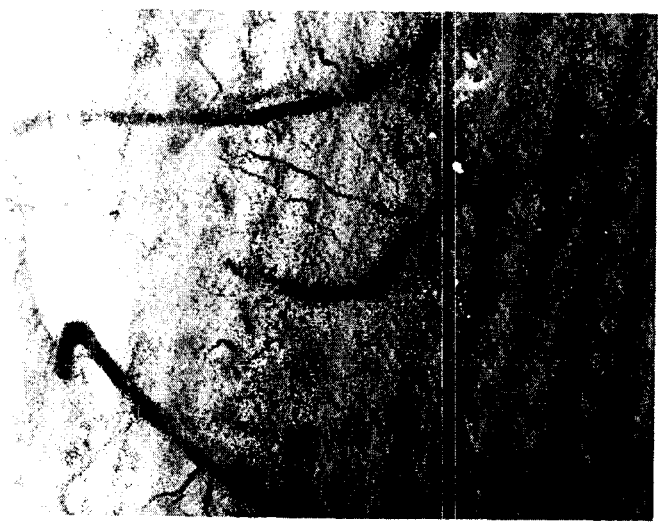
FIGS. 8A-8D illustrate the ability of the disclosed compounds to prevent angiogenesis in tumors.
Figure 8B:
Figure 8C:
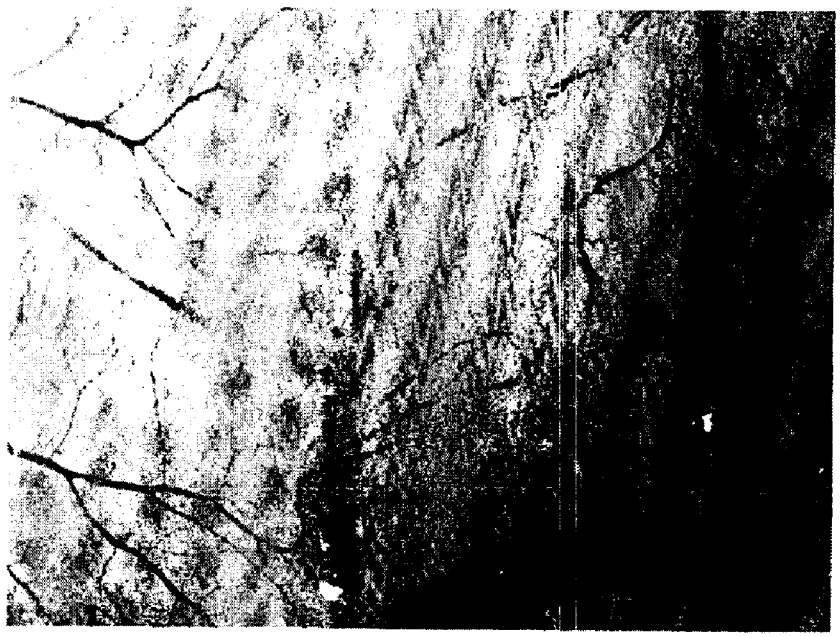
Figure 8D:

Mice were injected s.c. with 400,000 B16F1 melanoma cells on day 0; test compound VPC51299/vehicle is injected once daily, i.p., 25 mg/kg, begun on day 7, n=5 C57BL/6 (female, 8-9 weeks) mice group. Rules dictate euthanizing mice when tumor size exceeds 225 mm³ (tumor volume=(L× W×W)/2: day 11 for vehicle treatment). Tumors first palpable on day 8. Results illustrated in FIG. 5 and FIGS. 6A-6B.

EXAMPLE 81

CAM Assay: (Chorioallantoic Membrane)

Fertilized chicken eggs were windowed on day 3 of embryonic development to expose the chorioallantoic membrane. After a further 4 days of incubation, a 5 mm diameter plug of filter paper (Whatman GF/C) was applied to the membrane and soaked with 20 microliters of either vehicle (3% fatty acid free bovine serum albumin (FAF_BSA) or compound dissolved in vehicle at the indicated concentration. Application of the solutions was repeated daily for 3 days (embryonic days 7-9). On embryonic day 10, filter paper plugs were removed, the underlying membrane excised and fixed in formalin and examined microscopically. Quantification was achieved by counting the number of small diameter vessels that run perpendicular to the disk image. Results are illustrated in FIG. 7 and FIGS. 8A-8D.

EXAMPLE 82

Neuropathic Pain

The chronic constriction injury (CCI) model of neuropathic pain (Bennett and Xie, *Pain*, 33 p 87-107 (1988)) was used to assess the efficacy of test compound VPC51299 in relieving thermal hyperalgesia and mechanical allodynia. Adult male Sprague Dawley rats were anesthetized and their sciatic nerves exposed at the level of mid-thigh. Four loose ligations of chromic gut suture were placed around the sciatic nerve and the wound was closed. For sham surgeries, the sciatic nerve was mobilized and the wound closed without ligation. The animals' responses to mechanical and thermal stimuli were assessed prior to CCI and at days 1, 3, 5, 7, and 14 after CCI.

Figure 9A:
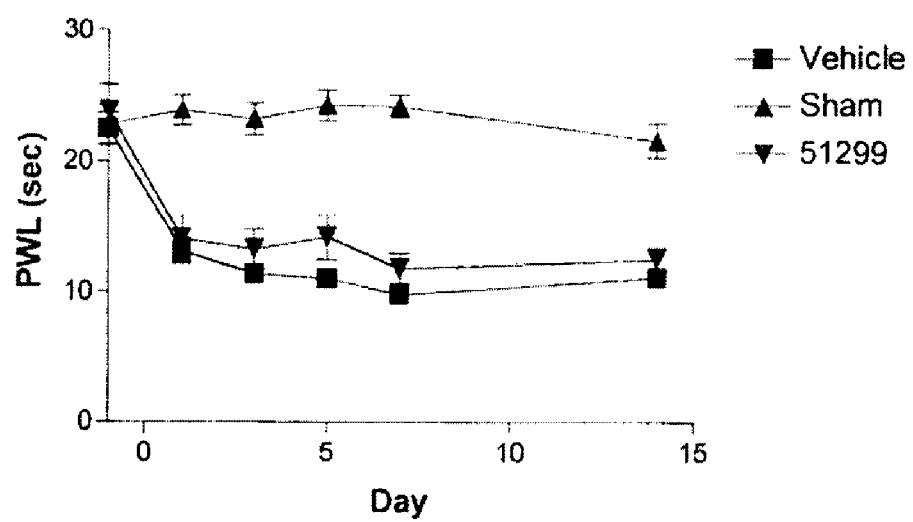
FIGS. 9A-9C illustrate the effect of the disclosed compounds on tactile allodynia and thermal hyperalgesia in rats wherein ligatures have been placed on the sciatic nerve.

Thermal hyperalgesia was measured using a Plantar Test Apparatus (IITC Inc, Woodland Hills, Calif.). Rats were placed on a warmed glass surface, allowed to acclimate, and a thermal stimulus was applied to the plantar surface of the hind paw. Paw withdrawal latency (PWL) is defined as the time from stimulus application to paw withdrawal. Results are illustrated in FIG. 9A.

Figure 9B:
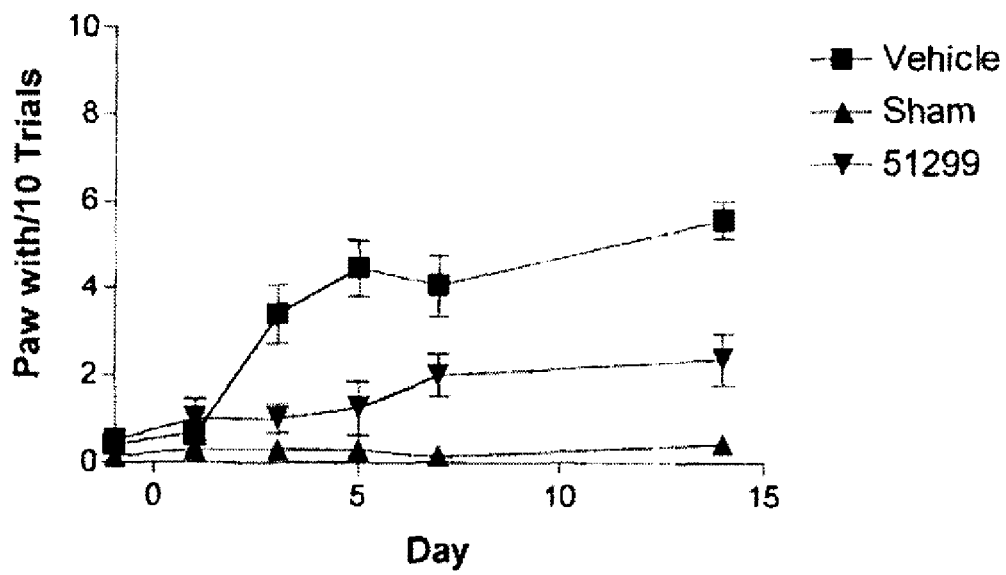
Figure 9C:
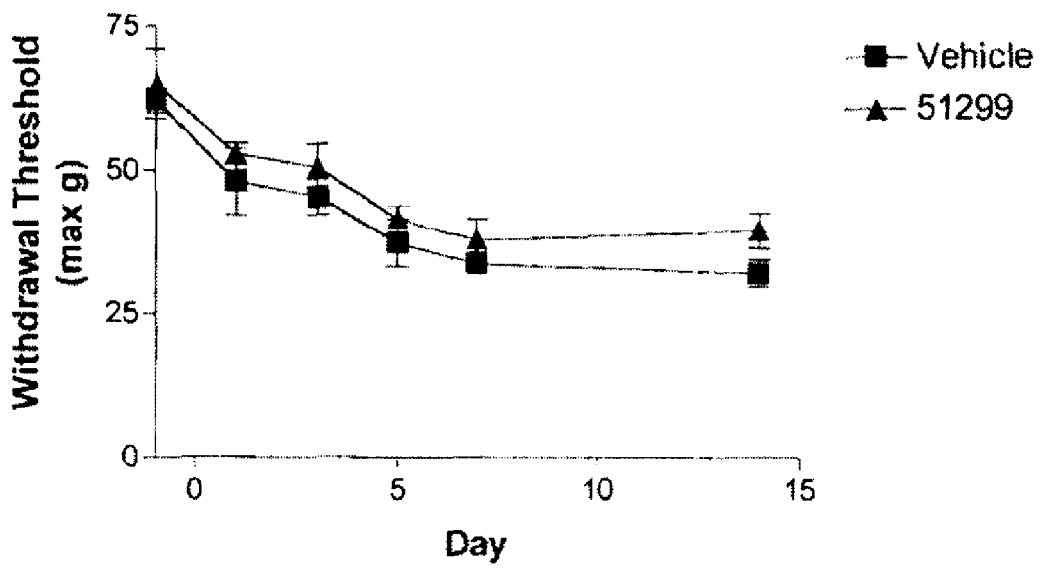

Mechanical allodynia was measured two ways. First, a size 5.18 Von Frey monofilament (corresponding to 15.0 g.) was applied to the plantar surface of the hind paw (Touch Test Sensory Evaluator Kit from Stoelting Co., Wood Dale, Ill.). The number of paw withdrawals out of 10 three second trials was recorded. Results are illustrated in FIG. 9B. Second, the maximum withdrawal threshold was assessed using an electronic von Frey Anesthesiometer (IITC Inc, Woodland Hills, Calif.). Force was applied to the plantar surface of the hindpaw until the rat withdrew its paw. The maximum force applied to the paw before withdrawal was recorded. Results are illustrated in FIG. 9C.

These experiments indicate that VPC51299 was effective in relieving some of the thermal hyperalgesia and mechanical allodynia associated with CCI. On day 5, after 5 days of treatment, rats receiving VPC51299 withdrew their paw 3.1 seconds slower than vehicle treated rats, lifted their paw 3.2 fewer times (out of 10 trials) than vehicle treated rats, and had a withdrawal threshold 4.0 g. higher than vehicle treated rats.

EXAMPLE 83

HM7 Tumor Propagation 45 mice were inoculated with 5 million HM7 cells in PBS, in a 0.2 ml volume per mouse, in the lower right dorsal flank area, SQ. Once the tumors reached ~200 mm3, animals were randomly divided into 3 groups of 10, including vehicle (2% hydroxypropyl beta cyclodextrin), oral dose of 0.5 ml, FTY720 (10 mg/kg) oral dose of 0.5 ml, and compound 51299 (15 mg/kg) SQ dose of 0.1 ml.

EXAMPLE 84

Micro-Computed Tomographic Angiography

Animals received a 0.05 ml i.p. injection of heparin 10 minutes before euthanization by inhalation of carbon dioxide. The thoracic cavity was opened, an incision was made in the apex of the heart, and a polyethylene cannula (id 0.58 mm, od 0.97 mm) was passed through the left ventricle and secured in the ascending aorta with 5-0 silk suture. A 17 ml solution of 0.1 mM sodium nitroprusside in 0.9% saline was perfused at a rate of 6 ml/min to provide a state of maximum vasodilatation and to remove blood. MICROFIL™ (Carver, Mass.), a commercially available lead chromate latex, was prepared as recommended by the manufacturer and perfuse at a rate of 2 ml/min for 17 ml. The infused latex mixture was allowed to polymerize at room temperature for sixty minutes before dissection of tissues of interest. Dissected tumors were immersed in 10% neutral buffered formalin.

The tumors were then imaged with a µCT40 (SCANCO Medical, Basserdorf, Switzerland) x-ray micro-computed tomography (micro-CT) system. The tumors were imaged with soybean oil as the background media. The micro-CT images were generated by operating the x-ray tube at an energy level of 45 kV, a current of 177 µA and an integration time of 450 ms. Axial images were obtained at an isotropic resolution of 16 µm.

The vascular network and tumor were extracted by a series of image processing steps. An intensity threshold of 1195 Houndsfield Units (HU) and morphological filtering (erosion and dilation) were applied to the volumetric micro-ct image data to extract the vascular volume (VV). The tumor volume (TV) was extracted from the background in similar fashion with an intensity threshold of −8 HU. Vessel density (VV/TV) was determined from the ratio of VV to TV. The vascular and tumor intensity thresholds were determined by visual inspection of the segmentation results from a subset of samples. Vessel size estimates were based on a skeletonization algorithm that employs boundary-seeded and single-seeded distance transform techniques (Zhou, Y. et al., IEEE Trans. Visualization and Computer Graphics, 1999; 5[3]: 196-209). Computations were performed by an in-house image analysis algorithm written in C++ and Python that employed the AVW image processing software library (AnalyzeDirect Inc., Lenexa, Kans.). Three-dimensional (3D) surface renderings were created from the micro-CT data with the use of Analyze 6.0 (AnalyzeDirect Inc., Lenexa, Kans.), an image analysis software package.

Figure 10B:
FIGS. 10a-10ii, 11a-11mm, and 12a-12nn illustrate the effect of a test compound on tumor growth.
Figure 10:
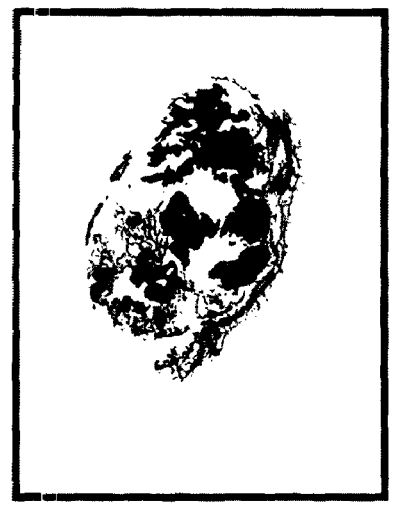
Figure 10A:
Figure 10C:
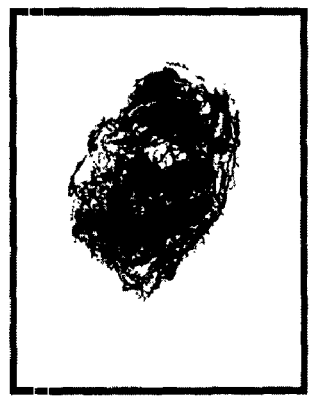
Figure 10F:
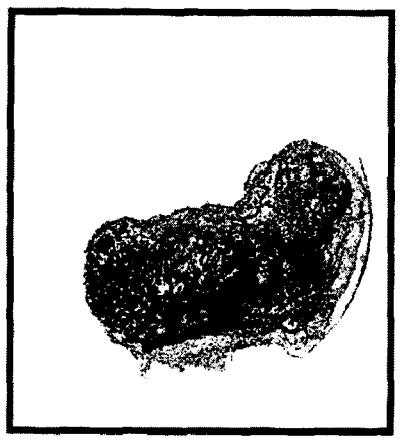
Figure 10H:
Figure 10E:
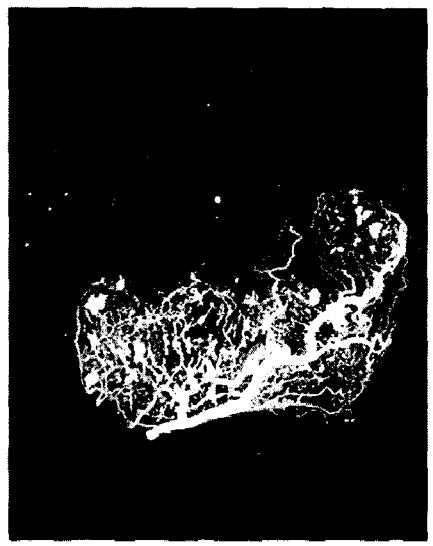
Figure 10G:
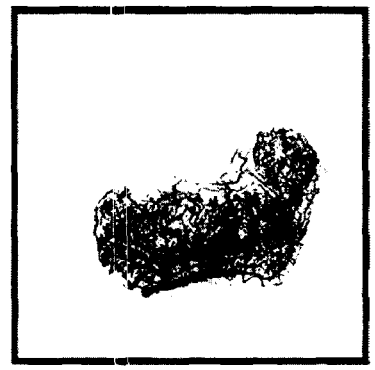
Figure 10J:
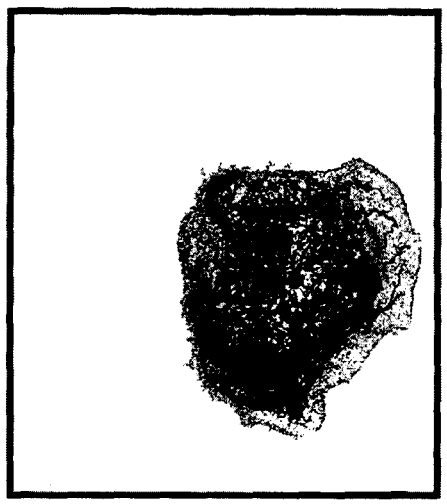
Figure 10L:
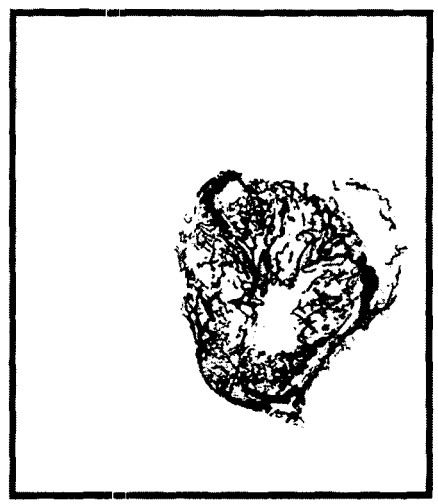
Figure 10I:
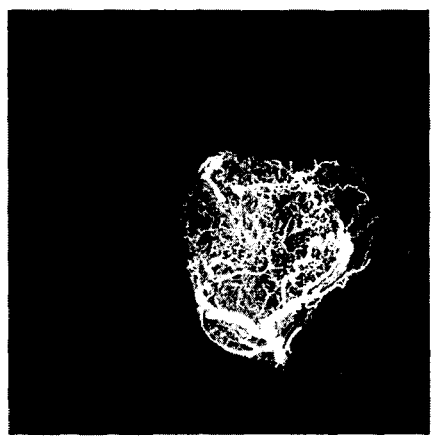
Figure 10K:
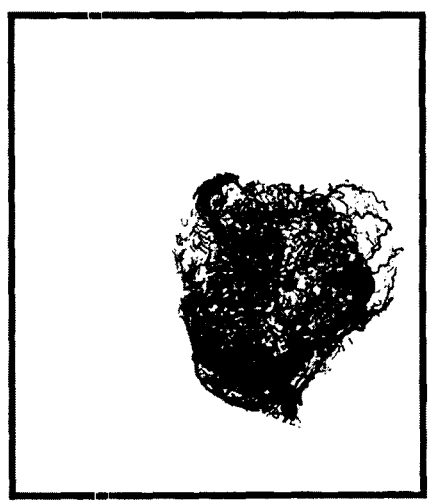
Figure 10N:
Figure 10O:
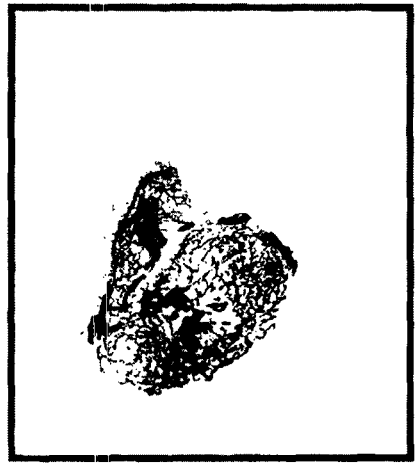
Figure 10M:
Figure 10O:
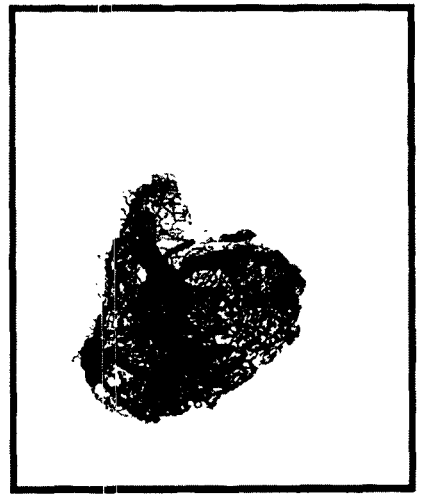
Figure 10Q:
Figure 10S:
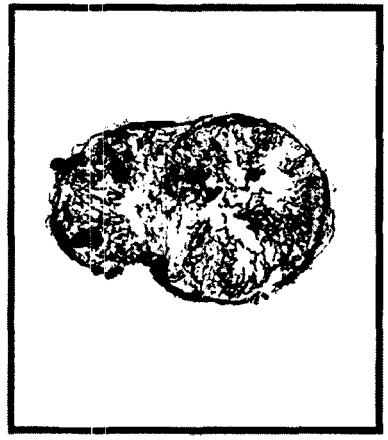
Figure 10P:
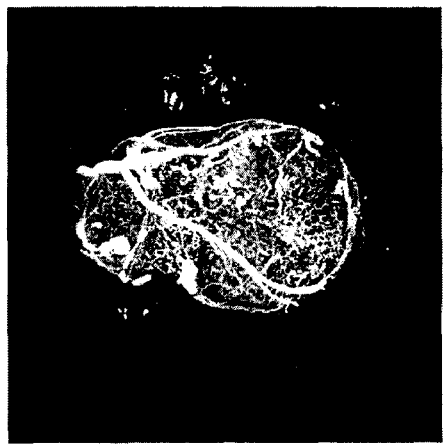
Figure 10R:
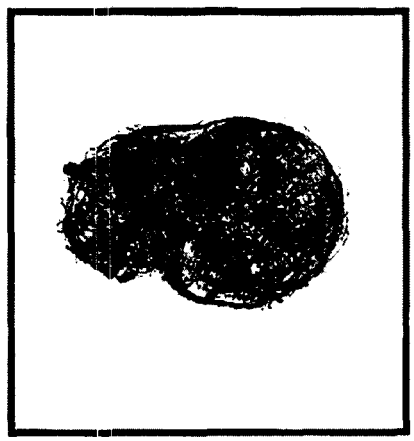
Figure 10U:
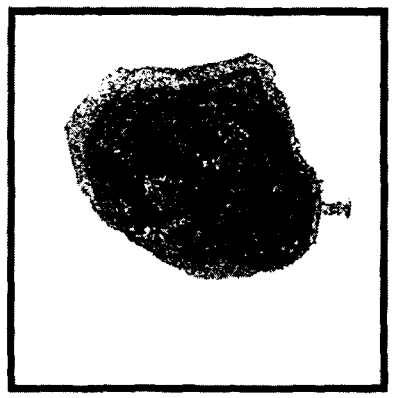
Figure 10W:
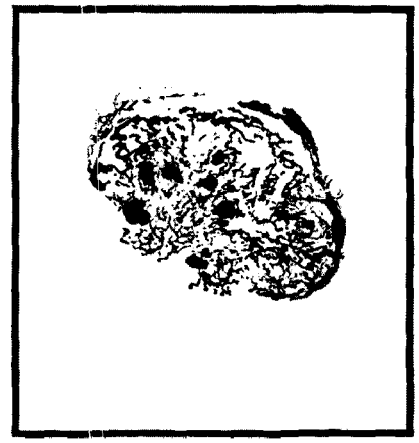
Figure 10T:
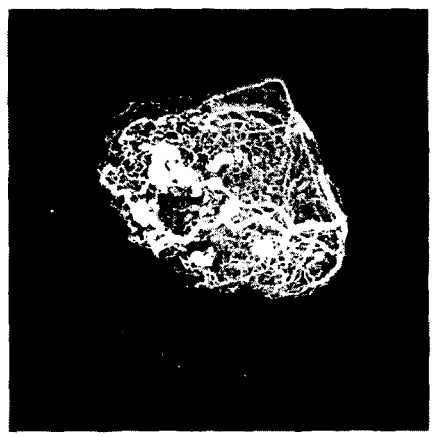
Figure 10V:
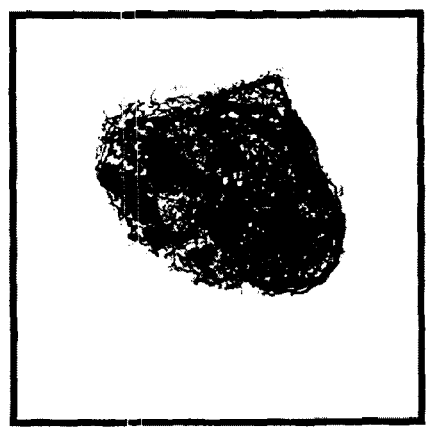
Figure 10Y:
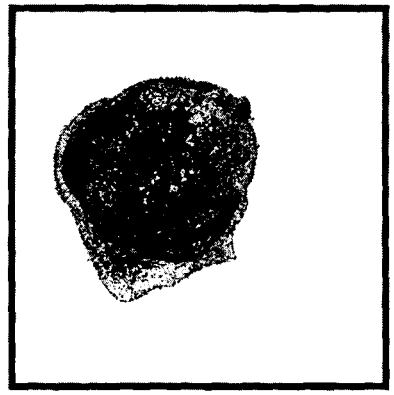
Figure 10A:
Figure 10X:
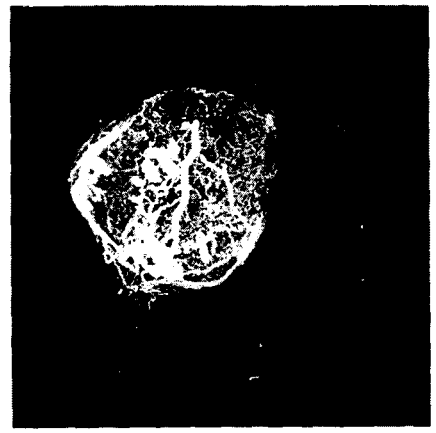
Figure 10Z:
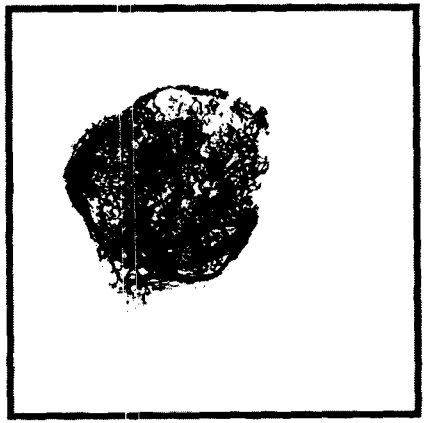
Figure 10C:
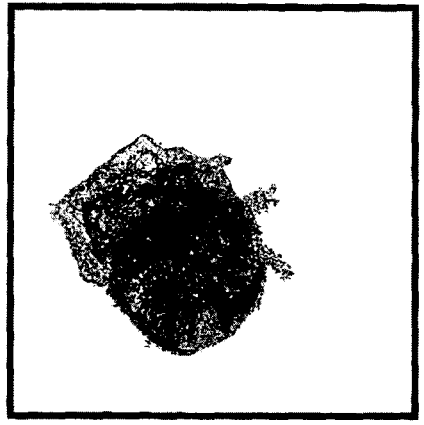
Figure 10E:
Figure 10:
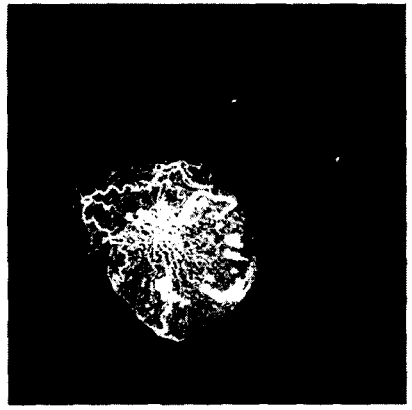
Figure 10D:
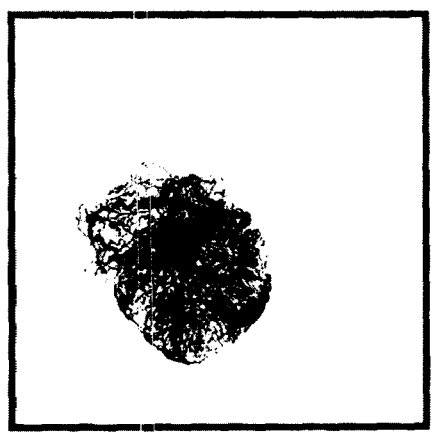
Figure 10G:
Figure 10I:
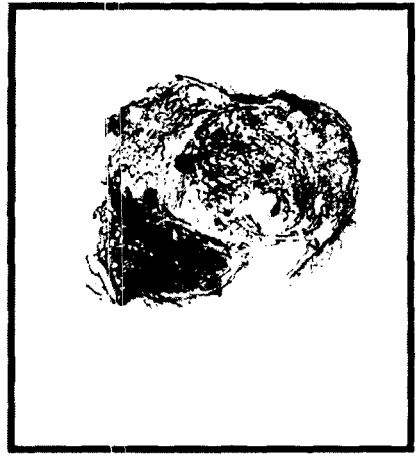
Figure 10F:
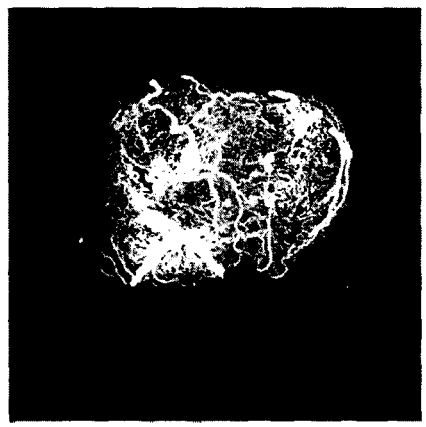
Figure 10H:
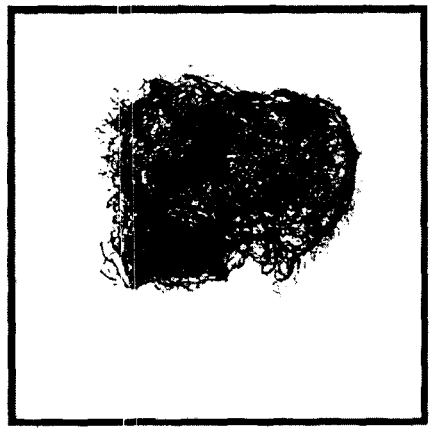
Figure 11F:
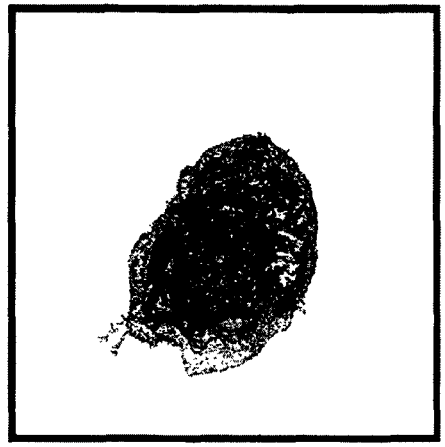
Figure 11H:
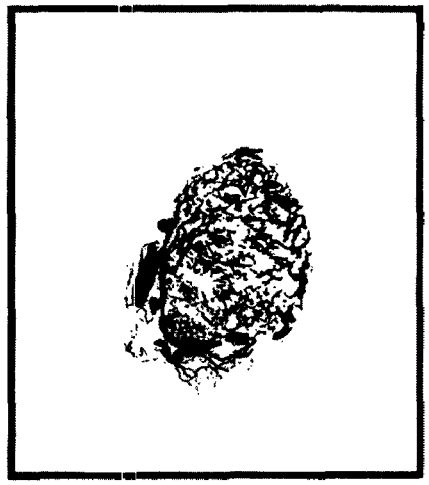
Figure 11E:
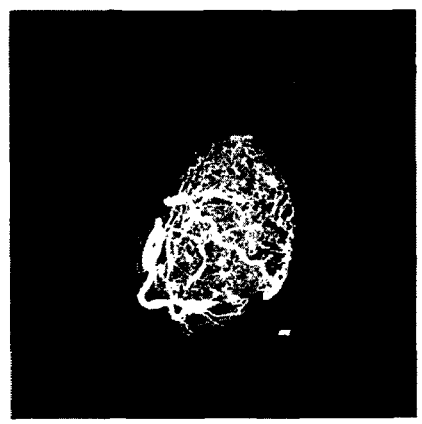
Figure 11G:
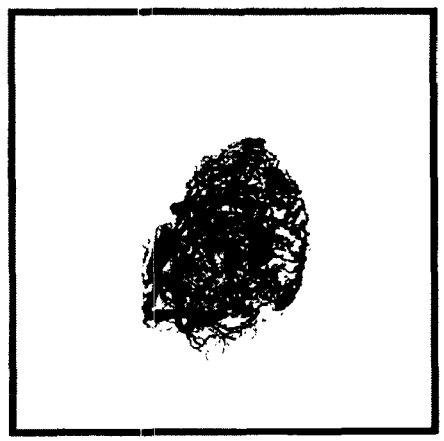
Figure 11J:
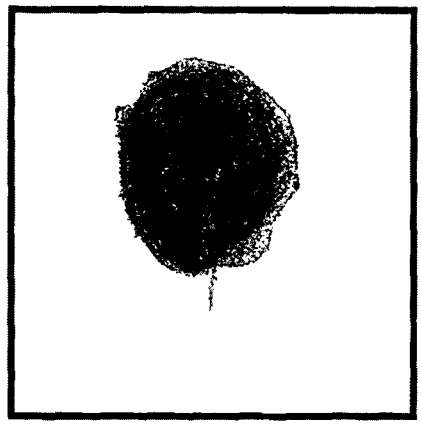
Figure 11L:
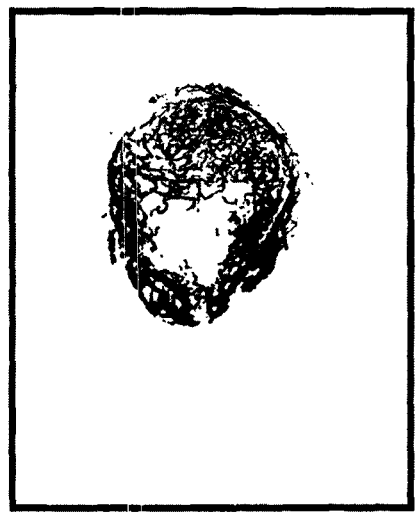
Figure 11I:
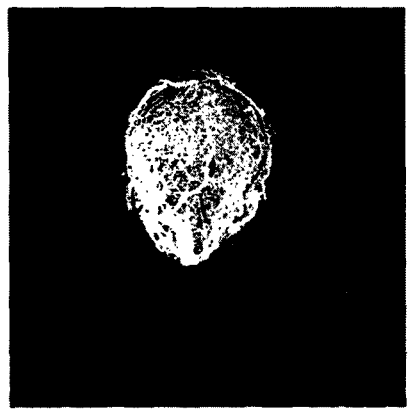
Figure 11K:
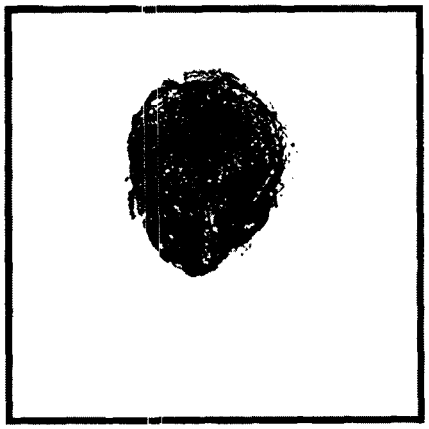
Figure 11N:
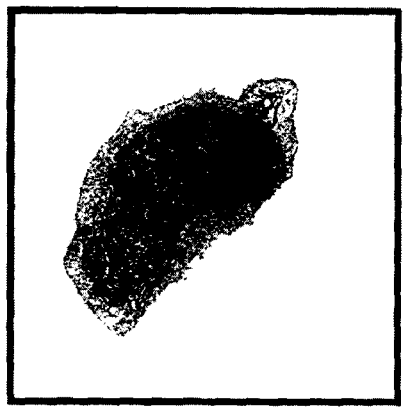
Figure 11P:
Figure 11M:
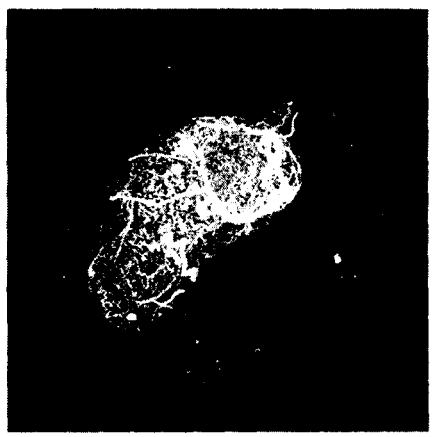
Figure 11O:
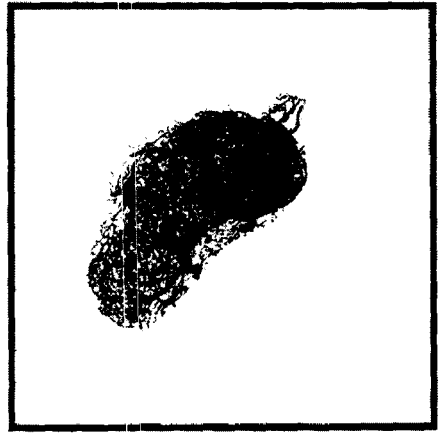
Figure 11Q:
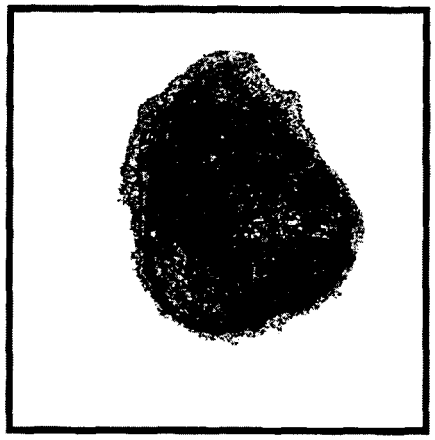
Figure 11S:
Figure 11P:
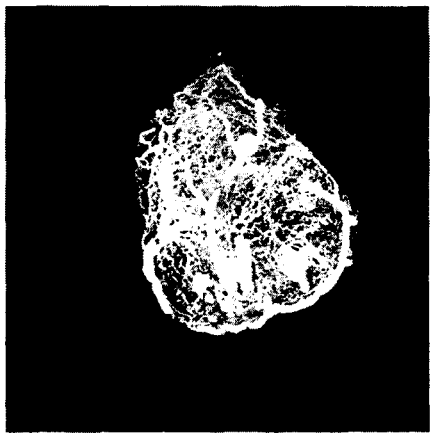
Figure 11R:
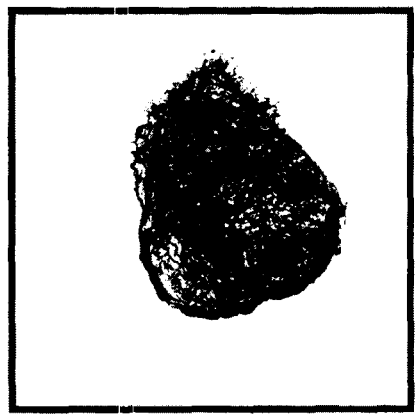
Figure 11U:
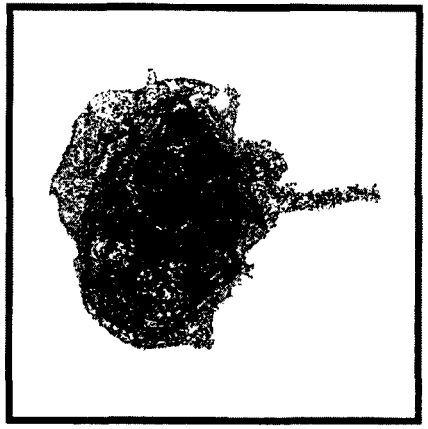
Figure 11W:
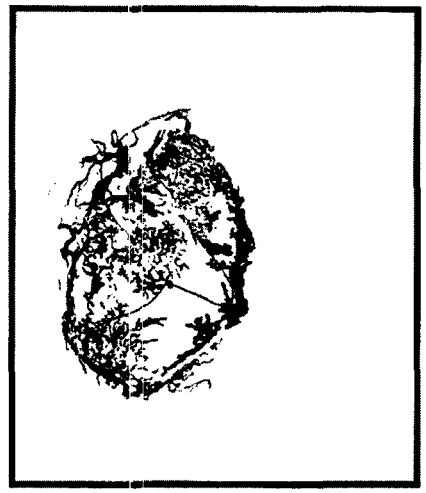
Figure 11T:
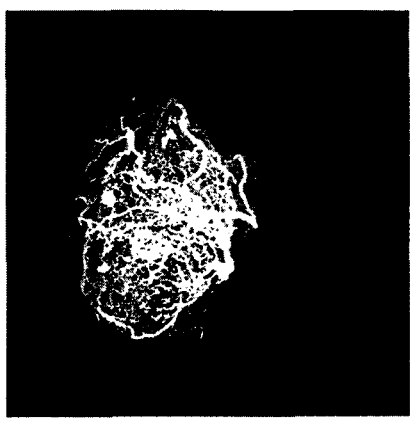
Figure 11V:
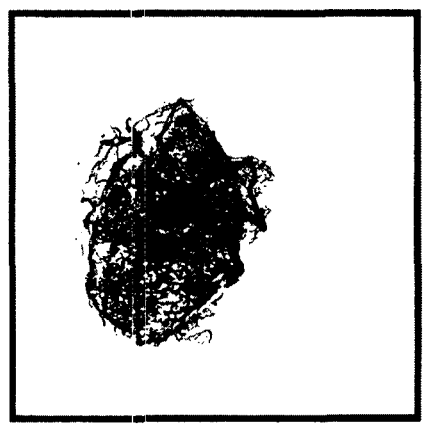
Figure 11Y:
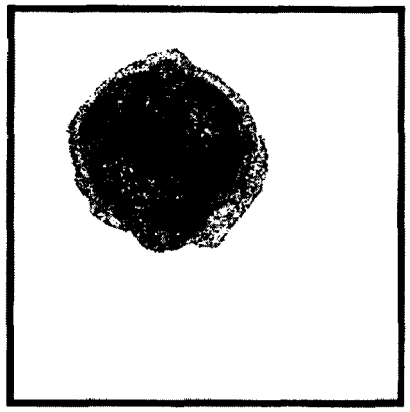
Figure 11A:
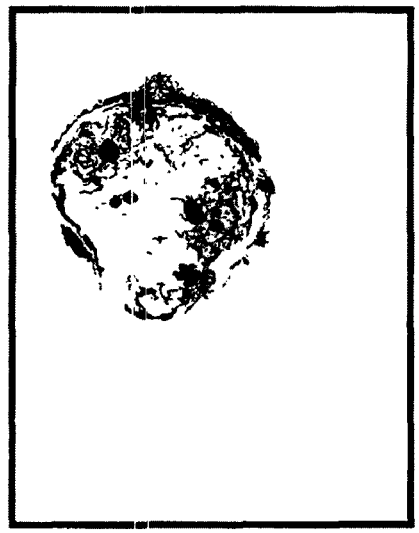
Figure 11X:
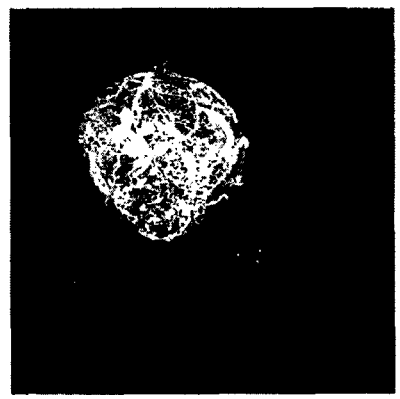
Figure 11Z:
Figure 11C:
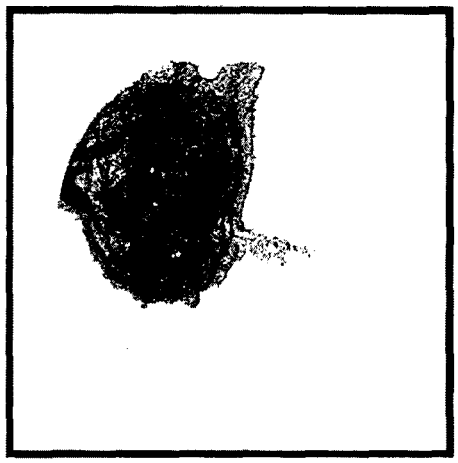
Figure 11E:
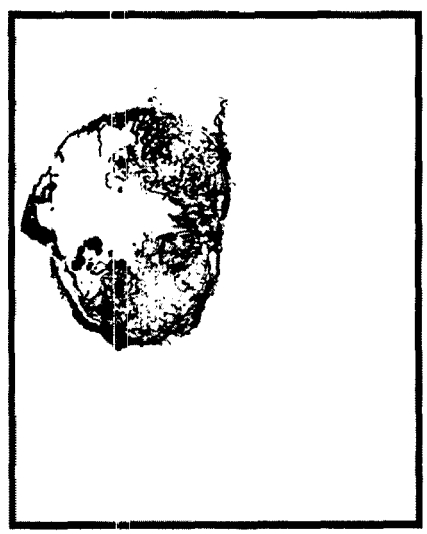
Figure 11B:
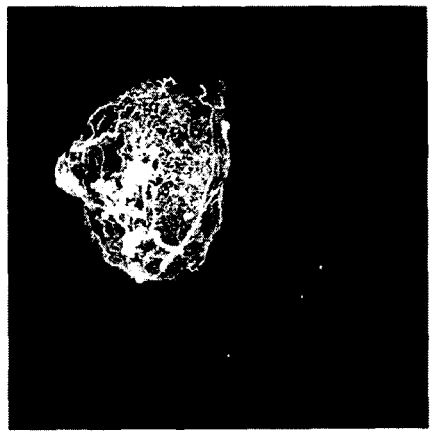
Figure 11D:
Figure 11G:
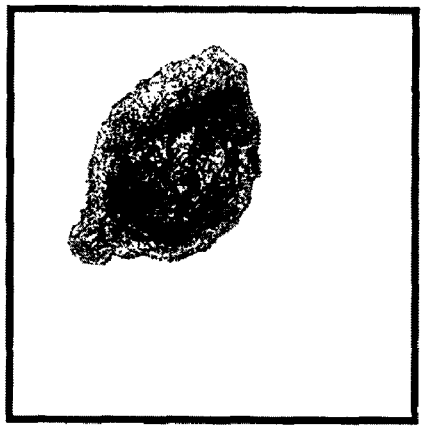
Figure 11I:
Figure 11F:
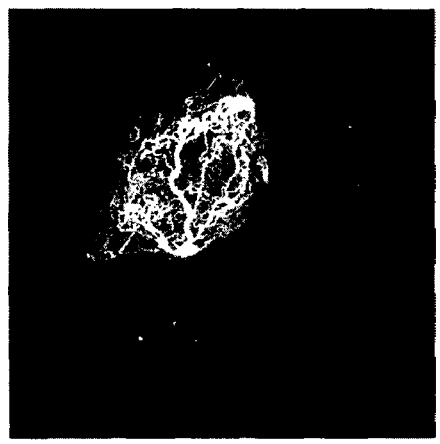
Figure 11H:
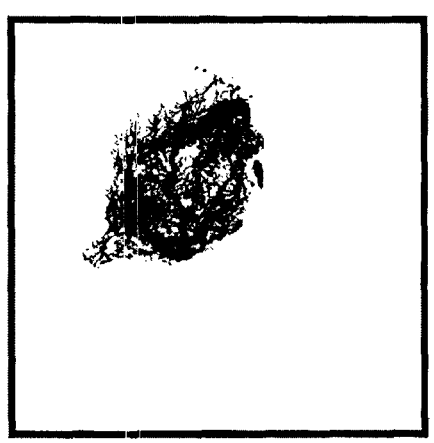
Figure 11K:
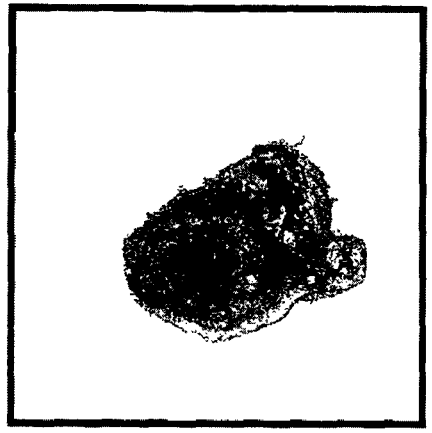
Figure 11M:
Figure 11J:
Figure 11L:
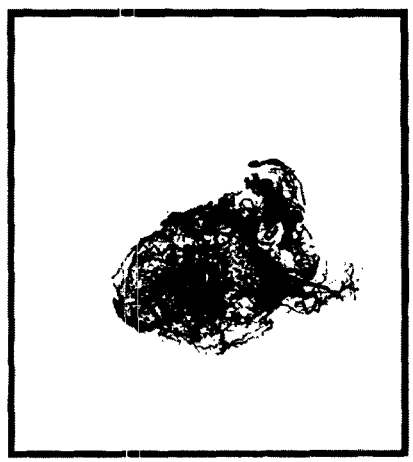
Figure 12B:
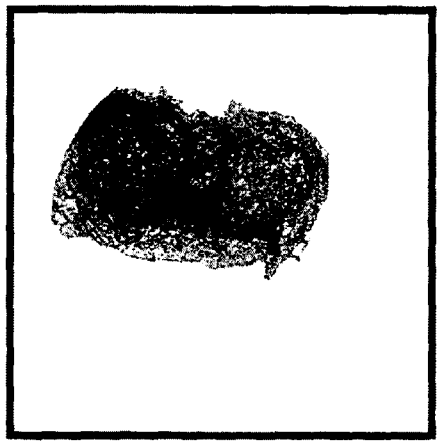
Figure 12D:
Figure 12A:
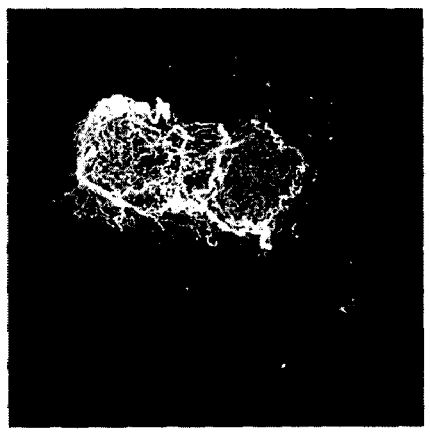
Figure 12C:
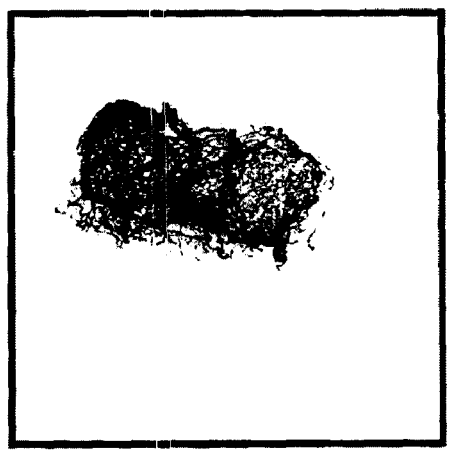
Figure 12F:
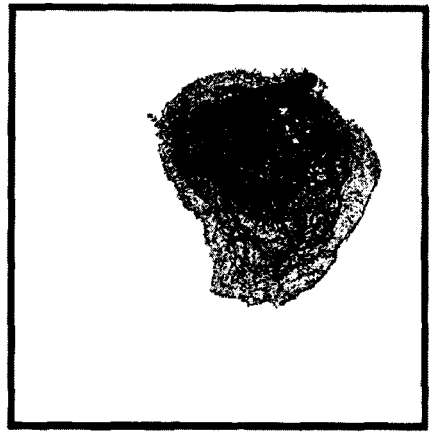
Figure 12H:
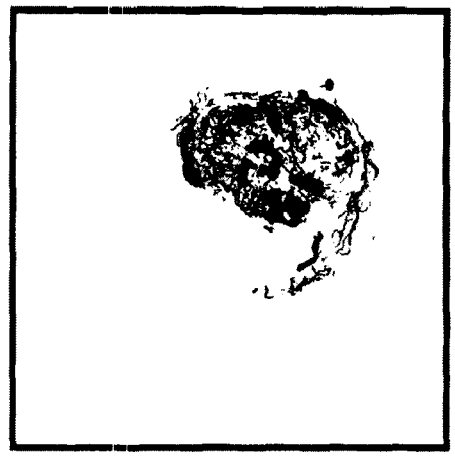
Figure 12E:
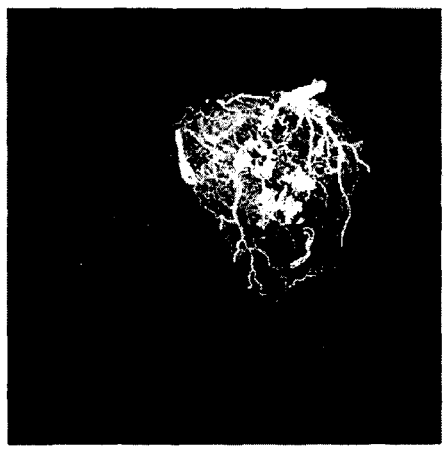
Figure 12G:
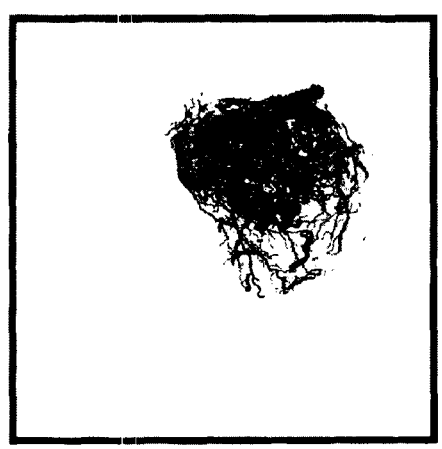
Figure 12J:
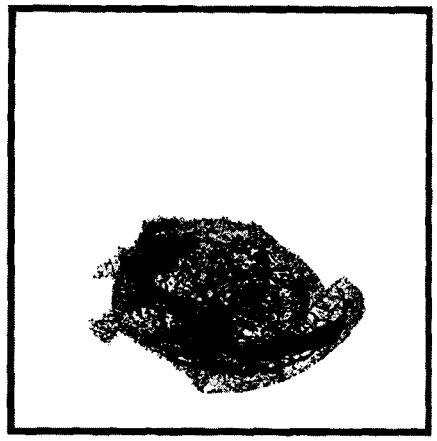
Figure 12L:
Figure 12I:
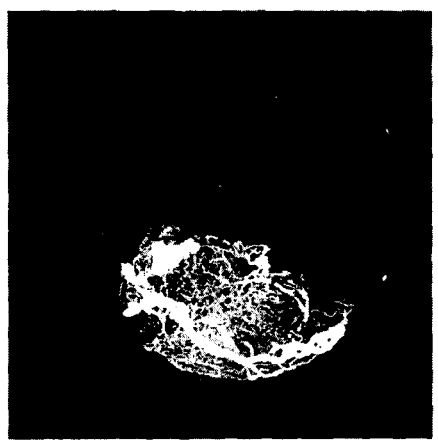
Figure 12K:
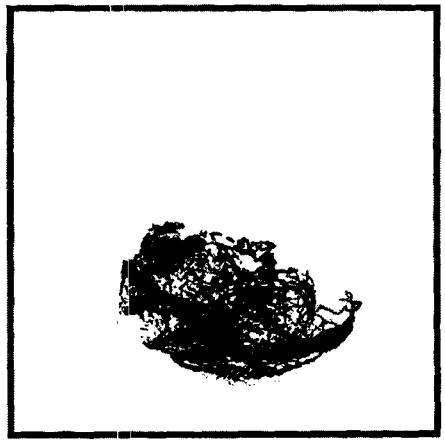
Figure 12N:
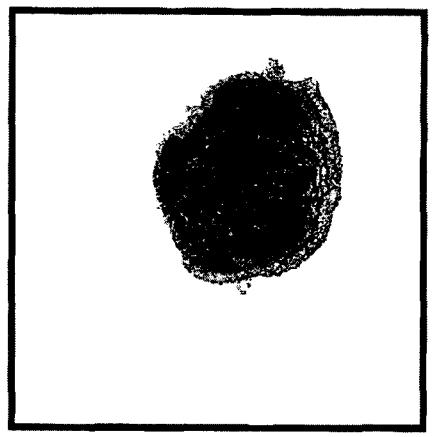
Figure 12P:
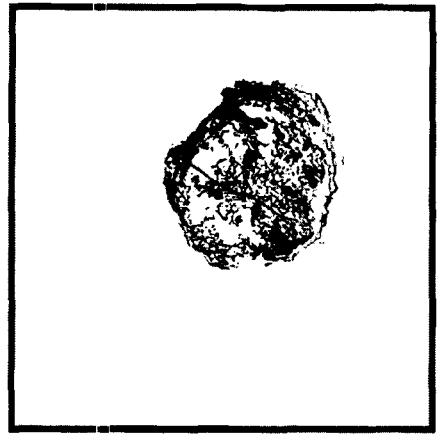
Figure 12M:
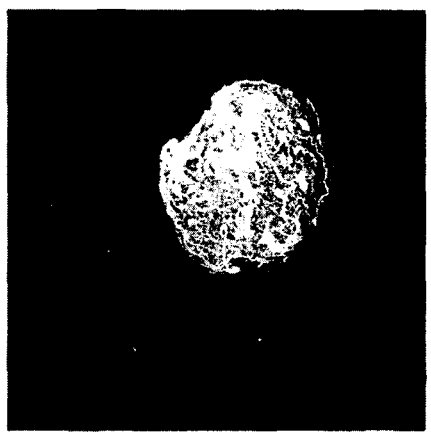
Figure 12O:
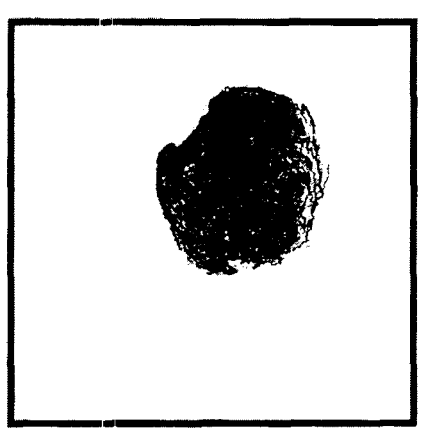
Figure 12R:
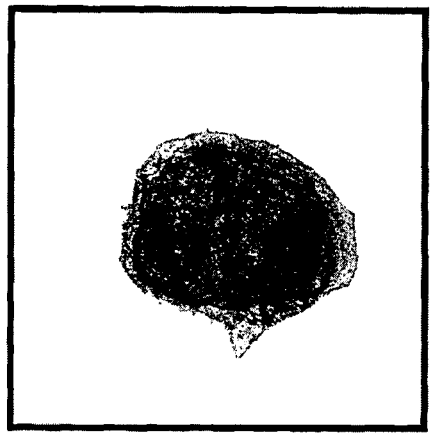
Figure 12T:
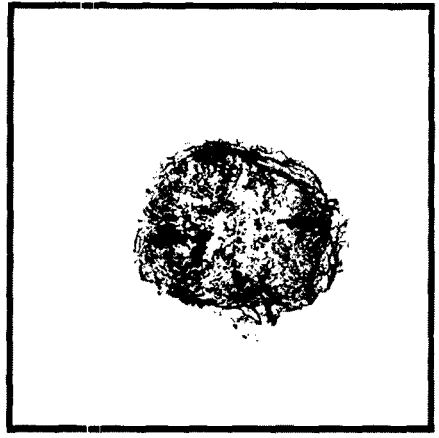
Figure 12Q:
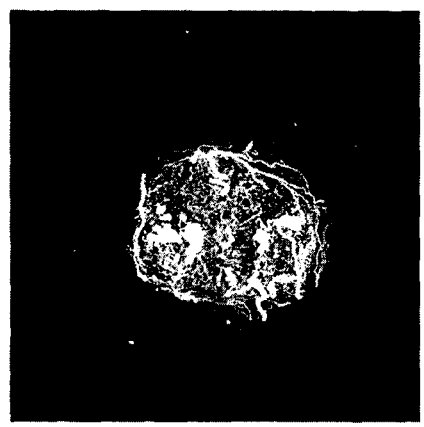
Figure 12S:
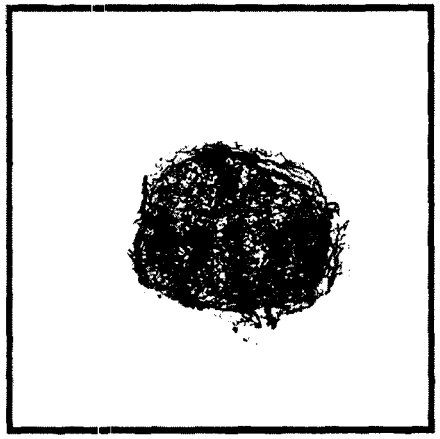
Figure 12V:
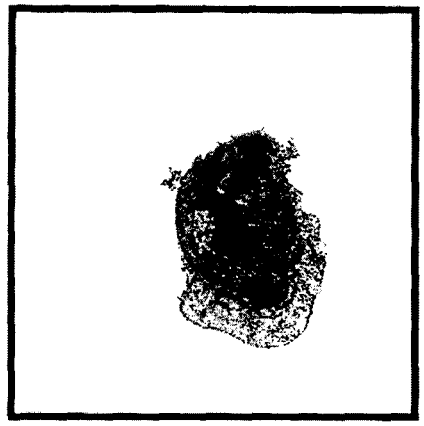
Figure 12X:
Figure 12U:
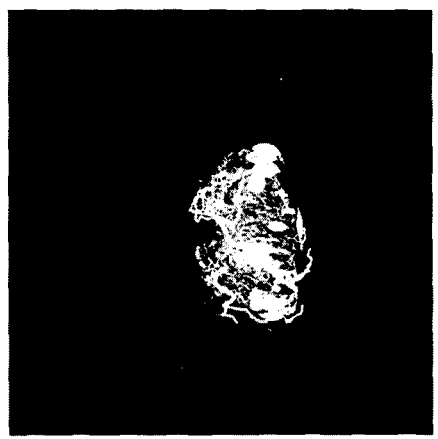
Figure 12W:
Figure 12Z:
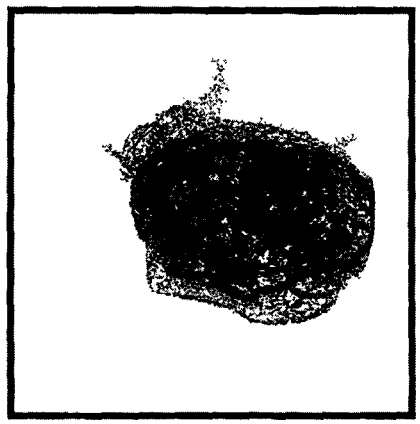
Figure 12B:
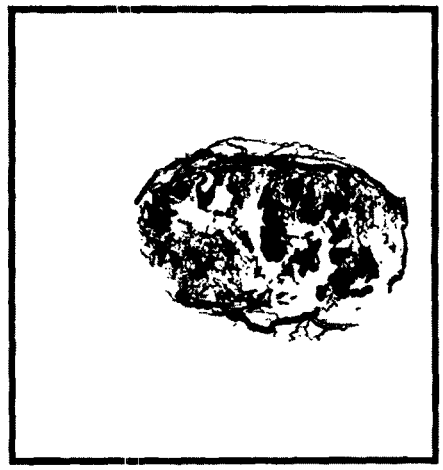
Figure 12Y:
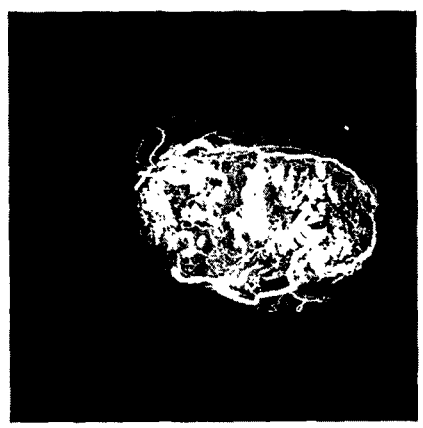
Figure 12A:
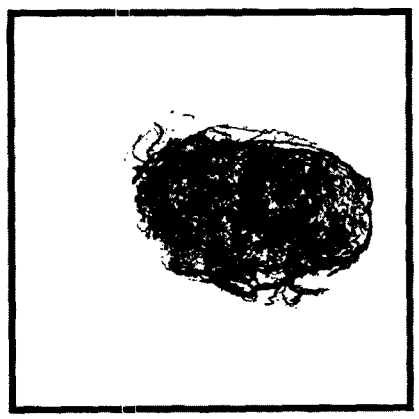
Figure 12D:
Figure 12F:
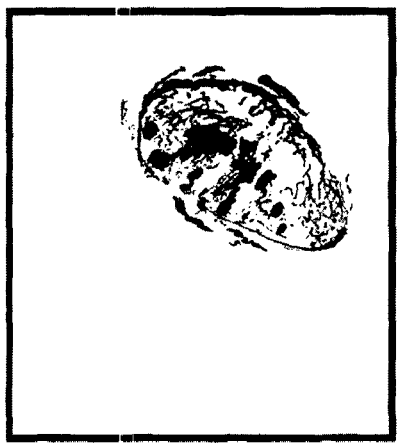
Figure 12C:
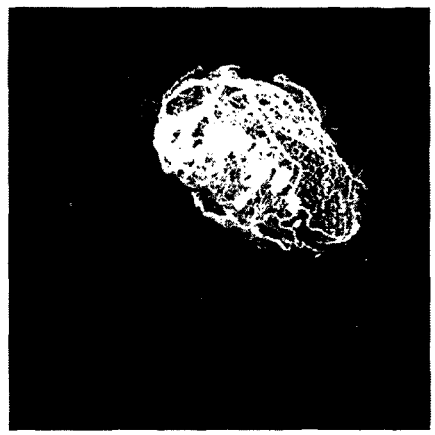
Figure 12E:
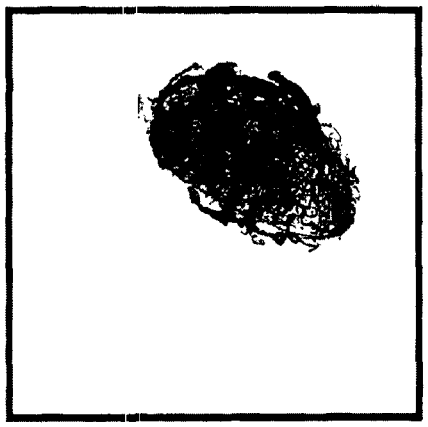
Figure 12H:
Figure 12J:
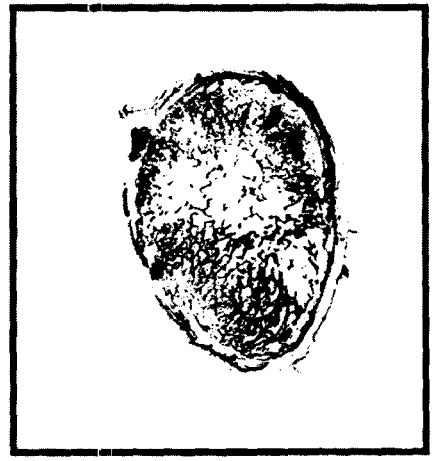
Figure 12G:
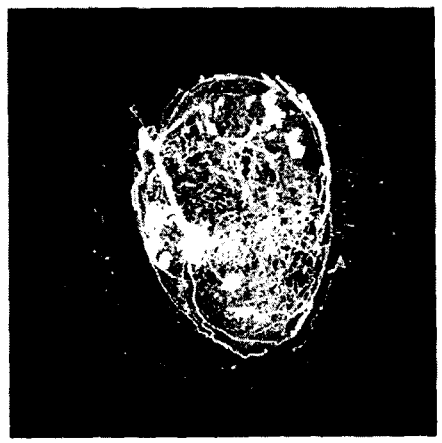
Figure 12I:
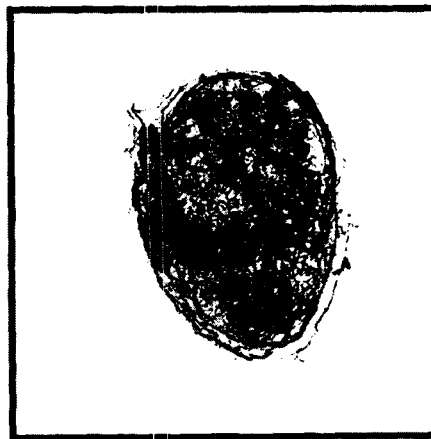
Figure 12L:
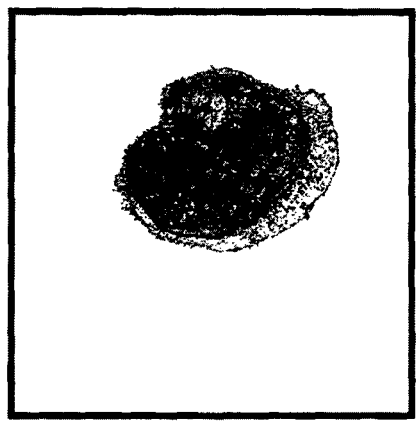
Figure 12N:
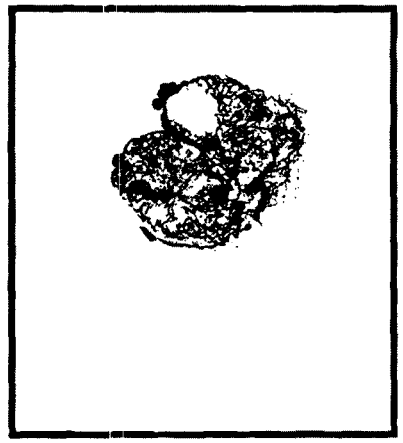
Figure 12K:
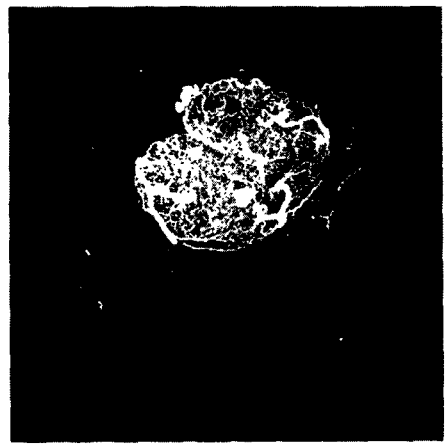
Figure 12M:
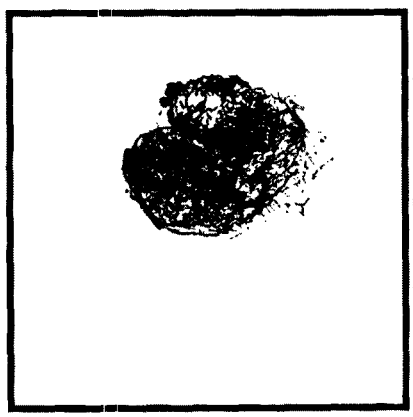
Figure 13B:
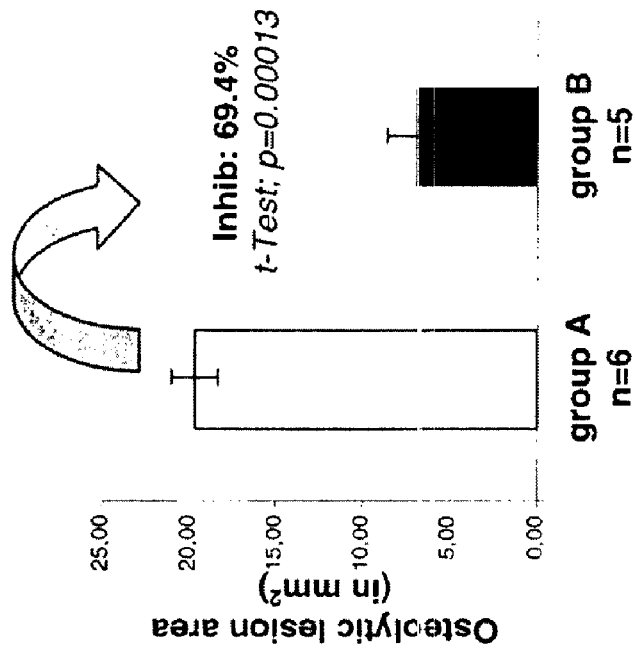
FIGS. 13A-13D illustrate the effects of a test compound on lytic bone metastasis.
Figure 13A:
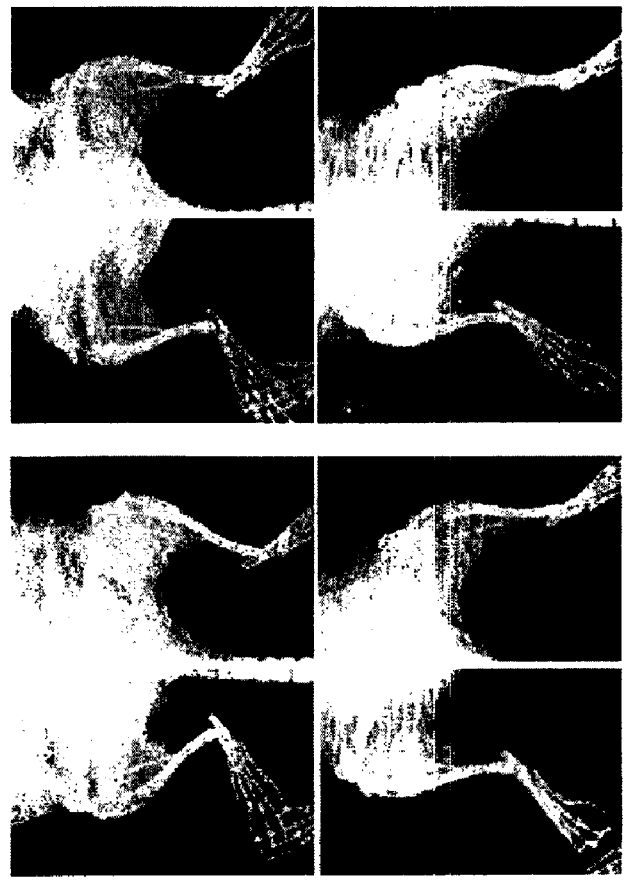
Figure 13C:
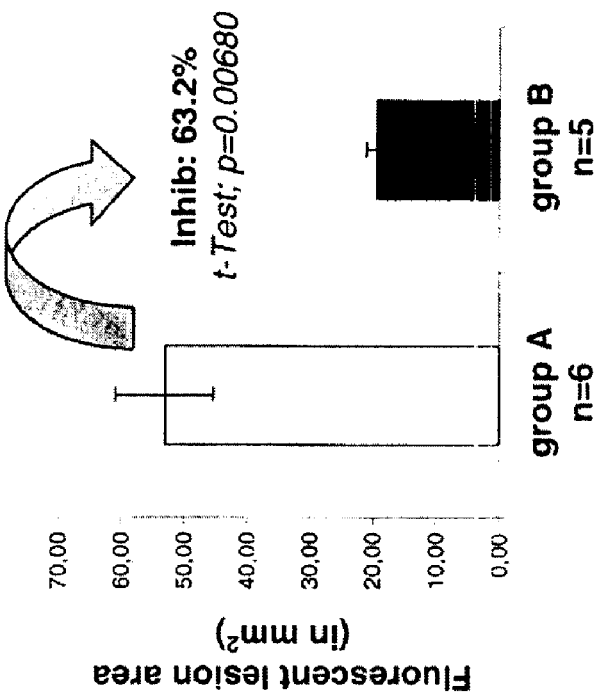
Figure 13D:
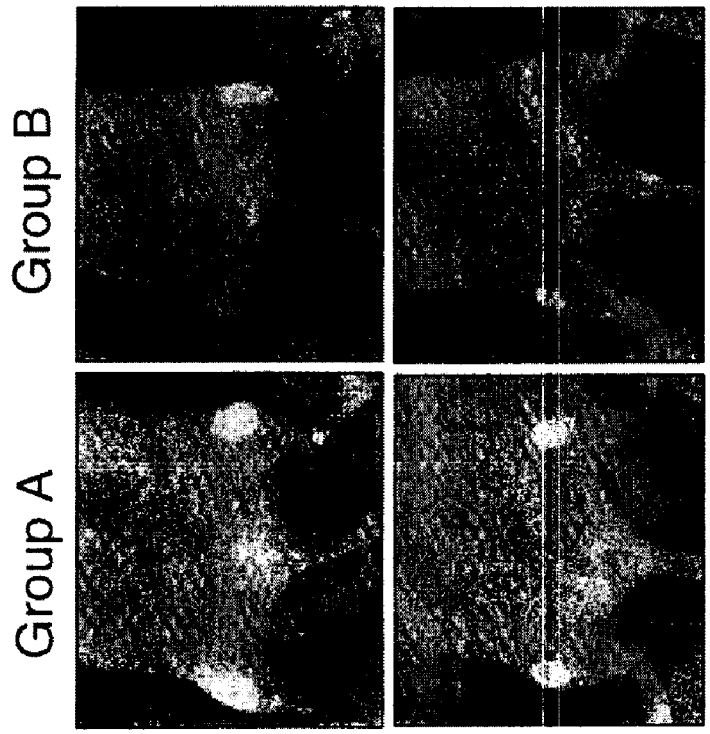

Statistical analysis was performed with JMP statistical software package (SAS Institute Inc., Cary, N.C., USA). Group comparisons for Micro-CT metrics (VV, TV, VV/TV) were evaluated with Dunnett's test for multiple comparisons. P-values less than 0.05 were considered significant. Results are illustrated in FIG. 10 for the control (vehicle), in FIG. 11 for control FTY-720, and FIG. 12 for test compound 51299.

EXAMPLE 85

Bone Metastasis

Mice are tested for assessing lytic bone metastasis. Athymic (nude) mice were injected with a osteo-tropic subclone of the human breast CA line, MDA MB-231. After two weeks the bones are scanned to assess the cancer in the bone. The cancer is treated for two weeks and the lesions are imaged. The lesions are significantly smaller in mice treated with LPA, receptor antagonists such as VPC51299 or Kil6425 as described in Boucharaba, A., et al. (2006) Proc. Natl. Acad. Sci. v. 103, pp. 9643-9648. The results are illustrated in FIG. 13.

The disclosures of each and every patent, patent application, and publication cited herein are expressly incorporated herein by reference in their entirety into this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure and the claims shown below are not limited to the illustrative embodiments set forth herein.

What is claimed is:

1. A compound having the formula

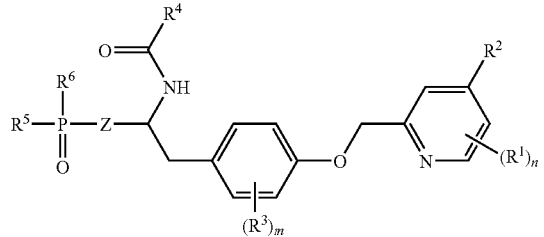

wherein Z is —CY=CH— in the trans (e) configuration;
Y is hydrogen or halogen,
each $R^1$ is independently halo, $(C_1-C_6)$alkyl, halo$(C_1-C_6)$alkyl, $(C_1-C_6)$alkoxy, —NH$_2$, —NH$(C_1-C_6)$alkyl, —N$((C_1-C_6)$alkyl$)_2$, or cyano; and
$R^2$ is hydrogen, halo, $(C_1-C_{12})$alkyl, halo$(C_1-C_{12})$alkyl, halo$(C_1-C_{12})$alkoxyl, $(C_3-C_{10})$cycloalkyl, $(C_2-C_{12})$alkenyl, $(C_2-C_{12})$alkynyl, —NH$_2$, —NH$(C_1-C_{12})$alkyl, —N$((C_1-C_{12})$alkyl$)_2$, aryl, $(C_1-C_{12})$alkaryl, aryl$(C_1-C_{12})$alkyl, or aryl-substituted aryl$(C_1-C_{12})$alkyl;
each $R^3$ is independently halo, $(C_1-C_{12})$alkyl, halo$(C_1-C_{12})$alkyl, halo$(C_1-C_{12})$alkoxyl, $(C_3-C_{10})$cycloalkyl, $(C_2-C_{12})$alkenyl, $(C_2-C_{12})$alkynyl, —NH2, —NH$(C_1-C_{12})$ alkyl, —N$((C_1-C_{12})$alkyl$)_2$, aryl, $(C_1-C_{12})$alkaryl, aryl$(C_1-C_{12})$alkyl, or aryl-substituted aryl$(C_1-C_{12})$ alkyl;
$R^4$ is $(C_6-C_{24})$alkyl, halo$(C_6-C_{24})$alkyl, $(C_6-C_{24})$alkoxy, —NH2, —NH$(C_1-C_{24})$alkyl, —N$((C_1-C_{24})$alkyl$)_2$, cyano, $(C_3-C_{10})$cycloalkyl, $(C_4-C_{15})$bicycloalkyl, $(C_6-C_{24})$alkenyl, $(C_6-C_{24})$alkenyl, $(C_6-C_{24})$-alkynyl, aryl, $(C_6-C_{24})$alkaryl, aryl$(C_6-C_{24})$alkyl, or aryl-substituted aryl$(C_6-C_{24})$alkyl;
wherein the alkyl, alkenyl aryl groups of R4 can be optionally substituted with halo, alkoxy or cyano; or
$R^5$ and $R^6$ are independently hydroxy, $(C_1-C_{12})$alkyl-O—, $(C_2-C_{12})$alkenyl-O—, $(C_2-C_{12})$alkynyl-O—, $(C_6-C_{10})$aryl-O—,

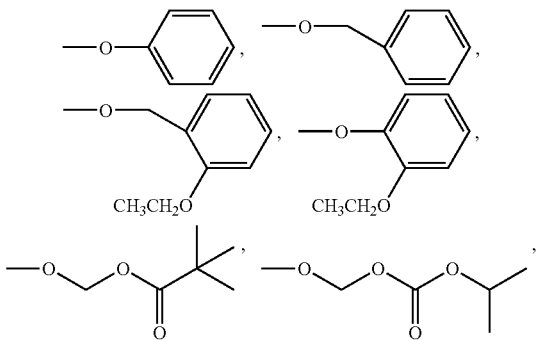

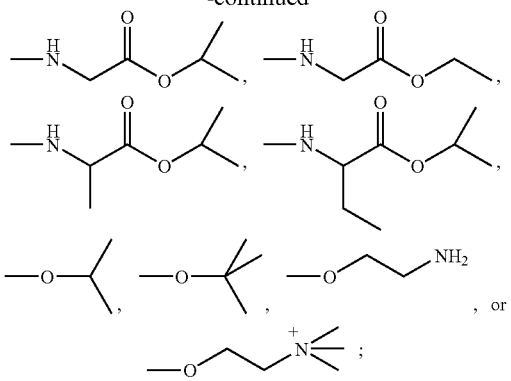

m is 0, 1, 2, 3, or 4; n is 0, 1, 2, or 3; or a pharmaceutically acceptable salt or ester thereof.

2. The compound of claim 1, wherein $R^2$ is hydrogen, methyl, ethyl, fluoro, chloro, trifluoromethyl, trifluoromethoxy, 1,1,1-trifluoroethyl, 1,1,1-trifluoroethoxy, methoxy, ethoxy, propoxy, butoxy, pentoxy.

3. The compound of claim 1, wherein Y is hydrogen, fluorine, chlorine or bromine.

4. The compound of claim 3, wherein Y is hydrogen or fluorine.

5. The compound of claim 1, wherein $R^1$ is fluorine, trifluoromethyl, trifluoromethoxy, 1,1,1-trifluoroethyl, 1,1,1-trifluoroethoxy, methoxy, or ethoxy.

6. The compound of claim 1, wherein $R^3$ is fluorine, chlorine, bromine, trifluoro-methyl, methoxy, $(C_1-C_6)$alkyl, $(C_1-C_6)$haloalkyl, or $(C_1-C_6)$alkyl substituted with, alkoxy or cyano.

7. The compound of claim 6, wherein $R^3$ is fluorine, trifluoromethyl, trifluoromethoxy, 1,1,1-trifluoroethyl, 1,1,1-trifluoroethoxy, methoxy, or ethoxy.

8. The compound of claim 1, wherein $R^2$ is hydrogen, trifluoromethyl, trifluoromethoxy, 1,1,1-trifluoroethyl, or 1,1,1-trifluoroethoxy.

9. The compound of claim 8, wherein $R^2$ is hydrogen, trifluoromethoxy, or 1,1,1-trifluoroethoxy.

10. The compound of claim 1, wherein $R^4$ is alkyl, or alkenyl.

11. The compound of claim 10, wherein $R^4$ is $C_5H_{11}$, $C_6H_{13}$, $C_7H_{14}CH$=$CHC_8H_{17}$ or $C_{15}H_{31}$.

12. The compound of claim 11, wherein $R^4$ is $C_7H_{14}CH$=$CHC_8H_{17}$ and $C_{15}H_{31}$.

13. The compound of claim 1, wherein $R^5$ and $R^6$ are independently hydroxy, methoxy, or ethoxy,

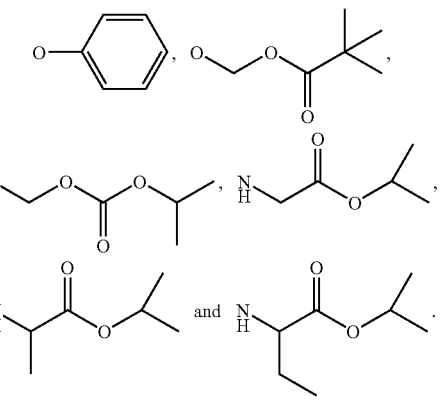

14. The compound of claim 13, wherein $R^5$ and $R^6$ are independently hydroxy, methoxy, or ethoxy.

15. The compound of claim 1, wherein having the formula:

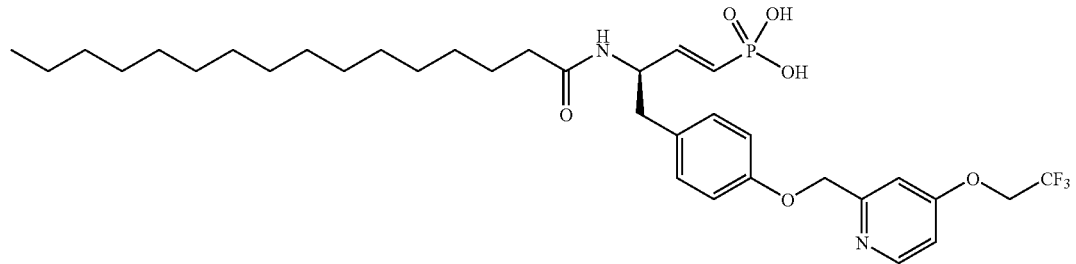

16. A composition comprising the compound of claim 1, and a pharmaceutically acceptable carrier.

17. A kit for administering at least one compound of claim 1, to a patient in need thereof, said kit comprising a pharmaceutical composition comprising at least one compound, an applicator, and instructional material for the use thereof.

* * * * *

UNITED STATES PATENT AND TRADEMARK OFFICE
CERTIFICATE OF CORRECTION

| | |
|---|---|
| PATENT NO. | : 8,283,339 B2 |
| APPLICATION NO. | : 12/357728 |
| DATED | : October 9, 2012 |
| INVENTOR(S) | : Carter et al. |

It is certified that error appears in the above-identified patent and that said Letters Patent is hereby corrected as shown below:

In the specification

In column 1, line 17-19, delete "United States Government support under Grant No. Grant No R0I GM052722 awarded by the National Institutes of Health. The United States Government may have certain rights in the invention." and insert --government support under GM052722 awarded by the National Institutes of Health. The government has certain rights in the invention.--, therefor.

Signed and Sealed this
Twenty-sixth Day of April, 2016

Michelle K. Lee
*Director of the United States Patent and Trademark Office*